(12) United States Patent
Mandelboim et al.

(10) Patent No.: US 8,980,244 B2
(45) Date of Patent: Mar. 17, 2015

(54) METHOD OF TREATING TYPE 1 DIABETES BY ADMINISTERING NKP46 POLYPEPTIDE

(71) Applicants: Yissum Research Development Company of the Hebrew University of Jerusalem Ltd., Givat Ram, Jerusalem (IL); Hadasit Medical Research Services and Development Ltd., Jerusalem (IL); Ben-Gurion University of the Negev Research and Development Authority, Beer Sheva (IL)

(72) Inventors: Ofer Mandelboim, Shoham (IL); Angel Porgador, Lehavim (IL); Yaakov Naparstek, Jerusalem (IL); Chamutal Gur, Jerusalem (IL)

(73) Assignees: Ben-Gurion University of the Negev Research and Development Authority, Beer Sheva (IL); Hadasit Medical Research Services and Development Ltd., Jerusalem (IL); Yissum Research Development Company of the Hebrew University of Jerusalem, Ltd., Jerusalem (IL)

( * ) Notice: Subject to any disclaimer, the term of this patent is extended or adjusted under 35 U.S.C. 154(b) by 0 days.

(21) Appl. No.: 13/862,927

(22) Filed: Apr. 15, 2013

(65) Prior Publication Data

US 2013/0280209 A1    Oct. 24, 2013

Related U.S. Application Data

(62) Division of application No. 13/257,349, filed as application No. PCT/IL2010/000228 on Mar. 18, 2010, now Pat. No. 8,420,092.

(60) Provisional application No. 61/202,629, filed on Mar. 19, 2009, provisional application No. 61/259,640, filed on Nov. 10, 2009.

(51) Int. Cl.

| | | |
|---|---|---|
| *A61K 38/17* | (2006.01) | |
| *A61K 39/395* | (2006.01) | |
| *C07K 16/28* | (2006.01) | |
| *C07K 14/705* | (2006.01) | |
| *A61P 3/10* | (2006.01) | |
| *A61K 39/00* | (2006.01) | |
| *A61K 38/00* | (2006.01) | |

(52) U.S. Cl.
CPC ........... *A61K 39/3955* (2013.01); *C07K 14/705* (2013.01); *C07K 14/70503* (2013.01); *C07K 16/2803* (2013.01); *C07K 16/2851* (2013.01); *A61K 2039/505* (2013.01); *C07K 2319/30* (2013.01); *A61K 38/00* (2013.01)
USPC ............. 424/85.2; 514/5.9; 514/6.9; 514/7.2; 514/7.3

(58) Field of Classification Search
None
See application file for complete search history.

(56) References Cited

U.S. PATENT DOCUMENTS

| | | | |
|---|---|---|---|
| 4,816,397 | A | 3/1989 | Boss |
| 4,816,567 | A | 3/1989 | Cabilly |
| 4,946,778 | A | 8/1990 | Ladner |
| 5,693,762 | A | 12/1997 | Queen |
| 5,712,120 | A | 1/1998 | Rodriguez |
| 5,969,108 | A | 10/1999 | McCafferty |
| 2004/0038339 | A1 | 2/2004 | Kufer |
| 2007/0203054 | A1 | 8/2007 | Mandelboim |
| 2007/0231813 | A1 | 10/2007 | Cartron |
| 2008/0274047 | A1 | 11/2008 | Romagne |

FOREIGN PATENT DOCUMENTS

| | | |
|---|---|---|
| WO | 91/17271 | 11/1991 |
| WO | 92/01047 | 1/1992 |
| WO | 02/08287 A2 | 1/2002 |
| WO | 02/072631 | 9/2002 |
| WO | 2004/053054 | 6/2004 |
| WO | 2005/000086 | 1/2005 |
| WO | 2005/051973 | 6/2005 |
| WO | 2007/042573 | 4/2007 |
| WO | 2009/148568 | 12/2009 |

OTHER PUBLICATIONS

Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, Current Opinion in Structural Biology 2009, 19: 596-604.*
Gur et al, The Journal of Immunology, 2011, vol. 187, pp. 3096-3103.*
Sarrazin et al, Cold Spring Harbor Perspectives in Biology, 2011, vol. 3, No. 7, pp. 1-33.*
ISR of PCT/IL2010/000228 mailed Sep. 13, 2010.
Lynch et al, Obesity, 2009, vol. 17, No. 3, pp. 601-605.
Aktas et al., (2009) Relationship between CD107a expression and cytotoxic activity. Cell Immunol 254: 149-154.
Alba et al., (2004) IFN beta accelerates autoimmune type 1 diabetes in nonobese diabetic mice and breaks the tolerance to beta cells in nondiabetes-prone mice. J Immunol 173: 6667-6675.
Alba et al., (2008) Natural killer cells are required for accelerated type 1 diabetes driven by interferon-beta. Clin Exp Immunol 151: 467-475.
Alter et al., (2004) CD107a as a functional marker for the identification of natural killer cell activity. J Immunol Methods 294: 15-22.
Altschul et al., (1990) Basic local alignment search tool. J Mol Biol 215(3):403-410.

(Continued)

*Primary Examiner* — Joanne Hama
*Assistant Examiner* — Fozia Hamud
(74) *Attorney, Agent, or Firm* — Browdy and Neimark, PLLC

(57) ABSTRACT

The invention relates to use of the natural cytotoxicity receptor NKp46 for preventing and treating diabetes, including type I diabetes (TID) and type 2 diabetes. In particular, the invention provides compositions comprising a fragment of the extracellular region of NKp46 for preventing the onset and progression of diabetes.

18 Claims, 15 Drawing Sheets

(56) References Cited

OTHER PUBLICATIONS

Altschul et al., (1997) Gapped BLAST and PSI-BLAST: a new generation of protein database search programs. Nucleic Acids Res 25(17): 3389-3402.
Arnon et al., (2001) Recognition of viral hemagglutinins by NKp44 but not by NKp30. Eur J Immunol 31: 2680-2689.
Arnon et al., (2004) The mechanisms controlling the recognition of tumor- and virus-infected cells by NKp46. Blood 103: 664-672.
Baert et al., (2003) Influence of immunogenicity on the long-term efficacy of infliximab in Crohn's disease. N Engl J Med 348: 601-608.
Biassoni et al., (1999) The murine homologue of the human NKp46, a triggering receptor involved in the induction of natural cytotoxicity. Eur J Immunol 29: 1014-1020.
Carnethon et al., (2003) Risk factors for progression to incident hyperinsulinemia: the Atherosclerosis Risk in Communities Study, 1987-1998. Am J Epidemiol 158(11):1058-1067.
Chaturvedi et al., (1996) Stabilization of triple-stranded oligonucleotide complexes: use of probes containing alternating phosphodiester and stereo-uniform cationic phosphoramidate linkages. Nucleic Acids Res 24(12):2318-2323.
Clackson et al. (1991) Making antibody fragments using phage display libraries. Nature 352(6336): 624-628.
Delovitch and Singh (1997) The nonobese diabetic mouse as a model of autoimmune diabetes: immune dysregulation gets the NOD. Immunity 7: 727-738.
Dotta et al., (2007) Coxsackie B4 virus infection of beta cells and natural killer cell insulitis in recent-onset type 1 diabetic patients. Proc Natl Acad Sci U S A 104: 5115-5120.
Flodstrom et al., (1999) Reduced sensitivity of inducible nitric oxide synthase-deficient mice to multiple low-dose streptozotocin-induced diabetes. Diabetes 48: 706-713.
Flodstrom et al., (2002) The natural killer cell—friend or foe in autoimmune disease? Scand J Immunol 55: 432-441.
Foulis et al., (1997) A search for evidence of viral infection in pancreases of newly diagnosed patients with IDDM. Diabetologia 40: 53-61.
Gazit et al., (2006) Lethal influenza infection in the ab 5 sence of the natural killer cell receptor gene Ncr1. Nat Immunol 7: 517-523.
Gur et al., (2010) The activating receptor NKp46 is essential for the development of type 1 diabetes. Nat Immunol 11 (2): 121-128.
Gurr et al., (2007) RegII is a beta-cell protein and autoantigen in diabetes of NOD mice. Diabetes 56: 34-40.
Halfteck et al., (2009) Enhanced in vivo growth of lymphoma tumors in the absence of the NK-activating receptor 5 NKp46/NCR1. J Immunol 182: 2221-2230.
Hanna et al., (2004) Novel APC-like properties of human NK cells directly regulate T cell activation. J Clin Invest 114: 1612-1623.
Hansson et al., (1981) Human fetal thymus and bone marrow contain target cells for natural killer cells. Eur J Immunol 11:8-12.
Horwitz et al., (1998) Diabetes induced by Coxsackie virus: initiation by bystander damage and not molecular mimicry. Nat Med 4: 781-785.
Huse et al., (1989) Generation of a large combinatorial library of the immunoglobulin repertoire in phage lambda. Science 246(4935): 1275-1281.
Hutchings et al., (1990) Transfer of diabetes in mice prevented by blockade of adhesion-promoting receptor on macrophages. Nature 348: 639-642.
Jones et al., (1986) Replacing the complementarity-determining regions in a human antibody with those from a mouse. Nature 321(6069): 522-525.
Karlin and Altschul (1993) Applications and statistics for multiple high-scoring segments in molecular sequences. Proc Natl Acad Sci U S A 90(12): 5873-5877.
Karre (2002) NK cells, MHC class I molecules and the missing self. Scand J Immunol 55: 221-228.
Kikutani and Makino (1992) The murine autoimmune diabetes model: NOD and related strains. Adv Immunol 51: 285-322.

Kitagawa et al., (1991) Islet cells but not thyrocytes are susceptible to lysis by NK cells. J Autoimmun 4: 703-716.
Kohler and Milstein (1975) Continuous cultures of fused cells secreting antibody of predefined specificity. Nature 256 (5517): 495-497.
Lanier (2005) NK cell recognition. Annu Rev Immunol 23: 225-274.
Like and Rossini (1976) Streptozotocin-induced pancreatic insulitis: new model of diabetes mellitus. Science 193: 415-417.
Lodde et al., (2006) NOD mouse model for Sjogren's syndrome: lack of longitudinal stability. Oral Dis 12: 566-572.
Lodoen et al., (2003) NKG2D-mediated natural killer cell protection against cytomegalovirus is impaired by viral gp40 modulation of retinoic acid early inducible 1 gene molecules. J Exp Med 197: 1245-1253.
Loghmani (2005) Diabetes Mellitus: Type I and Type 2. Stang J, Story M (eds) Guidelines for Adolescent Nutrition Services, Chaper 14, pp. 167-182.
Long (2002) Tumor cell recognition by natural killer cells. Semin Cancer Biol 12: 57-61.
Lynch et al., (2009) Are natural killer cells protecting the metabolically healthy obese patient? Obesity 17(3): 601-605.
MacKay et al., (1986) Spontaneous diabetes mellitus in the Bio Breeding/Worcester rat. Evidence in vitro for natural killer cell lysis of islet cells. J Clin Invest 77: 916-924.
Maier et al., (2008) NKG2D-RAE-1 receptor-ligand variation does not account for the NK cell defect in nonobese diabetic mice. J Immunol 181: 7073-7080.
Mandelboim et al., (2001) Recognition of haemagglutinins on virus-infected cells by NKp46 activates lysis by human NK cells. Nature 409: 1055-1060.
Marks et al., (1991) By-passing immunization. Human antibodies from V-gene libraries displayed on phage. J Mol Biol 222(3): 581-597.
Matsumoto et al., (2007) Isolation of tissue progenitor cells from duct-ligated salivary glands of swine. Cloning Stem Cells 9: 176-190.
Mayfield (1998) Diagnosis and classification of diabetes mellitus: new criteria. Am Fam Physician 58(6): 1355-62, 1369-1370.
Miyazaki et al., (1985) Predominance of T lymphocytes in pancreatic islets and spleen of pre-diabetic non-obese diabetic (NOD) mice: a longitudinal study. Clin Exp Immunol 60: 622-630.
Moretta (2005) Lymphocyte effector mechanisms in innate and adaptive immunity. Curr Opin Immunol 17: 303-305.
Moretta et al., (2002) What is a natural killer cell? Nat Immunol 3: 6-8.
Morse et al., (2001) NK cell-mediated lysis of autologous human oligodendrocytes. J Neuroimmunol 116: 107-115.
Nakamura et al., (1990) Intrinsic cytotoxicity of natural killer cells to pancreatic islets in vitro. Diabetes 39(7): 836-843.
Niwa et al., (1999) A role for presenilin-1 in nuclear accumulation of Ire1 fragments and induction of the mammalian unfolded protein response. Cell 99(7): 691-702.
O'Brien et al., (1996) Beta-cell apoptosis is responsible for the development of IDDM in the multiple low-dose streptozotocin model. J Pathol 178(2): 176-181.
Ogasawara et al., (2003) Impairment of NK cell function by NKG2D modulation in NOD mice. Immunity 18(1): 41-51.
Ogasawara et al., (2004) NKG2D blockade prevents autoimmune diabetes in NOD mice. Immunity 20(6): 757-767.
Paik et al., (1980) Insulin-dependent diabetes mellitus induced by subdiabetogenic doses of streptozotocin: obligatory role of cellmediated autoimmune processes. Proc Natl Acad Sci USA 77(10): 6129-6133.
Pessino et al., (1998) Molecular cloning of NKp46: a novel member of the immunoglobulin superfamily involved in triggering of natural cytotoxicity. J Exp Med 188(5): 953-960.
Peyrottes et al., (1996) Oligodeoxynucleoside phosphoramidates (P-NH2): synthesis and thermal stability of duplexes with DNA and RNA targets. Nucleic Acids Res 24(10): 1841-1848.
Poirot et al., (2004) Natural killer cells distinguish innocuous and destructive forms of pancreatic islet autoimmunity. Proc Natl Acad Sci USA 101(21): 8102-8107.
Presta (1992) Antibody Engineering. Curr Op Bioltechnol 3(4): 394-398.

(56) References Cited

OTHER PUBLICATIONS

Raulet (2003) Roles of the NKG2D immunoreceptor and its ligands. Nat Rev Immunol 3(10): 781-790.

Rhodes CJ (2005) Type 2 diabetes—a matter of beta-cell life and death? Science 307(5708): 380-384.

Riechmann et al., (1988) Reshaping human antibodies for therapy. Nature 332(6162): 323-329.

Rodacki et al., (2007) Altered natural killer cells in type 1 diabetic patients. Diabetes 56(1): 177-185.

Suresh et al., (1986) Bispecific monoclonal antibodies from hybrid hybridomas. Methods Enzymol 121: 210-228.

GenBank Accession No. CAA04714; Human NKp46 receptor isoform a; Sep. 22, 1998.

GenBank Accession No. CAA06872; Human NKp46 receptor isoform b; Oct. 7, 2008.

GenBank Accession No. CAA06873; Human NKp46 receptor isoform c; Oct. 7, 2008.

GenBank Accession No. CAA06874; Human NKp46 receptor isoform d; Oct. 7, 2008.

GenBank Accession No. AAH42788; Ncr1 protein; Apr. 16, 2003.

GenBank Accession No. NP_034876; Natural cytotoxicity triggering receptor 1 precursor; Sep. 2, 2013.

\* cited by examiner

SEQUENCE LISTING

```
<160> NUMBER OF SEQ ID NOS: 35

<210> SEQ ID NO 1
<211> LENGTH: 134
<212> TYPE: PRT
<213> ORGANISM: Artificial Sequence
<220> FEATURE:
<223> OTHER INFORMATION: Synthetic

<400> SEQUENCE: 1

Tyr Asp Thr Pro Thr Leu Ser Val His Pro Gly Pro Glu Val Ile Ser
1               5                   10                  15

Gly Glu Lys Val Thr Phe Tyr Cys Arg Leu Asp Thr Ala Thr Ser Met
            20                  25                  30

Phe Leu Leu Leu Lys Glu Gly Arg Ser Ser His Val Gln Arg Gly Tyr
        35                  40                  45

Gly Lys Val Gln Ala Glu Phe Pro Leu Gly Pro Val Thr Thr Ala His
    50                  55                  60

Arg Gly Thr Tyr Arg Cys Phe Gly Ser Tyr Asn Asn His Ala Trp Ser
65                  70                  75                  80

Phe Pro Ser Glu Pro Val Lys Leu Leu Val Thr Gly Asp Ile Glu Asn
                85                  90                  95

Thr Ser Leu Ala Pro Glu Asp Pro Thr Phe Pro Ala Asp Thr Trp Gly
            100                 105                 110

Thr Tyr Leu Leu Thr Thr Glu Thr Gly Leu Gln Lys Asp His Ala Leu
        115                 120                 125

Trp Asp His Thr Ala Gln
    130

<210> SEQ ID NO 2
<211> LENGTH: 117
<212> TYPE: PRT
<213> ORGANISM: Artificial Sequence
<220> FEATURE:
<223> OTHER INFORMATION: Synthetic

<400> SEQUENCE: 2

Tyr Asp Thr Pro Thr Leu Ser Val His Pro Gly Pro Glu Val Ile Ser
1               5                   10                  15

Gly Glu Lys Val Thr Phe Tyr Cys Arg Leu Asp Thr Ala Thr Ser Met
            20                  25                  30

Phe Leu Leu Leu Lys Glu Gly Arg Ser Ser His Val Gln Arg Gly Tyr
        35                  40                  45

Gly Lys Val Gln Ala Glu Phe Pro Leu Gly Pro Val Thr Thr Ala His
    50                  55                  60

Arg Gly Thr Tyr Arg Cys Phe Gly Ser Tyr Asn Asn His Ala Trp Ser
```

```
            65                   70                  75                  80

Phe Pro Ser Glu Pro Val Lys Leu Leu Val Thr Gly Asp Ile Glu Asn
                85                  90                  95

Thr Ser Leu Ala Pro Glu Asp Pro Thr Phe Pro Asp His Ala Leu Trp
            100                 105                 110

Asp His Thr Ala Gln
        115

<210> SEQ ID NO 3
<211> LENGTH: 134
<212> TYPE: PRT
<213> ORGANISM: Artificial Sequence
<220> FEATURE:
<223> OTHER INFORMATION: Synthetic

<400> SEQUENCE: 3

Tyr Asp Thr Pro Thr Leu Ser Val His Pro Gly Pro Glu Val Ile Ser
1               5                   10                  15

Gly Glu Lys Val Thr Phe Tyr Cys Arg Leu Asp Thr Ala Thr Ser Met
            20                  25                  30

Phe Leu Leu Lys Glu Gly Arg Ser Ser His Val Gln Arg Gly Tyr
        35                  40                  45

Gly Lys Val Gln Ala Glu Phe Pro Leu Gly Pro Val Thr Thr Ala His
    50                  55                  60

Arg Gly Thr Tyr Arg Cys Phe Gly Ser Tyr Asn Asn His Ala Trp Ser
65                  70                  75                  80

Phe Pro Ser Glu Pro Val Lys Leu Leu Val Thr Gly Asp Ile Glu Asn
                85                  90                  95

Thr Ser Leu Ala Pro Glu Asp Pro Thr Phe Pro Ala Asp Thr Trp Gly
            100                 105                 110

Thr Tyr Leu Leu Thr Thr Glu Thr Gly Leu Gln Lys Asp His Ala Leu
        115                 120                 125

Trp Asp His Thr Ala Gln
        130

<210> SEQ ID NO 4
<211> LENGTH: 117
<212> TYPE: PRT
<213> ORGANISM: Artificial Sequence
<220> FEATURE:
<223> OTHER INFORMATION: Synthetic

<400> SEQUENCE: 4

Tyr Asp Thr Pro Thr Leu Ser Val His Pro Gly Pro Glu Val Ile Ser
1               5                   10                  15

Gly Glu Lys Val Thr Phe Tyr Cys Arg Leu Asp Thr Ala Thr Ser Met
            20                  25                  30

Phe Leu Leu Lys Glu Gly Arg Ser Ser His Val Gln Arg Gly Tyr
        35                  40                  45

Gly Lys Val Gln Ala Glu Phe Pro Leu Gly Pro Val Thr Thr Ala His
    50                  55                  60

Arg Gly Thr Tyr Arg Cys Phe Gly Ser Tyr Asn Asn His Ala Trp Ser
65                  70                  75                  80

Phe Pro Ser Glu Pro Val Lys Leu Leu Val Thr Gly Asp Ile Glu Asn
                85                  90                  95

Thr Ser Leu Ala Pro Glu Asp Pro Thr Phe Pro Asp His Ala Leu Trp
            100                 105                 110
```

Asp His Thr Ala Gln
        115

<210> SEQ ID NO 5
<211> LENGTH: 135
<212> TYPE: PRT
<213> ORGANISM: Artificial Sequence
<220> FEATURE:
<223> OTHER INFORMATION: Synthetic

<400> SEQUENCE: 5

Arg Val Gly Glu Leu Trp Ser Glu Pro Ser Asn Leu Leu Asp Leu Val
1               5                   10                  15

Val Thr Glu Met Tyr Asp Thr Pro Thr Leu Ser Val His Pro Gly Pro
            20                  25                  30

Glu Val Ile Ser Gly Glu Lys Val Thr Phe Tyr Cys Arg Leu Asp Thr
        35                  40                  45

Ala Thr Ser Met Phe Leu Leu Lys Glu Gly Arg Ser Ser His Val
    50                  55                  60

Gln Arg Gly Tyr Gly Lys Val Gln Ala Glu Phe Pro Leu Gly Pro Val
65              70                  75                  80

Thr Thr Ala His Arg Gly Thr Tyr Arg Cys Phe Gly Ser Tyr Asn Asn
                85                  90                  95

His Ala Trp Ser Phe Pro Ser Glu Pro Val Lys Leu Leu Val Thr Gly
            100                 105                 110

Asp Ile Glu Asn Thr Ser Leu Ala Pro Glu Asp Pro Thr Phe Pro Ala
        115                 120                 125

Asp Thr Trp Gly Thr Tyr Leu
    130                 135

<210> SEQ ID NO 6
<211> LENGTH: 40
<212> TYPE: PRT
<213> ORGANISM: Artificial Sequence
<220> FEATURE:
<223> OTHER INFORMATION: Synthetic

<400> SEQUENCE: 6

Glu Asn Thr Ser Leu Ala Pro Glu Asp Pro Thr Phe Pro Ala Asp Thr
1               5                   10                  15

Trp Gly Thr Tyr Leu Leu Thr Thr Glu Thr Gly Leu Gln Lys Asp His
            20                  25                  30

Ala Leu Trp Asp His Thr Ala Gln
        35                  40

<210> SEQ ID NO 7
<211> LENGTH: 23
<212> TYPE: PRT
<213> ORGANISM: Artificial Sequence
<220> FEATURE:
<223> OTHER INFORMATION: Synthetic

<400> SEQUENCE: 7

Phe Leu Leu Leu Lys Glu Gly Arg Ser Ser His Val Gln Arg Gly Tyr
1               5                   10                  15

Gly Lys Val Gln Ala Glu Phe
            20

<210> SEQ ID NO 8
<211> LENGTH: 20
<212> TYPE: PRT

```
<213> ORGANISM: Artificial Sequence
<220> FEATURE:
<223> OTHER INFORMATION: Synthetic

<400> SEQUENCE: 8

Phe Leu Leu Leu Lys Glu Gly Arg Ser Ser His Val Gln Arg Gly Tyr
1               5                   10                  15

Gly Lys Val Gln
            20

<210> SEQ ID NO 9
<211> LENGTH: 142
<212> TYPE: PRT
<213> ORGANISM: Artificial Sequence
<220> FEATURE:
<223> OTHER INFORMATION: Synthetic

<400> SEQUENCE: 9

Leu Lys Leu Val Val Thr Gly Leu Tyr Asp Thr Pro Asn Leu Trp Val
1               5                   10                  15

Tyr Pro Arg Pro Glu Val Thr Leu Gly Glu Asn Val Thr Phe Phe Cys
            20                  25                  30

Gln Leu Lys Thr Ala Thr Ser Lys Phe Phe Leu Leu Lys Glu Arg Gly
        35                  40                  45

Ser Asn His Ile Gln Asn Lys Tyr Gly Asn Ile Gln Ala Glu Phe Pro
    50                  55                  60

Met Gly Pro Val Thr Arg Ala His Arg Gly Thr Tyr Arg Cys Phe Gly
65                  70                  75                  80

Ser Tyr Asn Asp Tyr Ala Trp Ser Phe Pro Ser Glu Pro Val Thr Leu
                85                  90                  95

Leu Ile Thr Gly Gly Val Glu Asn Ser Ser Leu Ala Pro Thr Asp Pro
            100                 105                 110

Thr Ser Ser Leu Asp Tyr Trp Glu Phe Asp Leu Ser Thr Asn Glu Ser
        115                 120                 125

Gly Leu Gln Lys Asp Ser Ala Phe Trp Asp His Thr Thr Gln
    130                 135                 140

<210> SEQ ID NO 10
<211> LENGTH: 134
<212> TYPE: PRT
<213> ORGANISM: Artificial Sequence
<220> FEATURE:
<223> OTHER INFORMATION: Synthetic

<400> SEQUENCE: 10

Tyr Asp Thr Pro Asn Leu Trp Val Tyr Pro Gln Pro Glu Val Thr Leu
1               5                   10                  15

Gly Glu Asn Val Thr Phe Phe Cys Gln Leu Lys Thr Ala Thr Ser Lys
            20                  25                  30

Phe Phe Leu Leu Lys Glu Arg Gly Ser Asn His Ile Gln Asn Lys Tyr
        35                  40                  45

Gly Asn Ile Gln Ala Glu Phe Pro Met Gly Pro Val Thr Arg Ala His
    50                  55                  60

Arg Gly Thr Tyr Arg Cys Phe Gly Ser Tyr Asn Asp Tyr Ala Trp Ser
65                  70                  75                  80

Phe Pro Ser Glu Pro Val Thr Leu Leu Ile Thr Gly Gly Val Glu Asn
                85                  90                  95

Ser Ser Leu Ala Pro Thr Asp Pro Thr Ser Ser Leu Asp Tyr Trp Glu
            100                 105                 110
```

Phe Asp Leu Ser Thr Asn Glu Ser Gly Leu Gln Lys Asp Ser Ala Phe
            115                 120                 125

Trp Asp His Thr Thr Gln
    130

<210> SEQ ID NO 11
<211> LENGTH: 538
<212> TYPE: PRT
<213> ORGANISM: Artificial Sequence
<220> FEATURE:
<223> OTHER INFORMATION: Synthetic

<400> SEQUENCE: 11

Met Ser Ser Thr Leu Pro Ala Leu Leu Cys Val Gly Leu Cys Leu Ser
1               5                   10                  15

Gln Arg Ile Ser Ala Gln Gln Thr Leu Pro Lys Pro Phe Ile Trp
            20                  25                  30

Ala Glu Pro His Phe Met Val Pro Lys Glu Lys Gln Val Thr Ile Cys
            35                  40                  45

Cys Gln Gly Asn Tyr Gly Ala Val Glu Tyr Gln Leu His Phe Glu Gly
        50                  55                  60

Ser Leu Phe Ala Val Asp Arg Pro Lys Pro Glu Arg Ile Asn Lys
65                  70                  75                  80

Val Lys Phe Tyr Ile Pro Asp Met Asn Ser Arg Met Ala Gly Gln Tyr
                85                  90                  95

Ser Cys Ile Tyr Arg Val Gly Glu Leu Trp Ser Glu Pro Ser Asn Leu
            100                 105                 110

Leu Asp Leu Val Val Thr Glu Met Tyr Asp Thr Pro Thr Leu Ser Val
            115                 120                 125

His Pro Gly Pro Glu Val Ile Ser Gly Glu Lys Val Thr Phe Tyr Cys
        130                 135                 140

Arg Leu Asp Thr Ala Thr Ser Met Phe Leu Leu Leu Lys Glu Gly Arg
145                 150                 155                 160

Ser Ser His Val Gln Arg Gly Tyr Gly Lys Val Gln Ala Glu Phe Pro
                165                 170                 175

Leu Gly Pro Val Thr Thr Ala His Arg Gly Thr Tyr Arg Cys Phe Gly
            180                 185                 190

Ser Tyr Asn Asn His Ala Trp Ser Phe Pro Ser Glu Pro Val Lys Leu
        195                 200                 205

Leu Val Thr Gly Asp Ile Glu Asn Thr Ser Leu Ala Pro Glu Asp Pro
    210                 215                 220

Thr Phe Pro Ala Asp Thr Trp Gly Thr Tyr Leu Leu Thr Thr Glu Thr
225                 230                 235                 240

Gly Leu Gln Lys Asp His Ala Leu Trp Asp His Thr Ala Gln Asn Leu
                245                 250                 255

Leu Arg Met Gly Leu Ala Phe Leu Val Leu Val Ala Leu Val Trp Phe
            260                 265                 270

Leu Val Glu Asp Trp Leu Ser Arg Lys Arg Thr Arg Glu Arg Ala Ser
        275                 280                 285

Arg Ala Ser Thr Trp Glu Gly Arg Arg Arg Leu Asn Thr Gln Thr Leu
    290                 295                 300

Asp Pro Glu Pro Lys Ser Ser Asp Lys Thr His Thr Cys Pro Pro Cys
305                 310                 315                 320

Pro Ala Pro Glu Phe Glu Gly Ala Pro Ser Val Phe Leu Phe Pro Pro
                325                 330                 335

```
Lys Pro Lys Asp Thr Leu Met Ile Ser Arg Thr Pro Glu Val Thr Cys
                340                 345                 350

Val Val Val Asp Val Ser His Glu Asp Pro Glu Val Lys Phe Asn Trp
            355                 360                 365

Tyr Val Asp Gly Val Glu Val His Asn Ala Lys Thr Lys Pro Arg Glu
        370                 375                 380

Glu Gln Tyr Asn Ser Thr Tyr Arg Val Val Ser Val Leu Thr Val Leu
385                 390                 395                 400

His Gln Asp Trp Leu Asn Gly Lys Glu Tyr Lys Cys Lys Val Ser Asn
                405                 410                 415

Lys Ala Leu Pro Ala Pro Ile Glu Lys Thr Ile Ser Lys Ala Lys Gly
            420                 425                 430

Gln Pro Arg Glu Pro Gln Val Tyr Thr Leu Pro Pro Ser Arg Asp Glu
        435                 440                 445

Leu Thr Lys Asn Gln Val Ser Leu Thr Cys Leu Val Lys Gly Phe Tyr
    450                 455                 460

Pro Ser Asp Ile Ala Val Glu Trp Glu Ser Asn Gly Gln Pro Glu Asn
465                 470                 475                 480

Asn Tyr Lys Thr Thr Pro Pro Val Leu Asp Ser Asp Gly Ser Phe Phe
                485                 490                 495

Leu Tyr Ser Lys Leu Thr Val Asp Lys Ser Arg Trp Gln Gln Gly Asn
            500                 505                 510

Val Phe Ser Cys Ser Val Met His Glu Ala Leu His Asn His Tyr Thr
        515                 520                 525

Gln Lys Ser Leu Ser Leu Ser Pro Gly Lys
    530                 535

<210> SEQ ID NO 12
<211> LENGTH: 159
<212> TYPE: PRT
<213> ORGANISM: Artificial Sequence
<220> FEATURE:
<223> OTHER INFORMATION: Synthetic

<400> SEQUENCE: 12

Met Gly Met Pro Met Gly Ser Leu Gln Pro Leu Ala Thr Leu Tyr Leu
1               5                   10                  15

Leu Gly Met Leu Val Ala Ser Cys Leu Gly Arg Leu Arg Val Pro Tyr
            20                  25                  30

Asp Thr Pro Thr Leu Ser Val His Pro Gly Pro Glu Val Ile Ser Gly
        35                  40                  45

Glu Lys Val Thr Phe Tyr Cys Arg Leu Asp Thr Ala Thr Ser Met Phe
    50                  55                  60

Leu Leu Leu Gln Glu Gly Gln Ser Ser Gln Val Gln Gln Gly Tyr Gly
65                  70                  75                  80

Lys Val Gln Ala Glu Phe Pro Leu Gly Pro Val Thr Thr Ala His Arg
                85                  90                  95

Gly Thr Tyr Arg Cys Phe Gly Ser Tyr Asn Asn His Ala Trp Ser Phe
            100                 105                 110

Pro Ser Glu Pro Val Lys Leu Leu Val Thr Gly Asp Ile Glu Asn Thr
        115                 120                 125

Ser Leu Ala Pro Glu Asp Pro Thr Phe Pro Asp Thr Trp Gly Thr Tyr
    130                 135                 140

Leu Leu Thr Thr Glu Thr Gly Leu Gln Lys Asp His Ala Leu Trp
145                 150                 155
```

<210> SEQ ID NO 13
<211> LENGTH: 159
<212> TYPE: PRT
<213> ORGANISM: Artificial Sequence
<220> FEATURE:
<223> OTHER INFORMATION: Synthetic

<400> SEQUENCE: 13

```
Met Gly Met Pro Met Gly Ser Leu Gln Pro Leu Ala Thr Leu Tyr Leu
1               5                   10                  15

Leu Gly Met Leu Val Ala Ser Cys Leu Gly Arg Leu Arg Val Pro Tyr
            20                  25                  30

Asp Thr Pro Thr Leu Ser Val His Pro Gly Pro Glu Val Ile Ser Gly
        35                  40                  45

Glu Lys Val Thr Phe Tyr Cys Arg Leu Asp Thr Ala Thr Ser Met Phe
50                  55                  60

Leu Leu Leu Gln Glu Gly Gln Ser Ser Gln Val Gln Gln Gly Tyr Gly
65                  70                  75                  80

Thr Val Gln Ala Glu Phe Pro Leu Gly Pro Val Thr Thr Ala His Arg
                85                  90                  95

Gly Thr Tyr Arg Cys Phe Gly Ser Tyr Asn Asn His Ala Trp Ser Phe
            100                 105                 110

Pro Ser Glu Pro Val Lys Leu Leu Val Thr Gly Asp Ile Glu Asn Thr
        115                 120                 125

Ser Leu Ala Pro Glu Asp Pro Thr Phe Pro Asp Thr Trp Gly Thr Tyr
    130                 135                 140

Leu Leu Thr Thr Glu Thr Gly Leu Gln Lys Asp His Ala Leu Trp
145                 150                 155
```

<210> SEQ ID NO 14
<211> LENGTH: 159
<212> TYPE: PRT
<213> ORGANISM: Artificial Sequence
<220> FEATURE:
<223> OTHER INFORMATION: Synthetic

<400> SEQUENCE: 14

```
Met Gly Met Pro Met Gly Ser Leu Gln Pro Leu Ala Thr Leu Tyr Leu
1               5                   10                  15

Leu Gly Met Leu Val Ala Ser Cys Leu Gly Arg Leu Arg Val Pro Tyr
            20                  25                  30

Asp Thr Pro Ala Leu Ser Val His Pro Gly Pro Glu Val Ile Ser Gly
        35                  40                  45

Glu Lys Val Thr Phe Tyr Cys Arg Leu Asp Thr Ala Thr Ser Met Phe
50                  55                  60

Leu Leu Leu Lys Glu Gly Arg Ser Ser His Val Gln Arg Gly Tyr Gly
65                  70                  75                  80

Lys Val Gln Ala Glu Phe Pro Leu Gly Pro Val Thr Thr Ala His Arg
                85                  90                  95

Gly Thr Tyr Arg Cys Phe Gly Ser Tyr Asn Asn His Ala Trp Ser Phe
            100                 105                 110

Pro Ser Glu Pro Val Lys Leu Leu Val Thr Gly Asp Ile Glu Asn Thr
        115                 120                 125

Ser Leu Ala Pro Glu Asp Pro Thr Phe Pro Asp Thr Trp Gly Thr Tyr
    130                 135                 140

Leu Leu Thr Thr Glu Thr Gly Leu Gln Lys Asp His Ala Leu Trp
```

<210> SEQ ID NO 15
<211> LENGTH: 159
<212> TYPE: PRT
<213> ORGANISM: Artificial Sequence
<220> FEATURE:
<223> OTHER INFORMATION: Synthetic

<400> SEQUENCE: 15

```
Met Gly Met Pro Met Gly Ser Leu Gln Pro Leu Ala Thr Leu Tyr Leu
1               5                   10                  15

Leu Gly Met Leu Val Ala Ser Cys Leu Gly Arg Leu Arg Val Pro Tyr
            20                  25                  30

Asp Thr Pro Thr Leu Ser Val His Pro Gly Pro Glu Val Ile Ser Gly
        35                  40                  45

Glu Lys Val Thr Phe Tyr Cys Arg Leu Asp Thr Ala Thr Ser Met Phe
    50                  55                  60

Leu Leu Leu Lys Glu Gly Arg Ser Ser His Val Gln Arg Gly Tyr Gly
65                  70                  75                  80

Lys Val Gln Ala Glu Phe Pro Leu Gly Pro Val Thr Thr Ala His Arg
                85                  90                  95

Gly Thr Tyr Arg Cys Phe Gly Ser Tyr Asn Asn His Ala Trp Ser Phe
            100                 105                 110

Pro Ser Glu Pro Val Lys Leu Leu Val Thr Gly Asp Ile Glu Asn Thr
        115                 120                 125

Ser Leu Ala Pro Glu Asp Pro Ala Phe Pro Asp Thr Trp Gly Thr Tyr
    130                 135                 140

Leu Leu Thr Thr Glu Thr Gly Leu Gln Lys Asp His Ala Leu Trp
145                 150                 155
```

<210> SEQ ID NO 16
<211> LENGTH: 159
<212> TYPE: PRT
<213> ORGANISM: Artificial Sequence
<220> FEATURE:
<223> OTHER INFORMATION: Synthetic

<400> SEQUENCE: 16

```
Met Gly Met Pro Met Gly Ser Leu Gln Pro Leu Ala Thr Leu Tyr Leu
1               5                   10                  15

Leu Gly Met Leu Val Ala Ser Cys Leu Gly Arg Leu Arg Val Pro Tyr
            20                  25                  30

Asp Thr Pro Thr Leu Ser Val His Pro Gly Pro Glu Val Ile Ser Gly
        35                  40                  45

Glu Lys Val Thr Phe Tyr Cys Arg Leu Asp Thr Ala Thr Ser Met Phe
    50                  55                  60

Leu Leu Leu Lys Glu Gly Arg Ser Ser His Val Gln Arg Gly Tyr Gly
65                  70                  75                  80

Lys Val Gln Ala Glu Phe Pro Leu Gly Pro Val Thr Thr Ala His Arg
                85                  90                  95

Gly Thr Tyr Arg Cys Phe Gly Ser Tyr Asn Asn His Ala Trp Ser Phe
            100                 105                 110

Pro Ser Glu Pro Val Lys Leu Leu Val Thr Gly Asp Ile Glu Ala Thr
        115                 120                 125

Ser Leu Ala Pro Glu Asp Pro Thr Phe Pro Asp Thr Trp Gly Thr Tyr
    130                 135                 140
```

Leu Leu Thr Thr Glu Thr Gly Leu Gln Lys Asp His Ala Leu Trp
145                 150                 155

<210> SEQ ID NO 17
<211> LENGTH: 393
<212> TYPE: PRT
<213> ORGANISM: Artificial Sequence
<220> FEATURE:
<223> OTHER INFORMATION: Synthetic

<400> SEQUENCE: 17

Met Gly Met Pro Met Gly Ser Leu Gln Pro Leu Ala Thr Leu Tyr Leu
1               5                   10                  15

Leu Gly Met Leu Val Ala Ser Cys Leu Gly Arg Leu Arg Val Pro Tyr
            20                  25                  30

Asp Thr Pro Thr Leu Ser Val His Pro Gly Pro Glu Val Ile Ser Gly
            35                  40                  45

Glu Lys Val Thr Phe Tyr Cys Arg Leu Asp Thr Ala Thr Ser Met Phe
50                  55                  60

Leu Leu Leu Lys Glu Gly Arg Ser Ser His Val Gln Arg Gly Tyr Gly
65                  70                  75                  80

Lys Val Gln Ala Glu Phe Pro Leu Gly Pro Val Thr Thr Ala His Arg
                85                  90                  95

Gly Thr Tyr Arg Cys Phe Gly Ser Tyr Asn Asn His Ala Trp Ser Phe
            100                 105                 110

Pro Ser Glu Pro Val Lys Leu Leu Val Thr Gly Asp Ile Glu Asn Thr
        115                 120                 125

Ser Leu Ala Pro Glu Asp Pro Thr Phe Pro Asp Thr Trp Gly Thr Tyr
130                 135                 140

Leu Leu Thr Thr Glu Thr Gly Leu Gln Lys Asp His Ala Leu Trp Asp
145                 150                 155                 160

Pro Glu Pro Lys Ser Ser Asp Lys Thr His Thr Cys Pro Pro Cys Pro
                165                 170                 175

Ala Pro Glu Phe Glu Gly Ala Pro Ser Val Phe Leu Phe Pro Pro Lys
            180                 185                 190

Pro Lys Asp Thr Leu Met Ile Ser Arg Thr Pro Glu Val Thr Cys Val
        195                 200                 205

Val Val Asp Val Ser His Glu Asp Pro Glu Val Lys Phe Asn Trp Tyr
210                 215                 220

Val Asp Gly Val Glu Val His Asn Ala Lys Thr Lys Pro Arg Glu Glu
225                 230                 235                 240

Gln Tyr Asn Ser Thr Tyr Arg Val Val Ser Val Leu Thr Val Leu His
                245                 250                 255

Gln Asp Trp Leu Asn Gly Lys Glu Tyr Lys Cys Lys Val Ser Asn Lys
            260                 265                 270

Ala Leu Pro Ala Pro Ile Glu Lys Thr Ile Ser Lys Ala Lys Gly Gln
        275                 280                 285

Pro Arg Glu Pro Gln Val Tyr Thr Leu Pro Pro Ser Arg Asp Glu Leu
290                 295                 300

Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
                325                 330                 335

Tyr Lys Thr Thr Pro Pro Val Leu Asp Ser Asp Gly Ser Phe Phe Leu
            340                 345                 350

Tyr Ser Lys Leu Thr Val Asp Lys Ser Arg Trp Gln Gln Gly Asn Val
                355                 360                 365

Phe Ser Cys Ser Val Met His Glu Ala Leu His Asn His Tyr Thr Gln
        370                 375                 380

Lys Ser Leu Ser Leu Ser Pro Gly Lys
385                 390

<210> SEQ ID NO 18
<211> LENGTH: 393
<212> TYPE: PRT
<213> ORGANISM: Artificial Sequence
<220> FEATURE:
<223> OTHER INFORMATION: Synthetic

<400> SEQUENCE: 18

Met Gly Met Pro Met Gly Ser Leu Gln Pro Leu Ala Thr Leu Tyr Leu
1               5                   10                  15

Leu Gly Met Leu Val Ala Ser Cys Leu Gly Arg Leu Arg Val Pro Tyr
                20                  25                  30

Asp Thr Pro Thr Leu Ser Val His Pro Gly Pro Glu Val Ile Ser Gly
                35                  40                  45

Glu Lys Val Thr Phe Tyr Cys Arg Leu Asp Thr Ala Thr Ser Met Phe
    50                  55                  60

Leu Leu Leu Gln Glu Gly Gln Ser Ser Gln Val Gln Gln Gly Tyr Gly
65                  70                  75                  80

Lys Val Gln Ala Glu Phe Pro Leu Gly Pro Val Thr Thr Ala His Arg
                85                  90                  95

Gly Thr Tyr Arg Cys Phe Gly Ser Tyr Asn Asn His Ala Trp Ser Phe
                100                 105                 110

Pro Ser Glu Pro Val Lys Leu Leu Val Thr Gly Asp Ile Glu Asn Thr
            115                 120                 125

Ser Leu Ala Pro Glu Asp Pro Thr Phe Pro Asp Thr Trp Gly Thr Tyr
    130                 135                 140

Leu Leu Thr Thr Glu Thr Gly Leu Gln Lys Asp His Ala Leu Trp Asp
145                 150                 155                 160

Pro Glu Pro Lys Ser Ser Asp Lys Thr His Thr Cys Pro Pro Cys Pro
                165                 170                 175

Ala Pro Glu Phe Glu Gly Ala Pro Ser Val Phe Leu Phe Pro Pro Lys
            180                 185                 190

Pro Lys Asp Thr Leu Met Ile Ser Arg Thr Pro Glu Val Thr Cys Val
        195                 200                 205

Val Val Asp Val Ser His Glu Asp Pro Glu Val Lys Phe Asn Trp Tyr
    210                 215                 220

Val Asp Gly Val Glu Val His Asn Ala Lys Thr Lys Pro Arg Glu Glu
225                 230                 235                 240

Gln Tyr Asn Ser Thr Tyr Arg Val Val Ser Val Leu Thr Val Leu His
                245                 250                 255

Gln Asp Trp Leu Asn Gly Lys Glu Tyr Lys Cys Lys Val Ser Asn Lys
            260                 265                 270

Ala Leu Pro Ala Pro Ile Glu Lys Thr Ile Ser Lys Ala Lys Gly Gln
        275                 280                 285

Pro Arg Glu Pro Gln Val Tyr Thr Leu Pro Pro Ser Arg Asp Glu Leu
    290                 295                 300

Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
            325                 330                 335

Tyr Lys Thr Thr Pro Pro Val Leu Asp Ser Asp Gly Ser Phe Phe Leu
            340                 345                 350

Tyr Ser Lys Leu Thr Val Asp Lys Ser Arg Trp Gln Gln Gly Asn Val
        355                 360                 365

Phe Ser Cys Ser Val Met His Glu Ala Leu His Asn His Tyr Thr Gln
    370                 375                 380

Lys Ser Leu Ser Leu Ser Pro Gly Lys
385                 390

<210> SEQ ID NO 19
<211> LENGTH: 393
<212> TYPE: PRT
<213> ORGANISM: Artificial Sequence
<220> FEATURE:
<223> OTHER INFORMATION: Synthetic

<400> SEQUENCE: 19

Met Gly Met Pro Met Gly Ser Leu Gln Pro Leu Ala Thr Leu Tyr Leu
1               5                   10                  15

Leu Gly Met Leu Val Ala Ser Cys Leu Gly Arg Leu Arg Val Pro Tyr
            20                  25                  30

Asp Thr Pro Thr Leu Ser Val His Pro Gly Pro Glu Val Ile Ser Gly
        35                  40                  45

Glu Lys Val Thr Phe Tyr Cys Arg Leu Asp Thr Ala Thr Ser Met Phe
    50                  55                  60

Leu Leu Leu Gln Glu Gly Gln Ser Ser Gln Val Gln Gln Gly Tyr Gly
65                  70                  75                  80

Thr Val Gln Ala Glu Phe Pro Leu Gly Pro Val Thr Thr Ala His Arg
                85                  90                  95

Gly Thr Tyr Arg Cys Phe Gly Ser Tyr Asn Asn His Ala Trp Ser Phe
            100                 105                 110

Pro Ser Glu Pro Val Lys Leu Leu Val Thr Gly Asp Ile Glu Asn Thr
        115                 120                 125

Ser Leu Ala Pro Glu Asp Pro Thr Phe Pro Asp Thr Trp Gly Thr Tyr
    130                 135                 140

Leu Leu Thr Thr Glu Thr Gly Leu Gln Lys Asp His Ala Leu Trp Asp
145                 150                 155                 160

Pro Glu Pro Lys Ser Ser Asp Lys Thr His Thr Cys Pro Pro Cys Pro
                165                 170                 175

Ala Pro Glu Phe Glu Gly Ala Pro Ser Val Phe Leu Phe Pro Pro Lys
            180                 185                 190

Pro Lys Asp Thr Leu Met Ile Ser Arg Thr Pro Glu Val Thr Cys Val
        195                 200                 205

Val Val Asp Val Ser His Glu Asp Pro Glu Val Lys Phe Asn Trp Tyr
    210                 215                 220

Val Asp Gly Val Glu Val His Asn Ala Lys Thr Lys Pro Arg Glu Glu
225                 230                 235                 240

Gln Tyr Asn Ser Thr Tyr Arg Val Val Ser Val Leu Thr Val Leu His
                245                 250                 255

Gln Asp Trp Leu Asn Gly Lys Glu Tyr Lys Cys Lys Val Ser Asn Lys
            260                 265                 270

Ala Leu Pro Ala Pro Ile Glu Lys Thr Ile Ser Lys Ala Lys Gly Gln
        275                 280                 285

```
Pro Arg Glu Pro Gln Val Tyr Thr Leu Pro Pro Ser Arg Asp Glu Leu
    290                 295                 300

Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
                325                 330                 335

Tyr Lys Thr Thr Pro Pro Val Leu Asp Ser Asp Gly Ser Phe Phe Leu
                340                 345                 350

Tyr Ser Lys Leu Thr Val Asp Lys Ser Arg Trp Gln Gln Gly Asn Val
                355                 360                 365

Phe Ser Cys Ser Val Met His Glu Ala Leu His Asn His Tyr Thr Gln
370                 375                 380

Lys Ser Leu Ser Leu Ser Pro Gly Lys
385                 390

<210> SEQ ID NO 20
<211> LENGTH: 393
<212> TYPE: PRT
<213> ORGANISM: Artificial Sequence
<220> FEATURE:
<223> OTHER INFORMATION: Synthetic

<400> SEQUENCE: 20

Met Gly Met Pro Met Gly Ser Leu Gln Pro Leu Ala Thr Leu Tyr Leu
1               5                   10                  15

Leu Gly Met Leu Val Ala Ser Cys Leu Gly Arg Leu Arg Val Pro Tyr
                20                  25                  30

Asp Thr Pro Ala Leu Ser Val His Pro Gly Pro Glu Val Ile Ser Gly
                35                  40                  45

Glu Lys Val Thr Phe Tyr Cys Arg Leu Asp Thr Ala Thr Ser Met Phe
50                  55                  60

Leu Leu Leu Lys Glu Gly Arg Ser Ser His Val Gln Arg Gly Tyr Gly
65                  70                  75                  80

Lys Val Gln Ala Glu Phe Pro Leu Gly Pro Val Thr Thr Ala His Arg
                85                  90                  95

Gly Thr Tyr Arg Cys Phe Gly Ser Tyr Asn Asn His Ala Trp Ser Phe
                100                 105                 110

Pro Ser Glu Pro Val Lys Leu Leu Val Thr Gly Asp Ile Glu Asn Thr
                115                 120                 125

Ser Leu Ala Pro Glu Asp Pro Thr Phe Pro Asp Thr Trp Gly Thr Tyr
130                 135                 140

Leu Leu Thr Thr Glu Thr Gly Leu Gln Lys Asp His Ala Leu Trp Asp
145                 150                 155                 160

Pro Glu Pro Lys Ser Ser Asp Lys Thr His Thr Cys Pro Pro Cys Pro
                165                 170                 175

Ala Pro Glu Phe Glu Gly Ala Pro Ser Val Phe Leu Phe Pro Pro Lys
                180                 185                 190

Pro Lys Asp Thr Leu Met Ile Ser Arg Thr Pro Glu Val Thr Cys Val
                195                 200                 205

Val Val Asp Val Ser His Glu Asp Pro Glu Val Lys Phe Asn Trp Tyr
210                 215                 220

Val Asp Gly Val Glu Val His Asn Ala Lys Thr Lys Pro Arg Glu Glu
225                 230                 235                 240

Gln Tyr Asn Ser Thr Tyr Arg Val Val Ser Val Leu Thr Val Leu His
                245                 250                 255
```

Gln Asp Trp Leu Asn Gly Lys Glu Tyr Lys Cys Lys Val Ser Asn Lys
         260                 265                 270

Ala Leu Pro Ala Pro Ile Glu Lys Thr Ile Ser Lys Ala Lys Gly Gln
    275                 280                 285

Pro Arg Glu Pro Gln Val Tyr Thr Leu Pro Pro Ser Arg Asp Glu Leu
290                 295                 300

Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
                325                 330                 335

Tyr Lys Thr Thr Pro Pro Val Leu Asp Ser Asp Gly Ser Phe Phe Leu
            340                 345                 350

Tyr Ser Lys Leu Thr Val Asp Lys Ser Arg Trp Gln Gln Gly Asn Val
        355                 360                 365

Phe Ser Cys Ser Val Met His Glu Ala Leu His Asn His Tyr Thr Gln
370                 375                 380

Lys Ser Leu Ser Leu Ser Pro Gly Lys
385                 390

<210> SEQ ID NO 21
<211> LENGTH: 393
<212> TYPE: PRT
<213> ORGANISM: Artificial Sequence
<220> FEATURE:
<223> OTHER INFORMATION: Synthetic

<400> SEQUENCE: 21

Met Gly Met Pro Met Gly Ser Leu Gln Pro Leu Ala Thr Leu Tyr Leu
1               5                   10                  15

Leu Gly Met Leu Val Ala Ser Cys Leu Gly Arg Leu Arg Val Pro Tyr
            20                  25                  30

Asp Thr Pro Thr Leu Ser Val His Pro Gly Pro Glu Val Ile Ser Gly
        35                  40                  45

Glu Lys Val Thr Phe Tyr Cys Arg Leu Asp Thr Ala Thr Ser Met Phe
    50                  55                  60

Leu Leu Leu Lys Glu Gly Arg Ser Ser His Val Gln Arg Gly Tyr Gly
65                  70                  75                  80

Lys Val Gln Ala Glu Phe Pro Leu Gly Pro Val Thr Thr Ala His Arg
                85                  90                  95

Gly Thr Tyr Arg Cys Phe Gly Ser Tyr Asn Asn His Ala Trp Ser Phe
            100                 105                 110

Pro Ser Glu Pro Val Lys Leu Leu Val Thr Gly Asp Ile Glu Asn Thr
        115                 120                 125

Ser Leu Ala Pro Glu Asp Pro Ala Phe Pro Asp Thr Trp Gly Thr Tyr
    130                 135                 140

Leu Leu Thr Thr Glu Thr Gly Leu Gln Lys Asp His Ala Leu Trp Asp
145                 150                 155                 160

Pro Glu Pro Lys Ser Ser Asp Lys Thr His Thr Cys Pro Pro Cys Pro
                165                 170                 175

Ala Pro Glu Phe Glu Gly Ala Pro Ser Val Phe Leu Phe Pro Pro Lys
            180                 185                 190

Pro Lys Asp Thr Leu Met Ile Ser Arg Thr Pro Glu Val Thr Cys Val
        195                 200                 205

Val Val Asp Val Ser His Glu Asp Pro Glu Val Lys Phe Asn Trp Tyr
    210                 215                 220

Val Asp Gly Val Glu Val His Asn Ala Lys Thr Lys Pro Arg Glu Glu
225                 230                 235                 240

Gln Tyr Asn Ser Thr Tyr Arg Val Val Ser Val Leu Thr Val Leu His
            245                 250                 255

Gln Asp Trp Leu Asn Gly Lys Glu Tyr Lys Cys Lys Val Ser Asn Lys
        260                 265                 270

Ala Leu Pro Ala Pro Ile Glu Lys Thr Ile Ser Lys Ala Lys Gly Gln
    275                 280                 285

Pro Arg Glu Pro Gln Val Tyr Thr Leu Pro Pro Ser Arg Asp Glu Leu
290                 295                 300

Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
            325                 330                 335

Tyr Lys Thr Thr Pro Pro Val Leu Asp Ser Asp Gly Ser Phe Phe Leu
        340                 345                 350

Tyr Ser Lys Leu Thr Val Asp Lys Ser Arg Trp Gln Gln Gly Asn Val
    355                 360                 365

Phe Ser Cys Ser Val Met His Glu Ala Leu His Asn His Tyr Thr Gln
370                 375                 380

Lys Ser Leu Ser Leu Ser Pro Gly Lys
385                 390

<210> SEQ ID NO 22
<211> LENGTH: 393
<212> TYPE: PRT
<213> ORGANISM: Artificial Sequence
<220> FEATURE:
<223> OTHER INFORMATION: Synthetic

<400> SEQUENCE: 22

Met Gly Met Pro Met Gly Ser Leu Gln Pro Leu Ala Thr Leu Tyr Leu
1               5                   10                  15

Leu Gly Met Leu Val Ala Ser Cys Leu Gly Arg Leu Arg Val Pro Tyr
            20                  25                  30

Asp Thr Pro Thr Leu Ser Val His Pro Gly Pro Glu Val Ile Ser Gly
        35                  40                  45

Glu Lys Val Thr Phe Tyr Cys Arg Leu Asp Thr Ala Thr Ser Met Phe
    50                  55                  60

Leu Leu Leu Lys Glu Gly Arg Ser Ser His Val Gln Arg Gly Tyr Gly
65                  70                  75                  80

Lys Val Gln Ala Glu Phe Pro Leu Gly Pro Val Thr Thr Ala His Arg
                85                  90                  95

Gly Thr Tyr Arg Cys Phe Gly Ser Tyr Asn Asn His Ala Trp Ser Phe
            100                 105                 110

Pro Ser Glu Pro Val Lys Leu Leu Val Thr Gly Asp Ile Glu Ala Thr
        115                 120                 125

Ser Leu Ala Pro Glu Asp Pro Thr Phe Pro Asp Thr Trp Gly Thr Tyr
    130                 135                 140

Leu Leu Thr Thr Glu Thr Gly Leu Gln Lys Asp His Ala Leu Trp Asp
145                 150                 155                 160

Pro Glu Pro Lys Ser Ser Asp Lys Thr His Thr Cys Pro Pro Cys Pro
                165                 170                 175

Ala Pro Glu Phe Glu Gly Ala Pro Ser Val Phe Leu Phe Pro Pro Lys
            180                 185                 190

```
Pro Lys Asp Thr Leu Met Ile Ser Arg Thr Pro Glu Val Thr Cys Val
            195                 200                 205

Val Val Asp Val Ser His Glu Asp Pro Glu Val Lys Phe Asn Trp Tyr
        210                 215                 220

Val Asp Gly Val Glu Val His Asn Ala Lys Thr Lys Pro Arg Glu Glu
225                 230                 235                 240

Gln Tyr Asn Ser Thr Tyr Arg Val Val Ser Val Leu Thr Val Leu His
                245                 250                 255

Gln Asp Trp Leu Asn Gly Lys Glu Tyr Lys Cys Lys Val Ser Asn Lys
            260                 265                 270

Ala Leu Pro Ala Pro Ile Glu Lys Thr Ile Ser Lys Ala Lys Gly Gln
        275                 280                 285

Pro Arg Glu Pro Gln Val Tyr Thr Leu Pro Pro Ser Arg Asp Glu Leu
    290                 295                 300

Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
                325                 330                 335

Tyr Lys Thr Thr Pro Pro Val Leu Asp Ser Asp Gly Ser Phe Phe Leu
            340                 345                 350

Tyr Ser Lys Leu Thr Val Asp Lys Ser Arg Trp Gln Gln Gly Asn Val
        355                 360                 365

Phe Ser Cys Ser Val Met His Glu Ala Leu His Asn His Tyr Thr Gln
    370                 375                 380

Lys Ser Leu Ser Leu Ser Pro Gly Lys
385                 390

<210> SEQ ID NO 23
<211> LENGTH: 1197
<212> TYPE: DNA
<213> ORGANISM: Artificial Sequence
<220> FEATURE:
<223> OTHER INFORMATION: Synthetic

<400> SEQUENCE: 23
aagcttgccg ccaccatggg aatgcccatg ggtctctgc aaccgctggc caccttgtac      60
ctgctgggga tgctggtcgc ttcctgcctc ggacggctca gggtacccta tgacacaccc     120
accctctcgg ttcatcctgg acccgaggtg atctcgggag agaaggtgac cttctactgc     180
cgtctagaca ctgcaacaag catgttctta ctgctcaagg agggaagatc cagccacgta     240
cagcgcggat acgggaaggt ccaggcggag ttccccctgg gcctgtgac acagccccac     300 cgagggacat accgatgttt tggctcctat aacaaccatg cctggtcttt ccccagtgag     360
ccagtgaagc tcctggtcac aggcgacatt gagaacacca gccttgcacc tgaagacccc     420
acctttcctg acacttgggg cacctacctt ttaaccacag agacgggact ccagaaagac     480
catgccctct gggatccgga gcccaaatct tctgacaaaa ctcacacatg cccaccgtgc     540
ccagcacctg aattcgaggg tgcaccgtca gtcttcctct tccccccaaa acccaaggac     600
accctcatga tctcccggac ccctgaggtc acatgcgtgg tggtggacgt gagccacgaa     660
gaccctgagg tcaagttcaa ctggtacgtg gacggcgtgg aggtgcataa tgccaagaca     720
aagccgcggg aggagcagta caacagcacg taccgtgtgg tcagcgtcct caccgtcctg     780
caccaggact ggctgaatgg caaggagtac aagtgcaagg tctccaacaa agccctccca     840
gcccccatcg agaaaaccat ctccaaagcc aagggcagc ccgagagcc acaggtgtac     900
```

```
accctgcccc catcccggga tgagctgacc aagaaccagg tcagcctgac ctgcctggtc      960
aaaggcttct atcccagcga catcgccgtg gagtgggaga gcaatgggca gccggagaac     1020
aactacaaga ccacgcctcc cgtgctggac tccgacggct ccttcttcct ctacagcaag     1080
ctcaccgtgg acaagagcag gtggcagcag gggaacgtct tctcatgctc cgtgatgcat     1140
gaggctctgc acaaccacta cacgcagaag agcctctccc tgtctccggg taaatga        1197
```

<210> SEQ ID NO 24
<211> LENGTH: 1197
<212> TYPE: DNA
<213> ORGANISM: Artificial Sequence
<220> FEATURE:
<223> OTHER INFORMATION: Synthetic

<400> SEQUENCE: 24

```
aagcttgccg ccaccatggg aatgcccatg gggtctctgc aaccgctggc caccttgtac       60
ctgctgggga tgctggtcgc ttcctgcctc ggacggctca gggtacccta tgacacaccc      120
accctctcgg ttcatcctgg acccgaggtg atctcgggag agaaggtgac cttctactgc      180
cgtctagaca ctgcaacaag catgttctta ctgctccagg agggacaatc cagccaggta      240
cagcagggat acgggaaggt ccaggcgagg ttccccctgg ccctgtgac cacagcccac       300 cgagggacat accgatgttt tggctcctat aacaaccatg cctggtcttt ccccagtgag      360
ccagtgaagc tcctggtcac aggcgacatt gagaacacca gccttgcacc tgaagacccc     420
acctttcctg acacttgggg cacctacctt ttaaccacag agacgggact ccagaaagac     480
catgccctct gggatccgga gcccaaatct tctgacaaaa ctcacacatg cccaccgtgc     540
ccagcacctg aattcgaggg tgcaccgtca gtcttcctct tccccccaaa acccaaggac     600
accctcatga tctcccggac ccctgaggtc acatgcgtgg tggtggacgt gagccacgaa     660
gaccctgagg tcaagttcaa ctggtacgtg gacggcgtgg aggtgcataa tgccaagaca     720
aagccgcggg aggagcagta caacagcacg taccgtgtgg tcagcgtcct caccgtcctg     780
caccaggact ggctgaatgg caaggagtac aagtgcaagg tctccaacaa agccctccca     840
gcccccatcg agaaaaccat ctccaaagcc aagggcagc cccgagagcc acaggtgtac      900
accctgcccc catcccggga tgagctgacc aagaaccagg tcagcctgac ctgcctggtc     960
aaaggcttct atcccagcga catcgccgtg gagtgggaga gcaatgggca gccggagaac    1020
aactacaaga ccacgcctcc cgtgctggac tccgacggct ccttcttcct ctacagcaag    1080
ctcaccgtgg acaagagcag gtggcagcag gggaacgtct tctcatgctc cgtgatgcat    1140
gaggctctgc acaaccacta cacgcagaag agcctctccc tgtctccggg taaatga       1197
```

<210> SEQ ID NO 25
<211> LENGTH: 1197
<212> TYPE: DNA
<213> ORGANISM: Artificial Sequence
<220> FEATURE:
<223> OTHER INFORMATION: Synthetic

<400> SEQUENCE: 25

```
aagcttgccg ccaccatggg aatgcccatg gggtctctgc aaccgctggc caccttgtac       60
ctgctgggga tgctggtcgc ttcctgcctc ggacggctca gggtacccta tgacacaccc      120
accctctcgg ttcatcctgg acccgaggtg atctcgggag agaaggtgac cttctactgc      180
cgtctagaca ctgcaacaag catgttctta ctgctccagg agggacaatc cagccaggta      240
cagcagggat acgggacagt ccaggcgagg ttccccctgg ccctgtgac cacagcccac       300
```

```
cgagggacat accgatgttt tggctcctat aacaaccatg cctggtcttt ccccagtgag    360
ccagtgaagc tcctggtcac aggcgacatt gagaacacca gccttgcacc tgaagacccc    420
acctttcctg acacttgggg cacctacctt ttaaccacag agacgggact ccagaaagac    480
catgccctct gggatccgga gcccaaatct tctgacaaaa ctcacacatg cccaccgtgc    540
ccagcacctg aattcgaggg tgcaccgtca gtcttcctct tccccccaaa acccaaggac    600
accctcatga tctcccggac ccctgaggtc acatgcgtgg tggtggacgt gagccacgaa    660
gaccctgagg tcaagttcaa ctggtacgtg gacggcgtgg aggtgcataa tgccaagaca    720
aagccgcggg aggagcagta caacagcacg taccgtgtgg tcagcgtcct caccgtcctg    780
caccaggact ggctgaatgg caaggagtac aagtgcaagg tctccaacaa agccctccca    840
gcccccatcg agaaaaccat ctccaaagcc aaagggcagc cccgagagcc acaggtgtac    900
accctgcccc catcccggga tgagctgacc aagaaccagg tcagcctgac ctgcctggtc    960
aaaggcttct atcccagcga catcgccgtg gagtgggaga gcaatgggca gccggagaac   1020
aactacaaga ccacgcctcc cgtgctggac tccgacggct ccttcttcct ctacagcaag   1080
ctcaccgtgg acaagagcag gtggcagcag gggaacgtct tctcatgctc cgtgatgcat   1140
gaggctctgc acaaccacta cacgcagaag agcctctccc tgtctccggg taaatga      1197

<210> SEQ ID NO 26
<211> LENGTH: 1197
<212> TYPE: DNA
<213> ORGANISM: Artificial Sequence
<220> FEATURE:
<223> OTHER INFORMATION: Synthetic

<400> SEQUENCE: 26
aagcttgccg ccaccatggg aatgcccatg gggtctctgc aaccgctggc caccttgtac     60
ctgctgggga tgctggtcgc ttcctgcctc ggacggctca gggtacccta tgacacaccc    120
gccctctcgg ttcatcctgg acccgaggtg atctcgggag agaaggtgac cttctactgc    180
cgtctagaca ctgcaacaag catgttctta ctgctcaagg agggaagatc cagccacgta    240
cagcgcggat acgggaaggt ccaggcggag ttccccctgg gcctgtgaca cacagcccac    300
cgagggacat accgatgttt tggctcctat aacaaccatg cctggtcttt ccccagtgag    360
ccagtgaagc tcctggtcac aggcgacatt gagaacacca gccttgcacc tgaagacccc    420
acctttcctg acacttgggg cacctacctt ttaaccacag agacgggact ccagaaagac    480
catgccctct gggatccgga gcccaaatct tctgacaaaa ctcacacatg cccaccgtgc    540
ccagcacctg aattcgaggg tgcaccgtca gtcttcctct tccccccaaa acccaaggac    600
accctcatga tctcccggac ccctgaggtc acatgcgtgg tggtggacgt gagccacgaa    660
gaccctgagg tcaagttcaa ctggtacgtg gacggcgtgg aggtgcataa tgccaagaca    720
aagccgcggg aggagcagta caacagcacg taccgtgtgg tcagcgtcct caccgtcctg    780
caccaggact ggctgaatgg caaggagtac aagtgcaagg tctccaacaa agccctccca    840
gcccccatcg agaaaaccat ctccaaagcc aaagggcagc cccgagagcc acaggtgtac    900
accctgcccc catcccggga tgagctgacc aagaaccagg tcagcctgac ctgcctggtc    960
aaaggcttct atcccagcga catcgccgtg gagtgggaga gcaatgggca gccggagaac   1020
aactacaaga ccacgcctcc cgtgctggac tccgacggct ccttcttcct ctacagcaag   1080
ctcaccgtgg acaagagcag gtggcagcag gggaacgtct tctcatgctc cgtgatgcat   1140
```

```
gaggctctgc acaaccacta cacgcagaag agcctctccc tgtctccggg taaatga        1197
```

<210> SEQ ID NO 27
<211> LENGTH: 1197
<212> TYPE: DNA
<213> ORGANISM: Artificial Sequence
<220> FEATURE:
<223> OTHER INFORMATION: Synthetic

<400> SEQUENCE: 27

```
aagcttgccg ccaccatggg aatgcccatg gggtctctgc aaccgctggc caccttgtac         60
ctgctgggga tgctggtcgc ttcctgcctc ggacggctca ggtacccta tgacacaccc         120
accctctcgg ttcatcctgg acccgaggtg atctcgggag agaaggtgac cttctactgc        180
cgtctagaca ctgcaacaag catgttctta ctgctcaagg agggaagatc cagccacgta        240
cagcgcggat acgggaaggt ccaggcggag ttcccctgg gccctgtgac cacagcccac         300
cgagggacat accgatgttt tggctcctat aacaaccatg cctggtcttt ccccagtgag        360
ccagtgaagc tcctggtcac aggcgacatt gagaacacca gccttgcacc tgaagacccc       420
gcctttcctg acacttgggg cacctacctt ttaaccacag agacgggact ccagaaagac       480
catgccctct gggatccgga gcccaaatct tctgacaaaa ctcacacatg cccaccgtgc        540
ccagcacctg aattcgaggg tgcaccgtca gtcttcctct tccccccaaa acccaaggac        600
accctcatga tctcccggac ccctgaggtc acatgcgtgg tggtggacgt gagccacgaa        660
gaccctgagg tcaagttcaa ctggtacgtg gacggcgtgg aggtgcataa tgccaagaca        720
aagccgcggg aggagcagta caacagcacg taccgtgtgg tcagcgtcct caccgtcctg        780
caccaggact ggctgaatgg caaggagtac aagtgcaagg tctccaacaa agccctccca        840
gcccccatcg agaaaccat ctccaaagcc aagggcagc cccgagagcc acaggtgtac         900
accctgcccc catcccggga tgagctgacc aagaaccagg tcagcctgac ctgcctggtc        960
aaaggcttct atcccagcga catcgccgtg gagtgggaga gcaatgggca gccggagaac       1020
aactacaaga ccacgcctcc cgtgctggac tccgacggct ccttcttcct ctacagcaag       1080
ctcaccgtgg acaagagcag gtggcagcag gggaacgtct tctcatgctc cgtgatgcat       1140
gaggctctgc acaaccacta cacgcagaag agcctctccc tgtctccggg taaatga         1197
```

<210> SEQ ID NO 28
<211> LENGTH: 1197
<212> TYPE: DNA
<213> ORGANISM: Artificial Sequence
<220> FEATURE:
<223> OTHER INFORMATION: Synthetic

<400> SEQUENCE: 28

```
aagcttgccg ccaccatggg aatgcccatg gggtctctgc aaccgctggc caccttgtac         60
ctgctgggga tgctggtcgc ttcctgcctc ggacggctca ggtacccta tgacacaccc         120
accctctcgg ttcatcctgg acccgaggtg atctcgggag agaaggtgac cttctactgc        180
cgtctagaca ctgcaacaag catgttctta ctgctcaagg agggaagatc cagccacgta        240
cagcgcggat acgggaaggt ccaggcggag ttcccctgg gccctgtgac cacagcccac         300
cgagggacat accgatgttt tggctcctat aacaaccatg cctggtcttt ccccagtgag        360
ccagtgaagc tcctggtcac aggcgacatt gaggccacca gccttgcacc tgaagacccc       420
accttcctg acacttgggg cacctacctt ttaaccacag agacgggact ccagaaagac        480
catgccctct gggatccgga gcccaaatct tctgacaaaa ctcacacatg cccaccgtgc        540
```

```
ccagcacctg aattcgaggg tgcaccgtca gtcttcctct tccccccaaa acccaaggac    600
accctcatga tctcccggac ccctgaggtc acatgcgtgg tggtggacgt gagccacgaa    660
gaccctgagg tcaagttcaa ctggtacgtg gacggcgtgg aggtgcataa tgccaagaca    720
aagccgcggg aggagcagta caacagcacg taccgtgtgg tcagcgtcct caccgtcctg    780
caccaggact ggctgaatgg caaggagtac aagtgcaagg tctccaacaa agcccctccca   840 gcccccatcg agaaaaccat ctccaaagcc aagggcagc cccgagagcc acaggtgtac     900
accctgcccc catcccggga tgagctgacc aagaaccagg tcagcctgac ctgcctggtc    960
aaaggcttct atcccagcga catcgccgtg gagtgggaga gcaatgggca gccggagaac   1020
aactacaaga ccacgcctcc cgtgctggac tccgacggct ccttcttcct ctacagcaag   1080
ctcaccgtgg acaagagcag gtggcagcag gggaacgtct tctcatgctc cgtgatgcat   1140
gaggctctgc acaaccacta cacgcagaag agcctctccc tgtctccggg taaatga      1197
```

<210> SEQ ID NO 29
<211> LENGTH: 304
<212> TYPE: PRT
<213> ORGANISM: Artificial Sequence
<220> FEATURE:
<223> OTHER INFORMATION: Synthetic

<400> SEQUENCE: 29

```
Met Ser Ser Thr Leu Pro Ala Leu Leu Cys Val Gly Leu Cys Leu Ser
1               5                   10                  15

Gln Arg Ile Ser Ala Gln Gln Thr Leu Pro Lys Pro Phe Ile Trp
            20                  25                  30

Ala Glu Pro His Phe Met Val Pro Lys Glu Lys Gln Val Thr Ile Cys
        35                  40                  45

Cys Gln Gly Asn Tyr Gly Ala Val Glu Tyr Gln Leu His Phe Glu Gly
    50                  55                  60

Ser Leu Phe Ala Val Asp Arg Pro Lys Pro Pro Glu Arg Ile Asn Lys
65                  70                  75                  80

Val Lys Phe Tyr Ile Pro Asp Met Asn Ser Arg Met Ala Gly Gln Tyr
                85                  90                  95

Ser Cys Ile Tyr Arg Val Gly Glu Leu Trp Ser Glu Pro Ser Asn Leu
            100                 105                 110

Leu Asp Leu Val Val Thr Glu Met Tyr Asp Thr Pro Thr Leu Ser Val
        115                 120                 125

His Pro Gly Pro Glu Val Ile Ser Gly Glu Lys Val Thr Phe Tyr Cys
    130                 135                 140

Arg Leu Asp Thr Ala Thr Ser Met Phe Leu Leu Leu Lys Glu Gly Arg
145                 150                 155                 160

Ser Ser His Val Gln Arg Gly Tyr Gly Lys Val Gln Ala Glu Phe Pro
                165                 170                 175

Leu Gly Pro Val Thr Thr Ala His Arg Gly Thr Tyr Arg Cys Phe Gly
            180                 185                 190

Ser Tyr Asn Asn His Ala Trp Ser Phe Pro Ser Glu Pro Val Lys Leu
        195                 200                 205

Leu Val Thr Gly Asp Ile Glu Asn Thr Ser Leu Ala Pro Glu Asp Pro
    210                 215                 220

Thr Phe Pro Ala Asp Thr Trp Gly Thr Tyr Leu Leu Thr Thr Glu Thr
225                 230                 235                 240

Gly Leu Gln Lys Asp His Ala Leu Trp Asp His Thr Ala Gln Asn Leu
```

245                 250                 255
Leu Arg Met Gly Leu Ala Phe Leu Val Leu Val Ala Leu Val Trp Phe
            260                 265                 270

Leu Val Glu Asp Trp Leu Ser Arg Lys Arg Thr Arg Glu Arg Ala Ser
        275                 280                 285

Arg Ala Ser Thr Trp Glu Gly Arg Arg Leu Asn Thr Gln Thr Leu
        290                 295                 300

<210> SEQ ID NO 30
<211> LENGTH: 287
<212> TYPE: PRT
<213> ORGANISM: Artificial Sequence
<220> FEATURE:
<223> OTHER INFORMATION: Synthetic

<400> SEQUENCE: 30

Met Ser Ser Thr Leu Pro Ala Leu Leu Cys Val Gly Leu Cys Leu Ser
1               5                   10                  15

Gln Arg Ile Ser Ala Gln Gln Thr Leu Pro Lys Pro Phe Ile Trp
            20                  25                  30

Ala Glu Pro His Phe Met Val Pro Lys Glu Lys Gln Val Thr Ile Cys
        35                  40                  45

Cys Gln Gly Asn Tyr Gly Ala Val Glu Tyr Gln Leu His Phe Glu Gly
    50                  55                  60

Ser Leu Phe Ala Val Asp Arg Pro Lys Pro Pro Glu Arg Ile Asn Lys
65                  70                  75                  80

Val Lys Phe Tyr Ile Pro Asp Met Asn Ser Arg Met Ala Gly Gln Tyr
                85                  90                  95

Ser Cys Ile Tyr Arg Val Gly Glu Leu Trp Ser Glu Pro Ser Asn Leu
            100                 105                 110

Leu Asp Leu Val Val Thr Glu Met Tyr Asp Thr Pro Thr Leu Ser Val
        115                 120                 125

His Pro Gly Pro Glu Val Ile Ser Gly Glu Lys Val Thr Phe Tyr Cys
    130                 135                 140

Arg Leu Asp Thr Ala Thr Ser Met Phe Leu Leu Leu Lys Glu Gly Arg
145                 150                 155                 160

Ser Ser His Val Gln Arg Gly Tyr Gly Lys Val Gln Ala Glu Phe Pro
                165                 170                 175

Leu Gly Pro Val Thr Thr Ala His Arg Gly Thr Tyr Arg Cys Phe Gly
            180                 185                 190

Ser Tyr Asn Asn His Ala Trp Ser Phe Pro Ser Glu Pro Val Lys Leu
        195                 200                 205

Leu Val Thr Gly Asp Ile Glu Asn Thr Ser Leu Ala Pro Glu Asp Pro
    210                 215                 220

Thr Phe Pro Asp His Ala Leu Trp Asp His Thr Ala Gln Asn Leu Leu
225                 230                 235                 240

Arg Met Gly Leu Ala Phe Leu Val Leu Val Ala Leu Val Trp Phe Leu
                245                 250                 255

Val Glu Asp Trp Leu Ser Arg Lys Arg Thr Arg Glu Arg Ala Ser Arg
            260                 265                 270

Ala Ser Thr Trp Glu Gly Arg Arg Leu Asn Thr Gln Thr Leu
        275                 280                 285

<210> SEQ ID NO 31
<211> LENGTH: 209
<212> TYPE: PRT

<213> ORGANISM: Artificial Sequence
<220> FEATURE:
<223> OTHER INFORMATION: Synthetic

<400> SEQUENCE: 31

```
Met Ser Ser Thr Leu Pro Ala Leu Leu Cys Val Gly Leu Cys Leu Ser
1               5                   10                  15

Gln Arg Ile Ser Ala Gln Gln Met Tyr Asp Thr Pro Thr Leu Ser
            20                  25                  30

Val His Pro Gly Pro Glu Val Ile Ser Gly Glu Lys Val Thr Phe Tyr
                35                  40                  45

Cys Arg Leu Asp Thr Ala Thr Ser Met Phe Leu Leu Leu Lys Glu Gly
    50                  55                  60

Arg Ser Ser His Val Gln Arg Gly Tyr Gly Lys Val Gln Ala Glu Phe
65              70                  75                  80

Pro Leu Gly Pro Val Thr Thr Ala His Arg Gly Thr Tyr Arg Cys Phe
                85                  90                  95

Gly Ser Tyr Asn Asn His Ala Trp Ser Phe Pro Ser Glu Pro Val Lys
                100                 105                 110

Leu Leu Val Thr Gly Asp Ile Glu Asn Thr Ser Leu Ala Pro Glu Asp
            115                 120                 125

Pro Thr Phe Pro Ala Asp Thr Trp Gly Thr Tyr Leu Leu Thr Thr Glu
    130                 135                 140

Thr Gly Leu Gln Lys Asp His Ala Leu Trp Asp His Thr Ala Gln Asn
145                 150                 155                 160

Leu Leu Arg Met Gly Leu Ala Phe Leu Val Leu Val Ala Leu Val Trp
                165                 170                 175

Phe Leu Val Glu Asp Trp Leu Ser Arg Lys Arg Thr Arg Glu Arg Ala
                180                 185                 190

Ser Arg Ala Ser Thr Trp Glu Gly Arg Arg Arg Leu Asn Thr Gln Thr
            195                 200                 205

Leu
```

<210> SEQ ID NO 32
<211> LENGTH: 192
<212> TYPE: PRT
<213> ORGANISM: Artificial Sequence
<220> FEATURE:
<223> OTHER INFORMATION: Synthetic

<400> SEQUENCE: 32

```
Met Ser Ser Thr Leu Pro Ala Leu Leu Cys Val Gly Leu Cys Leu Ser
1               5                   10                  15

Gln Arg Ile Ser Ala Gln Gln Met Tyr Asp Thr Pro Thr Leu Ser
            20                  25                  30

Val His Pro Gly Pro Glu Val Ile Ser Gly Glu Lys Val Thr Phe Tyr
                35                  40                  45

Cys Arg Leu Asp Thr Ala Thr Ser Met Phe Leu Leu Leu Lys Glu Gly
    50                  55                  60

Arg Ser Ser His Val Gln Arg Gly Tyr Gly Lys Val Gln Ala Glu Phe
65              70                  75                  80

Pro Leu Gly Pro Val Thr Thr Ala His Arg Gly Thr Tyr Arg Cys Phe
                85                  90                  95

Gly Ser Tyr Asn Asn His Ala Trp Ser Phe Pro Ser Glu Pro Val Lys
                100                 105                 110

Leu Leu Val Thr Gly Asp Ile Glu Asn Thr Ser Leu Ala Pro Glu Asp
```

```
                115                 120                 125
Pro Thr Phe Pro Asp His Ala Leu Trp Asp His Thr Ala Gln Asn Leu
        130                 135                 140

Leu Arg Met Gly Leu Ala Phe Leu Val Leu Ala Leu Val Trp Phe
145                 150                 155                 160

Leu Val Glu Asp Trp Leu Ser Arg Lys Arg Thr Arg Glu Arg Ala Ser
                165                 170                 175

Arg Ala Ser Thr Trp Glu Gly Arg Arg Arg Leu Asn Thr Gln Thr Leu
            180                 185                 190

<210> SEQ ID NO 33
<211> LENGTH: 323
<212> TYPE: PRT
<213> ORGANISM: Artificial Sequence
<220> FEATURE:
<223> OTHER INFORMATION: Synthetic

<400> SEQUENCE: 33

Pro Thr Leu Thr Ala Leu Leu Cys Leu Gly Leu Cys Leu Ser Gln Arg
1               5                   10                  15

Ile Asn Thr Glu Lys Glu Thr Leu Pro Lys Pro Ile Ile Trp Ala Lys
            20                  25                  30

Pro Ser Ile Met Val Thr Asn Gly Asn Ser Val Asn Ile Trp Cys Gln
        35                  40                  45

Gly Ala Gln Ser Ala Ser Glu Tyr Gln Leu Tyr Phe Glu Gly Ser Phe
    50                  55                  60

Phe Ala Leu Glu Arg Pro Lys Pro Ser Arg Ser Met Asn Lys Val Arg
65                  70                  75                  80

Phe Phe Ile Ser Gln Met Thr Ser His Thr Ala Gly Ile Tyr Thr Cys
                85                  90                  95

Phe Tyr Gln Ser Gly Glu Leu Trp Ser Lys Ser Ser Asn Pro Leu Lys
            100                 105                 110

Leu Val Val Thr Gly Leu Tyr Asp Thr Pro Asn Leu Trp Val Tyr Pro
        115                 120                 125

Arg Pro Glu Val Thr Leu Gly Glu Asn Val Thr Phe Phe Cys Gln Leu
    130                 135                 140

Lys Thr Ala Thr Ser Lys Phe Phe Leu Leu Lys Glu Arg Gly Ser Asn
145                 150                 155                 160

His Ile Gln Asn Lys Tyr Gly Asn Ile Gln Ala Glu Phe Pro Met Gly
                165                 170                 175

Pro Val Thr Arg Ala His Arg Gly Thr Tyr Arg Cys Phe Gly Ser Tyr
            180                 185                 190

Asn Asp Tyr Ala Trp Ser Phe Pro Ser Glu Pro Val Thr Leu Leu Ile
        195                 200                 205

Thr Gly Gly Val Glu Asn Ser Ser Leu Ala Pro Thr Asp Pro Thr Ser
    210                 215                 220

Ser Leu Asp Tyr Trp Glu Phe Asp Leu Ser Thr Asn Glu Ser Gly Leu
225                 230                 235                 240

Gln Lys Asp Ser Ala Phe Trp Asp His Thr Thr Gln Asn Leu Ile Arg
                245                 250                 255

Ile Gly Leu Ala Cys Ile Ile Leu Ile Thr Leu Val Trp Leu Leu Thr
            260                 265                 270

Glu Asp Trp Leu Ser Lys Arg Lys Asp His Glu Glu Ala Asn Arg Leu
        275                 280                 285

Thr Asn Trp Glu Cys Arg Arg Arg Trp Arg Met Gln His Tyr Phe Glu
```

```
            290                 295                 300
Glu Glu Gln Arg Asn Ala Ile Ser Met Met Glu Leu Lys Ala Thr Pro
305                 310                 315                 320

Gly Ala Leu

<210> SEQ ID NO 34
<211> LENGTH: 325
<212> TYPE: PRT
<213> ORGANISM: Artificial Sequence
<220> FEATURE:
<223> OTHER INFORMATION: Synthetic

<400> SEQUENCE: 34

Met Leu Pro Thr Leu Thr Ala Leu Leu Cys Leu Gly Leu Cys Leu Ser
1               5                   10                  15

Gln Arg Ile Asn Thr Glu Lys Glu Thr Leu Pro Lys Pro Ile Ile Trp
            20                  25                  30

Ala Lys Pro Ser Ile Met Val Thr Asn Gly Asn Ser Val Asn Ile Trp
        35                  40                  45

Cys Gln Gly Ala Gln Ser Ala Ser Glu Tyr Gln Leu Tyr Phe Glu Gly
    50                  55                  60

Ser Phe Phe Ala Leu Glu Arg Pro Lys Pro Ser Arg Ser Met Asn Lys
65                  70                  75                  80

Val Arg Phe Phe Ile Ser Gln Met Thr Ser His Thr Ala Gly Ile Tyr
                85                  90                  95

Thr Cys Phe Tyr Gln Ser Gly Glu Leu Trp Ser Lys Ser Ser Asn Pro
            100                 105                 110

Leu Lys Leu Val Val Thr Gly Leu Tyr Asp Thr Pro Asn Leu Trp Val
        115                 120                 125

Tyr Pro Gln Pro Glu Val Thr Leu Gly Glu Asn Val Thr Phe Phe Cys
    130                 135                 140

Gln Leu Lys Thr Ala Thr Ser Lys Phe Phe Leu Leu Lys Glu Arg Gly
145                 150                 155                 160

Ser Asn His Ile Gln Asn Lys Tyr Gly Asn Ile Gln Ala Glu Phe Pro
                165                 170                 175

Met Gly Pro Val Thr Arg Ala His Arg Gly Thr Tyr Arg Cys Phe Gly
            180                 185                 190

Ser Tyr Asn Asp Tyr Ala Trp Ser Phe Pro Ser Glu Pro Val Thr Leu
        195                 200                 205

Leu Ile Thr Gly Gly Val Glu Asn Ser Ser Leu Ala Pro Thr Asp Pro
    210                 215                 220

Thr Ser Ser Leu Asp Tyr Trp Glu Phe Asp Leu Ser Thr Asn Glu Ser
225                 230                 235                 240

Gly Leu Gln Lys Asp Ser Ala Phe Trp Asp His Thr Thr Gln Asn Leu
                245                 250                 255

Ile Arg Ile Gly Leu Ala Cys Ile Ile Leu Ile Thr Leu Val Trp Leu
            260                 265                 270

Leu Thr Glu Asp Trp Leu Ser Lys Arg Lys Asp His Glu Glu Ala Asn
        275                 280                 285

Arg Leu Thr Asn Trp Glu Cys Arg Arg Arg Trp Arg Met Gln His Tyr
    290                 295                 300

Phe Glu Glu Glu Gln Arg Asn Ala Ile Ser Met Met Glu Leu Lys Ala
305                 310                 315                 320

Thr Pro Gly Ala Leu
                325
```

```
<210> SEQ ID NO 35
<211> LENGTH: 238
<212> TYPE: PRT
<213> ORGANISM: Artificial Sequence
<220> FEATURE:
<223> OTHER INFORMATION: Synthetic

<400> SEQUENCE: 35

Thr Gln Thr Leu Asp Pro Glu Pro Lys Ser Ser Asp Lys Thr His Thr
1               5                   10                  15

Cys Pro Pro Cys Pro Ala Pro Glu Phe Glu Gly Ala Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
            85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
            115                 120                 125

Lys Ala Lys Gly Gln Pro Arg Glu Pro Gln Val Tyr Thr Leu Pro Pro
    130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
            165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
            195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235
```

METHOD OF TREATING TYPE 1 DIABETES BY ADMINISTERING NKP46 POLYPEPTIDE

FIELD OF THE INVENTION

The invention relates to use of the natural cytotoxicity receptor NKp46 for preventing and treating diabetes, including type I diabetes (TID) and type 2 diabetes. In particular, the invention provides compositions comprising a fragment of the extracellular region of NKp46 for preventing the onset and progression of diabetes.

BACKGROUND OF THE INVENTION

Type 1 diabetes (T1D; also known as type 1 diabetes mellitus and immune-mediated diabetes) is a multifactorial autoimmune disease in which insulin-producing beta cells in pancreatic islets are destroyed by autoreactive T cells. Mononuclear cells infiltrate the pancreatic islets of Langerhans during a variable period of clinically silent inflammation (insulitis), and eventually T cells destroy insulin-producing beta cells. Full-blown type 1 diabetes ensues when most beta cells are destroyed and the pancreas ceases to produce enough insulin. Exogenous insulin must then be administered for life. Weeks or months after insulin treatment starts, patients with type I diabetes can experience a variable period of remission, which is thought to result from restored insulin production by residual beta cells. Continued treatment with exogenous insulin is needed to preserve the residual beta cells, which can still naturally modulate glucose metabolism.

Type 2 diabetes is characterized by insulin resistance which may be combined with reduced insulin secretion. The defective responsiveness to insulin is believed to involve the insulin receptor. In the early stage of type 2 diabetes, hyperglycemia can be reversed by a variety of measures and medications that improve insulin sensitivity or reduce glucose production by the liver. As the disease progresses, impairment of insulin secretion occurs, and therapeutic replacement of insulin is often required. Beta cell destruction also occurs in type 2 diabetes, and it has been proposed that one contributing factor is increased beta cell apoptosis (Rhodes Science 2005 Jan. 21; 307(5708):380-4).

A widely used model of autoimmune T1D is the non-obese diabetic (NOD) mouse, which develops diabetes spontaneously after a variable period of insulitis, similarly to human T1D. NOD mice demonstrate insulitis from 4-5 weeks of age, and after a variable period of chronic inflammation, diabetes develops about 10-20 weeks later, with most females diabetic by 30 weeks of age (1, 2). An additional accepted model of experimental autoimmune diabetes in mice is the induction of diabetes by multiple injections of low doses of streptozotocin (LDST) (3, 4). Streptozotocin causes diabetes by direct beta cell cytotoxicity, as well as by initiation of cell mediated autoimmune reaction against beta cells (4, 5). Adoptive transfer of activated splenocytes from LDST-treated mice has been disclosed to induce diabetes in untreated healthy mice (5).

T1D is considered to be a T cell mediated disease. However, several studies suggest that the innate immune system, in particular natural killer (NK) cells, play a role in the pathogenesis of the disease. For example, it has been disclosed that NK cells infiltrate the islets of NOD mice (7), and islet inflammation mediated mainly by NK cells has been reported in human T1D (8). Several alterations in NK cell compartments in patients with T1D have been disclosed, both at the onset of the disease and after long term hyperglycemia (9). Furthermore, the essential role of NK cells in diabetes development was demonstrated in murine models of accelerated T1D (10, 11). Poirot et al., 2004 disclose that the proportion and number of NK cells, and the timing of their entry to the pancreas correlate with the severity of T1D in transgenic NOD mice (10). It has also been disclosed that depletion of NK cells in transgenic NOD mice models of accelerated T1D significantly inhibits diabetes development (10, 11). However, the molecular mechanisms of NK cell involvement in T1D are still unknown.

NK cells play a crucial role in the initial defense against virus-infected cells and cancer cells (12). They interact with antigen presenting cells (APCs), serve as APCs, directly kill hazardous cells and further secrete chemokines and immunomodulatory cytokines such as IFN-γ and TNF-α, which cause T cells to shift into a Th1 phenotype (13, 14).

NK cells recognize target cells through a diverse array of activating receptors and a delicate balance between inhibitory and activating signals tightly regulates their activation (15-17). NK cells have been identified in target organs of patients suffering from autoimmune diseases (18) and they are capable of attacking autologous cells (19-21).

The killing mediated by NK cells involves several activating receptors, such as the natural cytotoxicity receptors (NCRs) NKp30, NKp44 and NKp46, and NKG2D. NKp30, NKp44 and NKp46 are expressed almost exclusively on NK cells, whereas NKG2D is expressed in additional types of lymphocytes such as CD8+ T cells (22). NKp46 is considered to be the most specific NK marker for which an ortholog protein (NCR-1) has been found in mice (23, 24).

Pessino et al., 1998 discloses molecular cloning of NKp46 and its role in mediated cytotoxicity (Pessino et al., J Exp Med 1998; 188:953-960).

Some of the inventors of the present invention have disclosed that soluble NKp46- and NKp44-immunoglobulin (Ig) fusion proteins, but not an NKp30-Ig fusion protein, specifically bind to hemagglutinin of influenza virus and to hemagglutinin-neuraminidase of Sendai virus (29, 45, 46). According to these disclosures, this interaction is functional and can mediate an enhanced killing of infected cells. Furthermore, the enhanced killing can be abolished by antibodies that block either the HA or the receptors NKp46 and NKp44.

The human NKp46 receptor has multiple isoforms including isoform a (GenBank Accession No. CAA04714); isoform b (GenBank Accession No. CAA06872); isoform c (GenBank Accession No. CAA06873), and isoform d (GenBank Accession No. CAA06874). In general the NKp46 receptor comprises two extracellular Ig-like domains of the C2 type, a transmembrane portion and an intracellular segment. The extracellular portion of NKp46 comprises a D1 domain, designated NKp46D1 (corresponding to residues 22-120 of the mature full length protein of isoform a), and a D2 domain, designated NKp46D2, comprising 134 amino acid residues (corresponding to residues 121-254 of the full length protein of isoform a).

PCT Application Publication No. WO 02/08287 of some of the present inventors discloses a targeting complex comprising a target recognition segment comprising one of NKp30, NKp44 and NKp46 or a functional fragment thereof; and an active segment comprising an active substance such as a cytotoxic moiety, an imaging moiety or an Ig fragment. According to the disclosure, fusion proteins containing the extracellular domains NKp30, NKp44 or NKp46 fused to the Fc portion of human IgG1 (termed respectively NKp30-Ig, NKp44-Ig and NKp46-Ig), bind certain tumor cell targets, and NKp46-Ig binds to virus infected cells. Further disclosed are fusion proteins containing either D1 or D2 fused to the Fc portion of human IgG1 (termed respectively NKp46D1-Ig and NKp46D2-Ig), and the observation that D2 is responsible for interaction with viral hemagglutinin.

PCT Application Publication No. WO 2004/053054 of some of the present inventors discloses that an NKp30-Ig conjugate is effective in inducing tumor regression in vivo in cancer bearing nude mice. Further disclosed are pharmaceutical compositions comprising a first segment selected from NKp30, NKp44 and NKp46 or a functional fragment thereof, and a second segment selected from an Ig molecule or a fragment or Fc fragment thereof, for eliminating a tumor or inhibiting growth of a tumor.

PCT Application Publication No. WO 2005/000086 of some of the present inventors discloses isolated peptide fragments comprising glycosylated residues derived from NKp44 and NKp46 that comprise epitopes essential for binding to target cells. According to the disclosure, a linker peptide within the D2 domain of NKp46 designated NKp46LP, which corresponds to residues 215-254 of the full length protein, contains an O-glycosylated threonine residue that is essential for the binding of NKp46 to viral infected cells and to tumor cells. Further disclosed is a linker peptide derived from the extracellular domain of NKp44 which corresponds to residues 136-190 of the full length protein and comprises a hyperglycosylated region comprising at least 14 predicted glycosylation sites that contribute to the efficient binding to viral-infected cells. Further disclosed are isolated peptide fragments of 10-100 amino acids, derived from the aforementioned peptides which retain the biological activity of interest.

PCT Application Publication No. WO 2005/051973 of some of the present inventors discloses peptides derived from NKp46, NKp44 and NKp30 which comprise sulfated polysaccharides and are capable of binding to tumor cells. Specifically disclosed are peptides derived from NKp46 corresponding to residues 153-172 and 153-175 of the full length protein; peptides derived from NKp30 corresponding to residues 57-84 and 57-76 of the full length protein, and a peptide derived from NKp44 corresponding to residues 51-74 of the full length protein U.S. Patent Application Publication No. 2008/0274047 discloses methods of treating immunoproliferative and autoimmune disorders using antibodies which bind NK cell receptors, particularly to deplete cells involved in the immunoproliferative pathology. According to the disclosure, immmunoproliferative disorders which may be treated by the invention include type I diabetes, and the antibody may directed against human NKp46. Further disclosed is that injection of anti-human NKp46 antibodies into transgenic mice expressing human NKp46 resulted in depletion of NK cells in blood, spleen, liver and lung.

U.S. Patent Application Publication No. 2007/0231813 discloses methods and compositions to assess the therapeutic response of a subject to a therapeutic composition comprising an Fc portion, preferably a therapeutic antibody, wherein the therapeutic antibody preferably is not capable of, or is not required to be capable of, depleting target cells. According to the disclosure, the composition may specifically bind an NK receptor inter alia NKp46 and the subject may have juvenile onset diabetes.

U.S. Patent Application Publication No. 2004/0038339 discloses a multifunctional polypeptide comprising (a) a first domain comprising a binding site specifically recognizing an extracellular epitope of the NKG2D receptor complex; and (b) a second domain having receptor or ligand function, wherein said receptor or ligand function may be an antigen binding site of an antibody or fragment thereof directed against inter alia NKp46 which interacts with haemagglutinin (HA) of influenza virus. According to the disclosure, the composition may be used for treating autoimmune diseases, inter alia insulin-dependent diabetes mellitus, wherein elimination of the subpopulation of immune cells that causes the disease is desired.

PCT Application Publication No. WO 02/072631 discloses an MHC molecule construct comprising a carrier molecule having attached thereto one or more MHC molecules, and optionally further comprising one or more biologically active molecules inter alia NKp46. According to the disclosure, the construct may be used for prognosing or diagnosing a disease, or determining the effectiveness of a medicament against a disease, and the disease may be type I diabetes.

PCT Application Publication No. WO 2009/148568 discloses a cellular composition comprising at least about 30% human facilitating cells (hFCs) having a phenotype of CD8+/alpha beta TCR-/delta gamma TCR-/CD56$^{dim/neg}$ and wherein the hFCs optionally further have a phenotype including NKp46+. According to the disclosure, the composition may be used for transplantation into a human subject having a disease inter alia diabetes.

There remains an unmet need for therapeutic methods directed to preventing and inhibiting insulitis and subsequent onset of type I diabetes. The prior art does not teach or suggest using any of NKp46, an isolated fragment of NKp46 or a fusion protein comprising a fragment of NKp46 for suppressing development of type I diabetes.

SUMMARY OF THE INVENTION

The present invention provides methods for preventing and treating diabetes, including type 1 diabetes and type 2 diabetes, the methods comprising use of a soluble fragment derived from the extracellular region of NKp46.

The present invention is based in part on the discovery that the human NKp46 receptor and its murine ortholog NCR-1 specifically recognize both human and murine pancreatic beta cells, and that NK cells degranulate upon interaction with murine beta cells in an NKp46-dependent manner. The present inventors have surprisingly shown, both in NKp46 knockout mice and in the LDST model, that diabetes development is impaired in the absence of NKp46 and that the highest percentage of NK cells in the pancreas is observed at the time when insulitis develops into diabetes (the "pre-diabetic" stage). Furthermore, it is disclosed herein for the first time that injection of NKp46 fusion proteins to female NOD mice, either at the early stage of insulitis or at the late, pre-diabetic stage, almost entirely prevents diabetes development. Experimental results upon which the present invention is based are disclosed in Gur et al., 2010, authored by some of the inventors of the present invention, and published after the priority dates of the present application (Gur et al., The NKp46 activating receptor is essential for diabetes development. Nat Immunol. 2010 February; 11(2):121-8).

Without wishing to be bound by any particular theory or mechanism of action, the efficacy of the methods of the invention may arise from the activity of anti-NKp46 antibodies that are non-depleting for NK cells, but rather cause a systemic down-regulation of NKp46, thus leading to NK cell dysfunction and disruption of the pathologic pathway that leads to diabetes. The anti-NKp46 antibodies may be either those induced in vivo upon administration of NKp46 or manufactured anti-NKp46 antibodies passively administered.

In a first aspect, the invention provides a method for preventing or treating diabetes, the method comprising administering to a subject in need thereof, a therapeutically effective amount of a composition comprising at least one protein and a pharmaceutically acceptable carrier, wherein the protein is selected from the group consisting of: a protein comprising an isolated fragment of the extracellular region of NKp46; an antibody specific for the extracellular region of NKp46, and a combination thereof; thereby preventing or treating diabetes in the subject.

In a particular embodiment, the diabetes is selected from the group consisting of type 1 diabetes and type 2 diabetes.

In a particular embodiment, the NKp46 is human NKp46. In a particular embodiment, the human NKp46 is an isoform selected from the group consisting of isoform a, isoform b, isoform c and isoform d.

In a particular embodiment, the method comprises administering a composition comprising a protein comprising an isolated fragment of the extracellular region of NKp46. In a particular embodiment, the method further comprises detecting the presence of antibodies specific for the extracellular region of NKp46 in a biological fluid sample from the subject, wherein the detecting is carried out following administrating the composition.

In a particular embodiment, the diabetes is type 1 diabetes and the composition comprises a protein comprising an isolated fragment of the extracellular region of NKp46.

In a particular embodiment, the isolated fragment of the extracellular region of NKp46 comprises the D2 domain or a fragment thereof. In a particular embodiment, the isolated fragment of the extracellular region of NKp46 corresponds to the D2 domain or a fragment thereof. In a particular embodiment, the isolated fragment of the extracellular region of NKp46 is substantially devoid of the D1 domain. In a particular embodiment, the isolated fragment comprises the D2 domain or a fragment thereof and is substantially devoid of the D1 domain. In a particular embodiment, the isolated fragment comprises the D2 domain or a fragment thereof, and a fragment of the D1 domain. In a particular embodiment, the D2 domain is selected from the group consisting of SEQ ID NO: 1; SEQ ID NO: 2; SEQ ID NO: 3; SEQ ID NO: 4; SEQ ID NO: 9 and SEQ ID NO: 10. In a particular embodiment, the isolated fragment comprises an amino acid sequence selected from the group consisting of SEQ ID NOS: 1-10. In a particular embodiment, the isolated fragment corresponds to an amino acid sequence selected from the group consisting of SEQ ID NOS: 1-10.

In a particular embodiment, the isolated fragment comprises a D2 domain variant, wherein the variant comprises at least one amino acid substitution in the D2 domain. In a particular embodiment, the amino acid substitution is at a residue that is glycosylated in the wild type NKp46. In a particular embodiment, the amino acid substitution is at a residue selected from the group consisting of threonine 125, threonine 225, lysine 157, lysine 170, arginine 160, arginine 166, histidine 163, asparagine 216, and a combination thereof; wherein the numbers correspond to the residue positions of SEQ ID NO: 29. In a particular embodiment, the amino acid substitution is selected from the group consisting of T125A; T225A; T225S; T225N; N216A, K157Q; R160Q; H163Q; R166Q; K170T and a combination thereof; wherein the numbers correspond to the residue positions of NKp46 of SEQ ID NO: 29. In a particular embodiment, the D2 domain variant is selected from the group consisting of SEQ ID NOS: 12-16.

In a particular embodiment, the protein comprising an isolated fragment of the extracellular region of NKp46 is selected from the group consisting of a fusion protein and a protein conjugate. In a particular embodiment, the fusion protein comprises the D2 domain or a fragment thereof as a first segment, and further comprises at least one heterologous protein as a second segment. In a particular embodiment, the heterologous protein is selected from the group consisting of: an immunoglobulin, a cytokine, an immunomodulatory protein or peptide, an NK receptor other than NKp46, a hormone, a growth factor and fragments thereof. In a particular embodiment, the heterologous protein is an immunoglobulin fragment. In a particular embodiment, the immunoglobulin fragment is the Fc region of IgG1. In a particular embodiment, the Fc region of IgG1 has the sequence of SEQ ID NO: 35.

In a particular embodiment, the fusion protein comprises the D2 domain or a fragment thereof as the first segment, and the Fc region of IgG1 as the second segment. In a particular embodiment, the second segment comprises the amino acid sequence of SEQ ID NO: 35. In a particular embodiment, the D2 domain or fragment thereof is selected from the group consisting of SEQ ID NOS: 1-10. In a particular embodiment, the first segment of the fusion protein is selected from the group consisting of SEQ ID NOS: 1-10. In a particular embodiment, the fusion protein comprises the amino acid sequence of SEQ ID NO: 17. In a particular embodiment, the fusion protein has the amino acid sequence of SEQ ID NO: 17.

In a particular embodiment, the fusion protein comprises a D2 domain variant as the first segment, wherein the variant comprises at least one amino acid substitution in the D2 domain. In a particular embodiment, the fusion protein comprises a D2 domain variant as the first segment, and further comprises the Fc region of IgG1 as the second segment. In a particular embodiment, fusion protein comprising a D2 domain variant is selected from the group consisting of SEQ ID NOS: 18-22.

In a particular embodiment, the fusion protein is encoded by a polynucleotide selected from the group consisting of SEQ ID NOS: 23-28.

In a particular embodiment, the cytokine is selected from the group consisting of IL-2, IL-4 and IL-10. In a particular embodiment, the immunomodulatory protein or peptide is selected from the group consisting of heat shock protein 60 (HSP60) or a fragment thereof, roquinimex, Q fever complement-fixing antigen (QFA), anti-CD3 antibody and a combination thereof.

In a particular embodiment, the NK receptor other than NKp46 is NKG2D.

In a particular embodiment, the hormone is selected from the group consisting of insulin, glucagon and a combination thereof.

In a particular embodiment, the composition for use in the methods of the invention comprises an antibody specific for the extracellular region of NKp46, wherein the antibody is non-depleting for NK cells. In a particular embodiment, the antibody is specific for the D2 domain. In a particular embodiment, the antibody is selected from the group consisting of a monoclonal antibody, a bispecific antibody, a single chain antibody and a humanized antibody. In a particular embodiment, the diabetes is type 1 diabetes and the composition comprises an antibody specific for the extracellular region of NKp46.

In a particular embodiment, the method comprises administering both of a protein comprising an isolated fragment of the extracellular region of NKp46; and an antibody specific for the extracellular region of NKp46. In a particular embodiment, the administering is carried out separately or concurrently.

In a particular embodiment, the method comprises initially administering the composition at a stage of type 1 diabetes selected from the group consisting of pre-insulitis, early insulitis, pre-diabetes and overt diabetes. In a particular embodiment, the method comprises administering the composition at a stage of type 1 diabetes selected from the group consisting of pre-insulitis, early insulitis, pre-diabetes, overt diabetes and a combination thereof.

In a particular embodiment, the method comprises initially administering the composition at a stage of type 2 diabetes selected from the group consisting of hyperinsulinemia, pre-diabetes and overt diabetes. In a particular embodiment, the method comprises administering the composition at a stage of type 2 diabetes selected from the group consisting of hyperinsulinemia, pre-diabetes and overt diabetes.

In a particular embodiment, the administering is carried out following detection of at least one of impaired fasting blood glucose levels and impaired glucose tolerance levels in the subject. In a particular embodiment, the administering is initiated following detection of impaired fasting blood glucose levels in the subject. In a particular embodiment, the administering is initiated following detection of impaired glucose tolerance levels in the subject. In a particular embodiment, the method comprises determination of fasting blood glucose levels and glucose tolerance levels in the subject prior to and subsequent to administering the composition.

In a particular embodiment, the method comprises administration of a single dose of the composition or multiple doses of the composition. In a particular embodiment, the composition is administered at weekly intervals.

In a particular embodiment, the administering is carried out by a route selected from the group consisting of parenteral, oral and transdermal.

In a particular embodiment, the method further comprises administering an immunomodulatory or immunostimulatory agent in conjunction with administering the composition of the invention. In a particular embodiment, the immunomodulatory or immunostimulatory agent is selected from the group consisting of Bacille Calmette-Guérin (BCG), heat shock protein 60 (HSP60) or a fragment thereof, roquinimex, Q fever complement-fixing antigen (QFA), anti-CD3 antibody, α-galactoslyceramide, an adjuvant and a combination thereof. In a particular embodiment, the adjuvant is selected from the group consisting of immune stimulating complexes (ISCOMS), liposomes, lipopolysaccharide, monophosphoryl lipid A, CpG DNA, muramylpeptides and a combination thereof.

In another aspect, the invention provides a protein comprising an isolated fragment of the extracellular region of NKp46 for use in preventing or treating diabetes.

In another aspect, the invention provides an antibody specific for the extracellular region of NKp46 for use in preventing or treating diabetes, wherein the antibody is non-depleting for NK cells.

In another aspect, the invention provides a pharmaceutical composition comprising a protein comprising an isolated fragment of the extracellular region of NKp46 for use in preventing or treating diabetes.

In another aspect, the invention provides a pharmaceutical composition comprising an antibody specific for the extracellular region of NKp46 for use in preventing or treating diabetes, wherein the antibody is non-depleting for NK cells.

It is to be understood explicitly that the scope of the present invention encompasses homologs, analogs, variants and derivatives of the extracellular region of NKp46 or antibodies specific therefor, including shorter and longer proteins and peptides, and those containing one or more amino acid substitutions, non-natural amino acids and synthetic amino acids as are known in the art, with the stipulation that these variants and modifications must preserve the capacity of the present invention to prevent diabetes.

Other objects, features and advantages of the present invention will become clear from the following description and drawings.

BRIEF DESCRIPTION OF THE FIGURES

FIG. 1A summarizes the mean fluorescence intensity (MFI) of cell labeling by each fusion protein.

FIG. 1B summarizes the percentage of beta cells that express ligand for each fusion protein.

FIG. 1C summarizes four beta cell sub-populations (G1, G2, G3 and G4) distinguished with respect to expression of NCR-1 and GLUT-2 ligands.

FIG. 1D shows the flow cytometry gates used to determine the beta cell sub-populations (G1, G2, G3 and G4) represented in FIG. 1C.

FIG. 2A. Flow cytometry analysis of BW and BW cells transfected with NK-p46-CD3ζ, using monoclonal antibody to NKp46 (black outlined histogram). Gray filled histogram is the background secondary antibody staining.

FIG. 2B. IL-2 secretion from BW and BW cells transfected with NK-p46-CD3ζ following 48 hours incubation with beta cells derived from C57BL/6, BALB/c or pre-diabetic female NOD mice, or with control HeLa cells. Values are mean for triplicate samples. Representative of six independent experiments.

FIG. 3A. Paraffin-embedded sections of pancreatic tissues were obtained from a non-diabetic human autopsy and from female NOD and BALB/c mice, stained with NKp46-Ig or NKp46D1-Ig (FP Control). Magnification is ×200 for main images and ×50 for inserts. Results are representative of six independent experiments.

FIG. 3B. Paraffin-embedded sections of pancreatic tissues obtained at the embryonic E20 stage (top; arrows indicated islets) and from female NOD mice at ages of various weeks (w) during the course of diabetes development were stained with NKp46-Ig. Magnification is ×100 for main images and ×50 for inserts. Results are representative of four independent experiments.

FIG. 3C. Salivary glands derived from female NOD and BALB/c mice and stained with NKp46-Ig or NKp46D1-Ig (FP Control). Magnification is ×200 (upper panel), and ×50 (middle and lower panels). Results are representative of three independent experiments.

FIG. 3D. Normal tissues derived from NOD and BALB/c mice and stained with NKp46-Ig. Magnification is ×100 (lung, liver and thyroid), or ×40 (muscle and spleen). Results are representative of three independent experiments.

FIGS. 3E-G. Paraffin-embedded sections of pancreatic tissues derived from BALB/c mice (FIG. 3E), female NOD mice (FIG. 3F) and a non-diabetic human autopsy (FIG. 3G) were incubated with differentially labeled anti-insulin antibody and NKp46-Ig or NKp46D1-Ig (FP Control). Scale bars: 10 µm. Results are representative of four independent experiments.

FIG. 3H. Paraffin-embedded sections of pancreatic tissue derived from BALB/c mice were incubated with differentially labeled anti-insulin antibody, NKp46-Ig, and anti-somatostatin or anti-glucagon antibodies. Results are representative of two independent experiments.

FIG. 3I. Thyroid and spleen tissues from a non-diabetic human autopsy stained with NKp46-Ig, and nuclear staining with the DNA-intercalating dye DAPI. Results are representative of three independent experiments.

FIG. 4A. Enzyme-linked immunosorbent assay of INF-γ secretion by purified NK cells from NCR-1$^{+/gfp}$ mice (KO) or NCR-1$^{gfp/gfp}$ mice (HET) activated with polyinosinic-polycytidylic acid and incubated for 48 hours with beta cells derived from C57BL/6, BALB/c or pre-diabetic female NOD mice. RMS, methylcholanthrene-induced rhabdomyosarcoma cell line (positive control). *$p<0.05$ (Student's t-test).

FIG. 4B. Splenocytic NK cells were co-cultured with various beta cells, YAC-1 and HeLa cells, stained with allophycocyanin conjugated CD107a antibody and gated on NK cells (GFP+/CD3−). Experiment was performed at an effector to target ratio of 1:1. CD107a positive cells are displayed as % of total NK cells. *$p<0.05$.

FIG. 4C. NK cells obtained from pancreatic islets (PNK) or from the pancreatic lymph nodes (PLN NK) of 12 week old pre-diabetic female NOD mice (n=6-7) were stained with allophycocyanin conjugated CD107a antibody and gated on the NCR-1 positive cells. CD107a positive cells are displayed as % of total NK cells. *$p=0.0014$.

FIG. 5A. Kaplan-Meier analysis of development of diabetes in NCR-1$^{+/gfp}$ mice (KO) and NCR-1$^{gfp/gfp}$ mice (WT) after streptozotocin injection (LDST). $P<0.010$ (Log-rank test). Data are representative of three independent experiments.

FIG. 5B. Blood glucose concentrations up to 45 days after the first streptozotocin injection. The dashed line represents glucose levels >250 mg/dl. Data are representative of three independent experiments.

FIG. 5C. Degree of insulitis in NCR-1$^{+/gfp}$ mice (KO) and NCR-1$^{gfp/gfp}$ mice (WT) 16 days after streptozotocin injection (LDST). Pancreatic tissues were evaluated for degree of insulitis calculated as percent of islets per mouse in each stage of insulitis ($p=0.043$ by Pearson's $\chi 2$ test. Data are representative of two independent experiments.

NK cells in the pancreas of female NOD mice (NOD model; FIG. 6A) or NCR-1$^{gfp/gfp}$ mice injected with streptozotocin (LDST model; FIG. 6B) were identified by staining with anti-mouse NCR-1 (NOD model; FIG. 6A) or as GFP-positive cells (LDST model; FIG. 6B). Cells were stained during several stages of insulitis and diabetes development. For each stage lymphocytes were purified from 2-3 pancreatic tissues derived from female NOD mice and NCR-1$^{gfp/gfp}$ mice, except at the embryonic and the pre-insulitis stages for which 8-10 pancreatic tissues were used. The graphs summarize the mean NK cell percentages, obtained from three independent experiments in each model.

FIG. 8A shows CD107a expression of NK cells isolated from NOD splenocytes pre-incubated with serum (horizontal axis) and then incubated with beta cells at an effector:target ratio of 1:1. NK cells were identified by NCR-1 expression. CD107a+ cells are presented as % of total NK cells. **$p<0.05$ (Student's t-test). Data are representative of two independent experiments.

FIG. 8B shows flow cytometry of NK cells derived from splenocytes fusion protein-treated mice (black outlined histogram) or PBS-treated mice (gray filled histograms) at 36 weeks of age and stained with anti-NCR-1. Data are representative of two independent experiments.

FIGS. 8C and 8D. CD107a+ cells among NK cells derived from the splenocytes of 36 week-old PBS- or fusion protein-treated mice, the various NKp46 treated groups and from the PBS group at 36 weeks of age, incubated with beta cells (FIG. 8C) and various target cells (FIG. 8D) at an effector:target ratio of 1:1 and stained with allophycocyanin-conjugated anti-CD107a antibody. Plots are gated on NCR-1 positive cells. CD107a+ cells are displayed as % of total NK cells. **$p<0.001$ (Student's t-test). Data are representative of two independent experiments.

FIG. 9A. Development of diabetes in NOD mice treated with NKp46-Ig (gray filled squares), NCR1-Ig (black filled triangles), CEA-IG (FP control; open circles) or PBS (black filled diamonds) starting at 11-12 weeks (w) of age and continuing to 20 weeks of age (n=8-9 per group). $P<0.001$, NKp46-Ig and NCR1-Ig versus FP control and PBS (Kaplan-Meyer analysis, log-rank test). Data are representative of two independent experiments.

FIG. 9B. NK cells isolated from peripheral blood lymphocytes of 16 week old treated mice (treatment shown on x-axis) and stained with goat anti-mouse NCR-1 antibody. Shown is median fluorescence intensity (MFI) of the NCR1 staining *$p<0.05$ (Student's t-test). Data are representative of two independent experiments.

FIG. 9C. CD107a+ cells among pathogenic NK cells derived from the islets of treated mice and stained with CD107a. Plots are gated on NCR-1+ cells. CD107a+ cells are displayed as % of total NK cells.*$p<0.03$ for CEA-Ig vs. NCR1-Ig, and $p<0.007$ for CEA-Ig vs NKp4-Ig6. (Student's t-test). Data are representative of two independent experiments.

DETAILED DESCRIPTION OF THE INVENTION

Figure 1A:
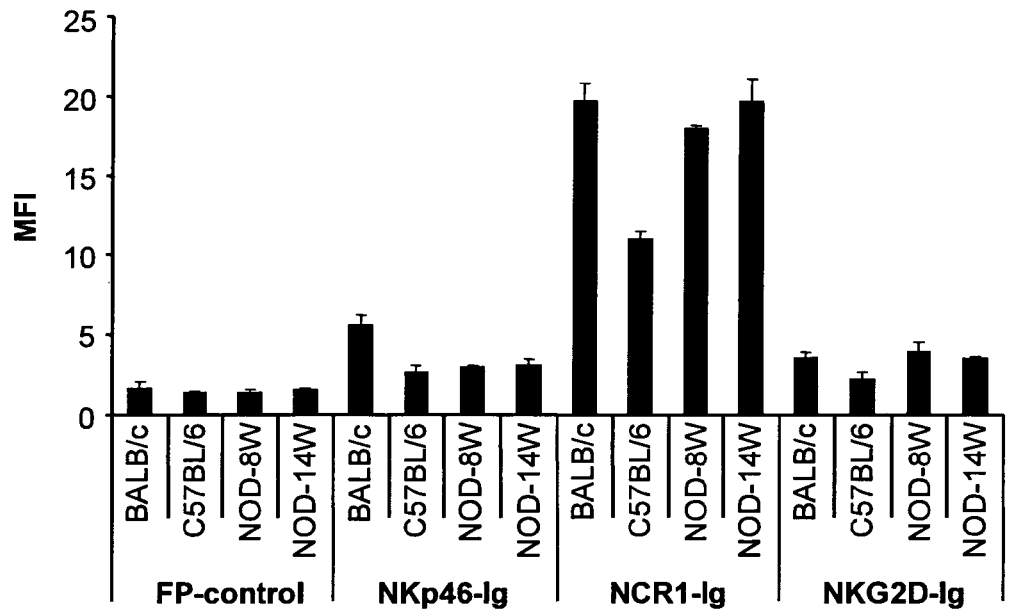
FIGS. 1A-1D show graphical summaries of the labeling of murine beta cells with various fusion proteins, as assessed by fluorescence activated cell sorting (FACS). Beta cells isolated from strains BALB/c, C57BL/6 and NOD, the latter pre-diabetic females of age 8 weeks and 14 weeks (NOD-8W and NOD-14W, respectively) were incubated with fusion proteins CEA-Ig (FP-control), NKp46-Ig, NCR1-Ig or NKG2D-Ig, together with anti-GLUT-2 antibody, the latter of which specifically recognizes beta cells. The graphs are representative of three independent experiments for each system tested.

The present inventors disclose herein for the first time that a fusion protein containing domain D2 of NKp46 fused to the Fc portion of IgG is effective for preventing diabetes type 1, both when administered at the early and late pre-diabetic stage. Furthermore, it is disclosed herein for the first time that in an alternate embodiment diabetes type 1 may be prevented by administration of antibodies specific for the domain D2 of NKp46.

DEFINITIONS

The term "Nkp46" as used herein refers to any human or non-human homolog, ortholog or isoform of the human natural cytotoxicity receptor known as NKp46, including for example those having GenBank Accession Nos. CAA04714; CAA06872; CAA06873; CAA06874; AAH42788 or NP_034876.

The terms "subject" and "patient" as used herein refer to any single subject for whom prevention and/or treatment of diabetes is desired, including humans and non-human mammals, such as primate, bovine, ovine, canine, feline and rodent mammals. Also included are subjects involved in clinical research trials not showing any clinical sign of disease, or subjects involved in epidemiological studies, or subjects used as controls.

The terms "non-depleting antibody" and "non-cytotoxic antibody" interchangeably refer to an antibody which does not substantially kill, destroy or eliminate a cell which bears the specific antigen which is recognized by the particular antibody. It is to be understood that the cell may be that of a unicellular organism, or may be a cell from a multi-celled organism, and encompasses cells substantially isolated from the organism and/or organ of origin.

The singular forms "a", "an", and "the" include plural referents unless the context clearly dictates otherwise. Thus, for example, reference to "an antibody" includes one or more of such antibodies and equivalents thereof known to those skilled in the art, and so forth.

Diabetes

Type 1 diabetes (also known as immune-mediated diabetes) is characterized by loss of the insulin-producing beta cells of the islets of Langerhans in the pancreas leading to insulin deficiency. Type 1 diabetes is associated a T-cell mediated autoimmune attack on beta cells, and there is no known preventive measure for the disease, which causes approximately 10% of diabetes cases in North America and Europe. Most affected people are otherwise healthy and of a healthy weight when onset occurs. Sensitivity and responsiveness to insulin are usually normal, especially in the early stages. Type 1 diabetes can affect children or adults but was traditionally termed "juvenile diabetes" because it represents a majority of the diabetes cases in children.

Type 2 diabetes (formerly called non-insulin-dependent diabetes mellitus (NIDDM), or adult-onset diabetes) is a disorder that is characterized by high blood glucose in the context of insulin resistance and relative insulin deficiency. Risk factors associated with incidence of type 2 diabetes include obesity, hypertension, elevated cholesterol (combined hyperlipidemia), metabolic syndrome and genetic background. Type 2 diabetes accounts for about 90% of diabetes cases in the U.S., and has significantly increased in incidence over the past decades, mainly due to lifestyle factors.

The classical symptoms of diabetes are polyuria (frequent urination), polydipsia (increased thirst) and polyphagia (increased hunger). Symptoms may develop quite rapidly (weeks or months) in type 1 diabetes, particularly in children. However, in type 2 diabetes symptoms usually develop much more slowly and may be subtle or completely absent. Diabetes (both types) may also cause a rapid yet significant weight loss (despite normal or even increased eating) and irreducible mental fatigue.

Patients with type 1 diabetes may also initially present with diabetic ketoacidosis, an extreme state of metabolic dysregulation characterized by the smell of acetone on the patient's breath; a rapid, deep breathing known as Kussmaul breathing; polyuria; nausea; vomiting and abdominal pain; and any of many altered states of consciousness or arousal. In severe cases, coma may follow, progressing to death.

Final diagnosis of both type 1 and type 2 diabetes is made by determination of blood glucose concentrations.

As used herein, the term "overt diabetes" refers to a diagnosis of full-blown diabetes in a subject based on plasma glucose levels, for example, in humans a fasting plasma glucose level ≥7.0 mmol/l (126 mg/dl); or, in an oral glucose tolerance test, two hours after ingestion of an oral dose of 75 g, a plasma glucose level ≥11.1 mmol/l (200 mg/dl); or symptoms of hyperglycemia and casual plasma glucose level ≥11.1 mmol/(200 mg/dl); or the equivalent standards determined for a non-human species. The aforementioned are widely accepted diagnostic criteria for human diabetes (World Health Organization 2006. Definition and diagnosis of diabetes mellitus and intermediate hyperglycemia. Geneva, Switzerland). Glycated hemoglobulin (hemoglobulin A1C) at or above 6.5% may also be considered diagnostic for human diabetes, although it is not uniformly accepted among health policy organizations (Mayfield Diagnosis and Classification of Diabetes Mellitus: New Criteria. Am Fam Physician. 1998 Oct. 15; 58(6):1355-62, 1369-70).

As used herein, the term "pre-diabetes" refers to the occurrence of either or both of impaired fasting glucose and impaired glucose tolerance in a subject. For example in humans, a fasting glucose level from 100 to 125 mg/dL (5.6 to 6.9 mmol/L) is indicative of impaired fasting glucose, and a plasma glucose level at or above 140 mg/dL (7.8 mmol/L), but not over 200 mg/dL (11.1 mmol/L), two hours after a 75 g oral glucose load, is indicative of impaired glucose tolerance. The term also encompasses the equivalent standards determined for a non-human species.

As used herein, the term "hyperinsulinemia" refers to the occurrence of elevated levels of circulating insulin, for example a fasting serum insulin value above about 19 µU/ml for humans, or the equivalent standard determined for a non-human species. Hyperinsulinemia is a marker of insulin resistance, a correlate of the metabolic syndrome, and an established precursor of type 2 diabetes (Carnethon et al., Risk Factors for Progression to Incident Hyperinsulinemia: The Atherosclerosis Risk in Communities Study, 1987-1998).

As used herein, the term "insulitis" refers to the occurrence of lymphocytic infiltration in the islets of Langerhans, such that affected islets have lost most of their beta cell-mass and have only residual beta cells (e.g. less than about 20% of beta cell-mass is retained). Similarly, the terms "pre-insulitis" and "early insulitis" refer to earlier stages of lymphocyte infiltration characterized by a lesser degree of beta cell loss, such that the retained beta cell-mass in pre-insulitis is from about 60 to greater than 80%, and in early insulitis it is about 20 to about 60%.

NKp46 Proteins and Production Thereof.

The terms "protein" and "polypeptide" are used interchangeably herein to refer to polymeric forms of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

A protein of interest or fragment thereof for use in the present invention can be obtained in isolated form by expression of a recombinant nucleic acid encoding the polypeptide or by chemical synthesis. As used herein the term "isolated" is meant to describe a compound of interest (e.g., a polypeptide) that is in an environment different from that in which the compound naturally occurs or was produced. "Isolated" is meant to include compounds that are within samples that are substantially enriched for the compound of interest and/or in which the compound of interest is partially or substantially purified.

As used herein, a "fusion protein" or "chimeric peptide" refers to a protein or polypeptide which comprises a first segment which is a first naturally occurring protein or polypeptide or a fragment thereof, fused to a second segment which is a different protein or polypeptide or a fragment thereof. A fusion protein for use in the invention contains the D2 domain of NKp46 or a ligand binding portion thereof, fused with the Fc region of IgG1, examples of which include SEQ ID NOS: 17-22.

As used herein, a "protein conjugate" or "protein multimer" interchangeably refer to a complex structure of two or more associated polypeptide chains i.e. protein subunits, optionally comprising one or more linkers or spacers. The subunits may be distinct one from the other but also at least some of the subunits may be identical, and the associations between and among the various subunits and linkers may be by covalent, non-covalent, ionic or other types of interactions.

The term "recombinant nucleic acid molecule" as used herein refers to a nucleic acid molecule that is comprised of segments of nucleic acid joined together by means of molecular biological techniques.

The term "recombinant protein" or "recombinant polypeptide" as used herein refers to a protein molecule that is expressed from a recombinant nucleic acid molecule. The NKp46 polypeptide may be the complete extracellular region any of NKp46 protein. The NKp46 polypeptide may include the D1 and D2 domains of the extracellular region, or may be limited to the D2 domain and be substantially devoid of the D1 domain, for example, as in SEQ ID NOS: 1-4, or may include a small portion of D1 and most of D2, for example, as in SEQ ID NO: 5, or may correspond to a relatively short fragment of D2, for example, as in SEQ ID NOS: 6-8.

A D2 domain for use in the invention may be selected from SEQ ID NO: 1; SEQ ID NO: 2; SEQ ID NO: 3; SEQ ID NO: 4; SEQ ID NO: 9 and SEQ ID NO: 10. In particular embodiments, an isolated fragment for use in the invention comprises an amino acid sequence selected from SEQ ID NOS: 1-10.

The polypeptides embraced by the invention also include fusion proteins that contain either the extracellular region or a fragment of it fused to an unrelated amino acid sequence. The unrelated sequences can be additional functional domains or signal peptides. For example, a fusion protein may include the D2 domain or a fragment thereof as a first segment, and at least one heterologous protein as a second segment. Examples of suitable heterologous proteins include immunoglobulins, cytokines, immunomodulatory proteins or peptides, an NK receptor other than NKp46, hormones, growth factors and fragments thereof. In one particular embodiment, the heterologous protein is the Fc region of IgG1.

The polypeptides can also be those with conservative amino acid substitutions, for example one, two, three, four, five, six, seven, eight, nine, 10 or more such substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. The polypeptides can also be those with amino acid deletions or additions, as long as any such mutations do not substantially detract from the ability of the NKp46 protein to function in preventing or treating diabetes, as compared to the corresponding wild type protein.

Amino acid substitutions may be carried out to eliminate glycosylation sites in the D2 domain. Such substitutions are disclosed for example in US Patent Application Publication No. 2007/0203054. Amino acid substitutions may be carried out to eliminate certain ligand binding sites in the D2 domain, such as heparin binding sites. Such substitutions are disclosed for example in WO 2005/051973. The amino acid substitution may be at a residue selected from threonine 125, threonine 225, lysine 157, lysine 170, arginine 160, arginine 166, histidine 163, asparagine 216, or a combination thereof, wherein the numbers correspond to the residue positions of NKp46 of SEQ ID NO: 29. Exemplary amino acid substitution include T125A; T225A; T225S; T225N; K157Q; R160Q; H163Q; R166Q; K170T; N216A and any combination thereof; wherein the numbers correspond to the residue positions of NKp46 of SEQ ID NO: 29. It is to be understood that in the proteins and fragments used for the invention, the amino acid position numbers may differ from the aforementioned, in accordance with the use of sequences that differ from SEQ ID NO: 29, the latter of which corresponds to the full length NKp46 isoform a.

Exemplary NKp46 protein fragments having various amino acid substitutions in the D2 domain variant include SEQ ID NOS: 12-17. In a particular embodiment, the fusion protein comprises a D2 domain variant as the first segment, wherein the variant comprises at least one amino acid substitution in the D2 domain. In a particular embodiment, the fusion protein comprising a D2 domain variant as the first segment, and further comprises the Fc region of IgG1 as the second segment. Fusion proteins comprising a D2 domain variant include those of SEQ ID NOS: 18-22.

The terms "polynucleotide" and "nucleic acid" are used interchangeably herein to refer to polymeric forms of nucleotides of any length, either ribonucleotides or deoxynucleotides, including but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. Further included are mRNA or cDNA that comprise intronic sequences (see, e.g., Niwa et al. (1999) Cell 99(7):691-702). The backbone of the polynucleotide can comprise sugars and phosphate groups (as typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. Peyrottes et al. (1996) Nucl. Acids Res. 24:1841-1848; Chaturvedi et al (1996) Nucl. Acids Res. 24:2318-2323. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component, capping, substitution of one or more of naturally occurring nucleotides with an analog, and introduction of means for attaching the polynucleotide to proteins, metal ions, labeling components, other polynucleotides, or a solid support.

A NKp46 gene or protein can be identified based on its similarity to the relevant NKp46 gene or protein, respectively. For example, the identification can be based on sequence identity. The invention features use of isolated NKp46 D2 domain fragments which are at least 50% (or 60%, 70%, 80%, 90%, 95%, or 98%) identical to the amino acid sequences of SEQ ID NOS: 1-10. Such polypeptides may be produced by recombinant methods using nucleic acids encoding the corresponding polypeptide, or alternately may be extracted from tissues, or chemically produced. The determination of percent identity between two sequences is accomplished using the mathematical algorithm of Karlin and Altschul (1993) Proc. Natl. Acad. Sci. USA 90:5873-5877. Such an algorithm is incorporated into the BLASTN and BLASTP programs of Altschul et al. (1990) J. Mol. Biol. 215, 403-410. BLAST nucleotide searches are performed with the BLASTN program to obtain nucleotide sequences homologous to NKp46 encoding nucleic acids. BLAST protein searches are performed with the BLASTP program to obtain amino acid sequences homologous to the NKp46 polypeptide. To obtain gapped alignments for comparative purposes, Gapped BLAST is utilized as described in Altschul et al (1997) Nucleic Acids Res. 25:3389-3402. When utilizing BLAST and Gapped BLAST programs, the default parameters of the respective programs (e.g., XBLAST and NBLAST) are used.

Hybridization can also be used as a measure of homology between two nucleic acid sequences. An NKp46-encoding nucleic acid sequence, or a portion thereof, can be used as a hybridization probe according to standard hybridization techniques. The hybridization of an NKp46 probe to DNA or RNA from a test source (e.g., a mammalian cell) is an indication of the presence of NKp46 DNA or RNA in the test source. Hybridization conditions are known to those skilled in the art (See, e.g. Current Protocols in Molecular Biology, John Wiley & Sons, N.Y., 6.3.1-6.3.6, (1991)).

Recombinant NKp46 expression vectors that contain a NKp46 D2 domain coding sequence operably linked to transcriptional/translational regulatory elements may be produced. Methods well-known to those skilled in the art can be used to construct such expression vectors (See, for example, Sambrook et al, Molecular Cloning: A Laboratory Manual (2nd Ed.) Cold Spring Harbor Laboratory, N.Y., (1989); and Ausubel et al., Current Protocols in Molecular Biology Green Publishing Associates and Wiley Interscience, N.Y., (1989)).

Nucleic acids encoding NKp46 may be obtained from cells of a human or non-human subject, in particular NK cells, using appropriate oligonucleotide primers and amplification techniques, and the amplified DNA is thereafter ligated into an appropriate expression vector.

The expression vectors may encode, in addition to an NKp46 polypeptide, a second sequence unrelated to NKp46, such as a reporter, a marker, a signal peptide, or a heterologous protein sequence useful for prevention or treatment of diabetes. Recombinant nucleic acid molecules can contain a signal sequence that is the native signal sequence of NKp46 or an heterologous signal sequence. The full length NKp46 polypeptide, or a fragment thereof, may be fused to such signal sequences and/or additional polypeptides. Similarly, the nucleic acid molecules of the invention can encode the mature form of NKp46 or a form that includes an exogenous polypeptide that facilitates secretion.

Accordingly, the nucleic acid encoding NKp46 can form part of a hybrid gene encoding additional polypeptide sequences. Generally, the hybrid gene will encode a polypeptide with a first segment and a second segment; the first segment being a NKp46 fragment and the second portion being for example, an immunoglobulin, a cytokine, an immunomodulatory protein or peptide, an NK receptor other than NKp46, a hormone, a growth factor or a fragment thereof. One example of a suitable the heterologous protein fragment is an immunoglobulin fragment, in particular the Fc region of IgG1. In a particular embodiment, the hybrid gene encodes a fusion protein comprising the D2 domain or a fragment thereof as the first segment, and the Fc region of IgG1 as the second segment. Polynucleotides useful for producing the fusion proteins of the invention include SEQ ID NOS: 23-28.

Expression systems that may be used for production of NKp46 and other recombinant proteins include but are not limited to microorganisms such as bacteria, yeast, plant cell systems, insect cell systems or mammalian cell systems, which may be transformed, infected or transfected, as the case may be, with appropriate recombinant expression vectors or constructs containing the relevant nucleic acid molecule. Also useful as host cells are primary or secondary cells obtained directly from a mammal and transfected with a plasmid vector or infected with a viral vector.

Cells transfected or transduced with such expression vectors can then be used, for example, for large or small scale in vitro production of a NKp46 polypeptide or fragment thereof by methods known in the art. Such methods involve culturing the cells under conditions which maximize production of the polypeptide or antigenic fragment and isolating it from the cells or from the culture medium.

Antibodies

The term "antibody" is used herein in the broadest sense and specifically encompasses monoclonal antibodies, humanized antibodies, polyclonal antibodies, multispecific antibodies (e.g., bispecific antibodies), single chain antibodies and antibody fragments (e.g., F(ab')$_2$, Fab', Fab, Fv) so long as they bind specifically to a target antigen or epitope of interest.

The term "epitope" as used herein refers to that portion of an antigen that is specifically recognized by a particular antibody and makes contact with the antigen binding region of that antibody. When a protein or fragment of a protein is immunogenic in a host animal, numerous regions of the protein may induce the production of antibodies which bind specifically to a given region or three-dimensional structure on the protein; these regions or structures are referred to as "epitopes" or "antigenic determinants". An antigenic determinant may compete with the intact antigen which elicited the immune response, for binding to an antibody. An epitope may itself be a region of an antibody, for example the antigen binding region, or a species-specific Fc region.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries, as is known in the art, for example using techniques such as those described in Clackson et al. (1991) Nature 352:624-628 and Marks et al. (1991) J. Mol. Biol. 222:581-597.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

Chimeric antibodies are typically prepared by splicing the genes (of one species) for an antibody molecule specific for a particular antigen together with genes from another species of antibody molecule of appropriate biological activity. It can be desirable to transfer the antigen binding regions (e.g., Fab', F(ab')$_2$, Fab, Fv, or hypervariable regions) of antibodies from one species into the framework of an antibody from another species by recombinant DNA techniques to produce a chimeric molecule. Methods for producing such molecules are described in, for example, U.S. Pat. Nos. 4,816,567; 4,816,397; 5,693,762, and 5,712,120. A human monoclonal antibody or portion(s) thereof can be identified by screening a human B-cell cDNA library for nucleic acid molecules that encode antibodies that specifically bind to a tumor associated antigen according to the method generally set forth by Huse et al. (Science 246:1275 81 (1989)). The nucleic acid molecule can then be cloned and amplified to obtain sequences that encode the antibody (or antigen-binding domain) of the desired specificity. Phage display technology offers another technique for selecting antibodies that bind to tumor associated antigens, fragments, derivatives or analogs thereof (see, e.g., International Patent Publications WO 91/17271 and WO 92/01047; Huse et al., supra.)

Techniques for the production of single chain antibodies are described for example in U.S. Pat. Nos. 4,946,778 and 5,969,108.

Bi-specific antibodies can be monoclonal antibodies that have binding specificities for at least two different antigens. For example, one of the binding specificities can be for NKp46D2 and the other one is for any other antigen, for example a different NK receptor e.g. NKG2D. Methods of generating bi-specific antibodies are disclosed for example, in Suresh et al (Methods in Enzymology 121:210 (1986)).

Antibodies produced by any method may be purified by known methods, as described for example, in Harlow and Lane, Using Antibodies, A Laboratory Manual, Cold Spring Harbor Laboratory, New York (1999).

The terms "specifically interacts" and "specifically binds" and related grammatical terms are used herein interchangeably to refer to high avidity and/or high affinity binding between an antibody and its epitope. Antibody binding to its epitope is stronger than binding of the same antibody to any other epitope, particularly those which may be present in molecules in association with, or in the same sample, as the specific polypeptide of interest. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g., by use of appropriate controls.

In particular embodiments, the invention involves detection of antibody specific for NKp46 in a biological fluid sample of a subject, following administration to the subject of a composition comprising an isolated protein fragment of the extracellular region of NKp46. In other embodiments, the methods of the invention comprise passive administration of prepared antibodies to the subject.

Biological fluid samples include blood, plasma, serum, saliva, urine, cerebral spinal fluid, semen, tears or mucus. In particular embodiments, the biological fluid sample is plasma or serum.

Preparative samples include those obtained from systems used for antibody production, such as for example, ascites fluid, cell culture supernatants, phage library supernatants and secreted forms thereof.

Immunoassays for detecting specific antibody to NKp46 or specific antibody to D2 of NKp46 (also respectively referred to herein as "anti-NKp46 antibody" and "anti-NKp46D2 antibody") samples are known in the art and may be readily used for detecting antibodies according to the present invention. Suitable immunoassays include for example, radioimmunoassasy, (RIA), fluorescent immunoassays, (FIA), enzyme-linked immunosorbant assays (ELISA), "sandwich" immunoassays, gel diffusion precipitation reactions, immunodiffusion assays, precipitation reactions, agglutination assays and immunoelectrophoresis assays (see for example, Harlow and Lane, Using Antibodies, A Laboratory Manual, Cold Spring Harbor Laboratory, New York (1999)).

Detection of anti-NKp46 antibody can be carried out using surface plasmon resonance, in which NKp46 bound to an appropriate solid substrate is exposed to the sample. Binding of specific antibody to NKp46 on the solid substrate results in a change in the intensity of surface plasmon resonance that can be detected qualitatively or quantitatively by an appropriate instrument, e.g., a Biacore™ apparatus.

Pharmaceutical Compositions and Methods of Administration

For use in the methods of the invention, an NKp46 protein fragment, fusion protein or antibody specific for an NKp46 protein fragment may be formulated in a conventional manner using one or more pharmaceutically acceptable carriers, stabilizers or excipients (vehicles) to form a pharmaceutical composition as is known in the art, in particular with respect to protein active agents. Carrier(s) are "pharmaceutically acceptable" in the sense of being compatible with the other ingredients of the composition and not deleterious to the recipient thereof.

Suitable carriers typically include physiological saline, ethanol polyols such as glycerol or propylene glycol Ringer's solutions, dextrose solution, and Hank's solution. In addition, the pharmaceutical composition or formulation may also include other carriers, adjuvants, or nontoxic, non-therapeutic, non-immunogenic stabilizers and the like. A therapeutically effective dose refers to that amount of protein or its antibodies, which prevent or ameliorate the symptoms of type 1 diabetes. Therapeutic efficacy and toxicity of such compounds can be determined by standard pharmaceutical procedures in cell cultures or experimental animals, e.g., ED50

(the dose therapeutically effective in 50% of the population) and LD50 (the dose lethal to 50% of the population). The dose ratio between therapeutic and toxic effects is the therapeutic index, and it can be expressed as the ratio, LD50/ED50.

Further examples of suitable pharmaceutical carriers are well known in the art and include phosphate buffered saline solutions, water, emulsions, such as oil in water emulsions, various types of wetting agents, sterile solutions etc. Compositions comprising such carriers can be formulated by well known conventional methods.

The protein may be formulated as neutral or salt forms. Pharmaceutically acceptable salts include the acid addition salts (formed with free amino groups) and which are formed with inorganic acids such as hydrochloric or phosphoric acids, or such organic acids such as acetic, oxalic, tartaric and maleic. Salts formed with the free carboxyl groups may also be derived from inorganic bases such as sodium, potassium, ammonium, calcium, or ferric hydroxides, and organic bases as isopropylamine, trimethylamine, 2-ethylamino ethanol, histidine and procaine.

The compositions may be suitably formulated for intravenous, intramuscular, subcutaneous, or intraperitoneal administration and conveniently comprise sterile aqueous solutions of the protein, which are preferably isotonic with the blood of the recipient. Such formulations are typically prepared by dissolving solid active ingredient in water containing physiologically compatible substances such as sodium chloride, glycine, and the like, and having a buffered pH compatible with physiological conditions to produce an aqueous solution, and rendering said solution sterile. These may be prepared in unit or multi-dose containers, for example, sealed ampoules or vials.

The compositions may incorporate a stabilizer, such as for example polyethylene glycol, proteins, saccharides (for example trehalose), amino acids, inorganic acids and admixtures thereof. Stabilizers are used in aqueous solutions at the appropriate concentration and pH. The pH of the aqueous solution is adjusted to be within the range of 5.0-9.0, preferably within the range of 6-8. In formulating the protein, anti-adsorption agent may be used. Other suitable excipients may typically include an antioxidant such as ascorbic acid.

The compositions may be formulated as controlled release preparations which may be achieved through the use of polymer to complex or absorb the proteins. Appropriate polymers for controlled release formulations include for example polyester, polyamino acids, polyvinyl, pyrrolidone, ethylenevinylacetate, and methylcellulose. Another possible method for controlled release is to incorporate the antibody into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly (methylmethacylate) microcapsules, respectively, or in colloidal drug delivery systems, for example, liposomes, albumin microspheres, microemulsions, nanoparticles, and nanocapsules or in macroemulsions.

The composition of the invention may preferably be administered parenterally, such as by injection, intravenous infusion, subcutaneously, intramuscularly or intraperitoneally.

Antibodies are generally administered in the range of about 0.1 to about 20 mg/kg of patient weight, commonly about 0.5 to about 10 mg/kg, and often about 1 to about 5 mg/kg. In this regard, it is preferred to use proteins having a circulating half-life of at least 12 hours, preferably at least 4 days, more preferably up to 21 days. In some cases it may be advantageous to administer a large loading dose followed by periodic (e.g., weekly) maintenance doses over the treatment period. Proteins, including antibodies can be delivered by slow-release delivery systems, pumps, and other known delivery systems for continuous infusion. Dosing regimens may be varied to provide the desired circulating levels of a particular protein based on its pharmacokinetics. Thus, doses will be calculated so that the desired circulating level of therapeutic agent is maintained.

The pharmaceutical compositions for use in the methods of the invention may be alternatively be prepared and administered in formulations suitable for oral, topical or transdermal administration.

When oral preparations are desired, the compositions may be combined with excipients, such as lactose, sucrose, starch, talc magnesium stearate, crystalline cellulose, methyl cellulose, carboxymethyl cellulose, glycerin, sodium alginate or gum arabic.

The pharmaceutical compositions of the invention may be manufactured in a manner which is itself known to one skilled in the art, for example, by means of conventional mixing, granulating, dragee-making, softgel encapsulation, dissolving, extracting, or lyophilizing processes.

Suitable excipients are, in particular, fillers such as saccharides, e.g., lactose or sucrose, mannitol or sorbitol; cellulose preparations and/or calcium phosphates, e.g., tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropymethyl-cellulose phthalate, are used. Dye stuffs or pigments may be added to the tablets or dragee coatings, e.g., for identification or in order to characterize combinations of active compound doses.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

The following methods were employed in the Examples disclosed herein.

Mice.

The generation of NKp46 knockout mice was described previously (23). All experiments were performed in a specific, pathogen-free unit of the Hebrew University Hadassah Medical School (Ein-Kerem, Jerusalem, Israel) in accordance with the guidelines of the local ethical committee.

Cells and Fusion Proteins.

The cell lines used were: HeLa (human cervical carcinoma); BW (murine thymoma) and BW transfectants; RMA-s; PD1.6; YAC-1; RMS (methylcholanthrene-induced rhabdomyosarcoma), and 721.221 (EBV transfected B cell line) and 721.221 CEA transfectant. NCR1-Ig, NKp46-Ig, NCR1-t, NKG2D-Ig, CEA-Ig and NKp46D1-Ig fusion proteins were generated in COS-7 cells and purified on a protein G column, as described (28).

Immunohistochemical and Immunofluorescence Staining.

Paraffin-embedded sections of pancreatic tissues were prepared from non-diabetic human autopsy, from NOD mice embryos (E20), and from 1-14 week old female NOD mice and 8- to 12-week old BALB/c mice. After antigen retrieval, sections were incubated with Ig-fusion proteins for two hours. Sections were then incubated with polyclonal biotin-labeled rabbit anti-human antibody (Jackson ImmunoResearch), directed against the Fcγ portion of the fusion proteins. For immunohistochemical staining, slides were incubated for 30 min with a horseradish peroxidase-labeled polymer conjugated to anti-rabbit (EnVision™; Dako) followed by incubation (1-3 min) with 3,3'diaminobenzidine substrate, and counterstaining with hematoxylin.

For immunofluorescence staining, in addition to incubation with fusion proteins, tissue sections were also incubated with polyclonal anti-mouse insulin (DakoCytomation); anti-somatostatin (Beta Cell Biology Consortium) and anti-glucagon rabbit-anti human antibody and antibodies against insulin, somatostatin and glucagon (Beta Cell Biology Consortium), followed by incubation with the following mixture of three fluorochrome conjugated secondary antibodies: indocarbocyanine-conjugated anti-guinea pig; carbocyanine-conjugated anti-mouse and indodicarbocyanine-conjugated anti-rabbit (all from Jackson ImmunoResearch). As a control, samples were stained with the each fusion protein and all reagent (primary and secondary antibodies) individually. For both the immunohistochemical and the immunofluorescence staining, an NKp46-Ig fusion protein containing only the binding D2 domain and the stalk region of NKp46 was used.

Isolation of Beta Cells; BW Reporter Assay and CD107a Mobilization Assay:

Pancreatic islets from normal and NOD mice were prepared using a solution of collagenase XI (Sigma) diluted in Hank's balanced salt solution (Biological Industries Kibbutz Beit Haemek) at a concentration of 1 mg/ml. The solution was first injected into the pancreatic duct before removal of pancreas, followed by digestion at 37° C. for 15-23 min. Individual islets were selected by hand under a microscope and then separated into single cell solution.

The assay for analysis of cell surface mobilized CD107a has been described previously (31). In some experiments NK cells were pre-incubated for one hour with sera derived from a pool from each group of treated mice, diluted to a titer of 1:10,000.

For measurement of CD107a in vivo, NK cells derived from the islets of beta cells were stained for CD107a expression. For flow cytometry staining, beta cells were stained with 1 μg of biotin-conjugated anti-mouse GLUT-2 (R&D Systems) and with 5 μg of fusion proteins. The generation and use of BW cells expressing NKp46 fused to the transmembrane and tail domains of the mouse CD3 ζ-chain (BW NKp464) has been described (29).

Streptozotocin-Induced Diabetes.

For the multiple LDST model, 10-12 sex- and age-matched mice of 8-10 weeks of age were injected intraperitoneally for 5 consecutive days with streptozotocin (Sigma) dissolved in citrate buffer, pH 4.5, at a concentration of 50 mg/kg. Day 0 was defined as the first day of injection of streptozotocin. Blood glucose concentrations were measured at day 7 and up to 45 days after first injection by using a glucometer (Accu-Chek®, Roche® Diagnostics). Statistical analysis of multiple LDST was performed by Kaplan-Meier analysis with the log-rank test in order to compare survival curves of the two mice groups, and by analysis of variance with repeated measures model for assessment of the time effect, the group effect and the interaction between time and group during diabetes development.

Flow Cytometry Antibodies and Enzyme-Linked Immunosorbent Assay.

Prior to isolation of pancreatic lymphocytes, pancreatic lymph nodes were removed to avoid lymphocyte contamination. Next, pancreatic tissues were cut into 1 mm$^3$ pieces and digested with 1.5 mg type I DNAse and 15 mg type IV collagenase (Sigma). The supernatants were passed through a 40 μm cell strainer and loaded onto a Ficoll density gradient to purify the lymphocyte population. Peripheral blood was obtained from the tail vein. A monoclonal antibody specific for CD16 and CD32 (93, BioLegend®) was used for blocking of Fc receptors before staining. NK cells derived from NOD mice were detected by staining with phytoerythrin-conjugated goat polyclonal antibody to mouse NCR-1 and NKp46 (R&D Systems). For staining of BW cells transfected with/ NKp46, NKp30 or NKp44, 721.221 cells, and 721.221 cells transfected with CEA specific antibodies to NKp46 (BioLegend®), NKp30 (BioLegend®), NKp44 (R&D Systems), and CEA were used (BioLegend®). For staining of BW cells transfected with NCR-1, phytoerythrin-conjugated goat polyclonal antibody to NCR-1 and NKp46 (R&D Systems) was used. For measurement of secretion of mouse IL-2 from the BW transfectants or IFN-γ from mouse NK cells, a standard enzyme linked immunosorbent assay was used with pairs of antibodies to mouse IL-2 (BioLegend®) or IFN-γ (BD Pharmingen)

Example 1

Pancreatic Beta Cells Express Ligand(s) for NKp46

As NKp46 is the only NCR which is expressed in mice, its involvement in murine models for T1D was investigated. Because the cellular ligands for NKp46 and its mouse ortholog NCR-1 are currently unknown, we tested whether NKp46 and NCR-1 would recognize ligand(s) on pancreatic beta cells by using fusion proteins of NKp46 and NCR-1 with immunoglobulin (NKp46-Ig and NCR1-Ig respectively; 23, 29). As negative controls we used the fusion protein NKp46D1-Ig, corresponding to the truncated extracellular portion of NKp46, lacking the ligand binding domain (28), and another irrelevant fusion protein containing the protein carcinoembryonic antigen (CEA-Ig). As a positive control we used the fusion protein NKG2D-Ig.

Figure 1B:
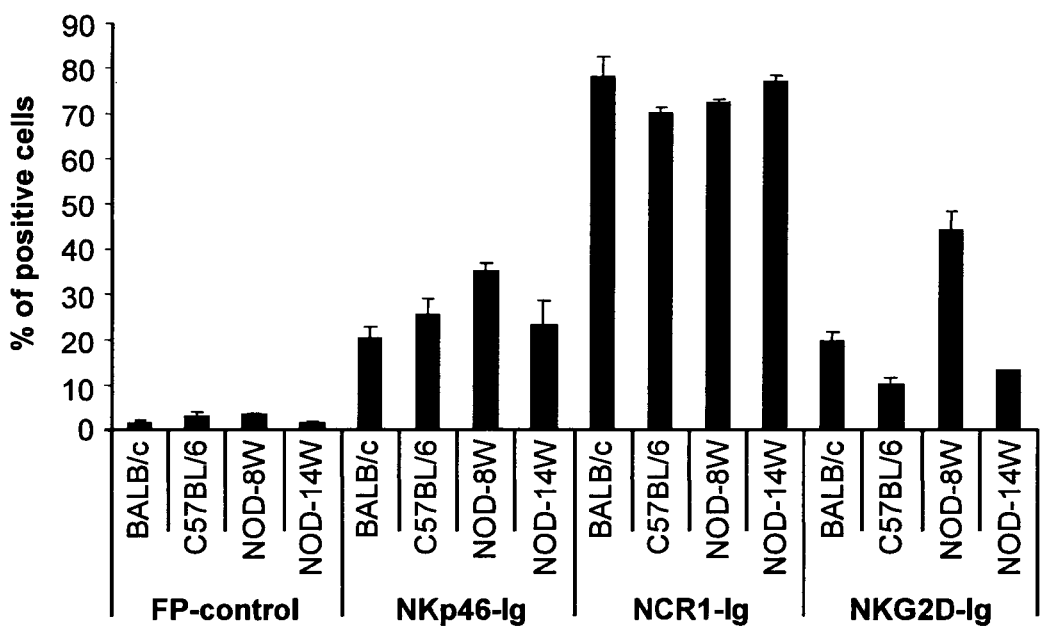

Beta cells isolated from female BALB/c, C57BL/6 and NOD mice were doubly stained with the mouse antibody to GLUT-2 (which specifically labels beta cells) and the various immunoglobulin fusion proteins. Beta cells derived from all murine strains tested were recognized by the mouse NCR-1-Ig and NKp46-Ig fusion proteins, and as expected because of species specificity, the most efficient binding was observed with the mouse NCR1-Ig (FIGS. 1A and 1B). The labeling of beta cells with NKp46-Ig and NCR-1-Ig was specific, as no significant staining was observed with the control fusion protein CEA-Ig (FIGS. 1A and 1B, FP-control), nor with NKp46-D1-Ig. In agreement with previous results demonstrating that NKG2D on CD8+ T cells is involved in beta cell recognition (22, 25), beta cells were recognized by NKG2D-Ig (FIGS. 1A and 1B). However, interestingly, not all beta cells expressed NKG2D ligands and the highest expression of the NKG2D ligands was observed in NOD beta cells (21%, 11%, and 47%, for BALB/c, C57BL/6 and NOD respectively; FIG. 1B). Furthermore, the expression of the NKG2D-ligands was significantly reduced during diabetes progression (47% in 8 week old NOD mice, compared to 13% in the 14 week old mice, FIG. 1B).

Figure 1C:
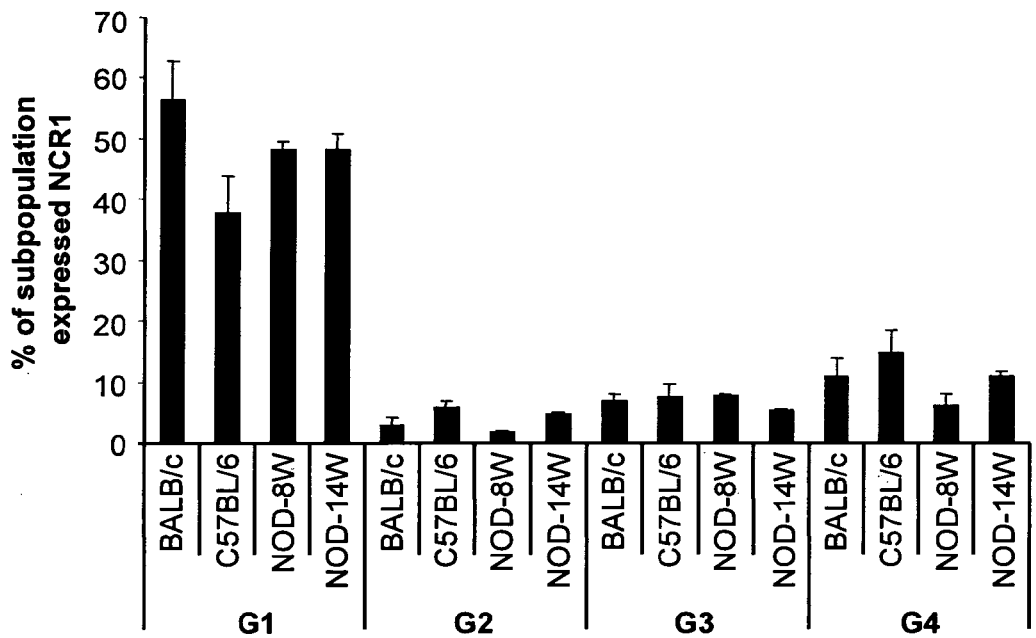
Figure 1D:
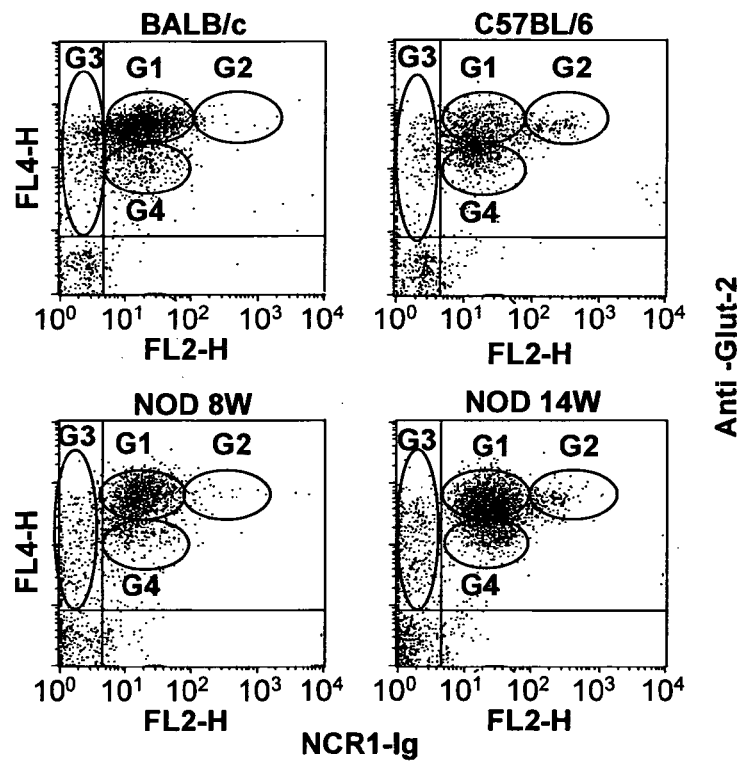

Importantly, most of the beta cells derived from all mice strains were recognized by the NCR1-Ig fusion protein (FIG. 1A). In the beta cells derived from C57BL/6 mice, the intensity of the NCR1-Ig staining was slightly reduced (FIG. 1B) compared to the other strains, and in contrast to the NKG2D ligand expression, the NCR1 ligand expression was constant during diabetes development (FIG. 1B). In this regard, four sub-populations of beta cells could be distinguished (FIG. 1C and FIG. 1D). The G1 subpopulation which comprised most of the beta cells is positive for GLUT-2 and expresses moderate levels of the NCR-1 ligand. The G2 and G4 sub-populations are positive for GLUT-2 (low levels in G4) and express high (G2), or low (G4) levels of ligand for NCR-1. The G3 subpopulation is positive for GLUT-2, and negative for the NCR-1 ligand.

Figure 2A:
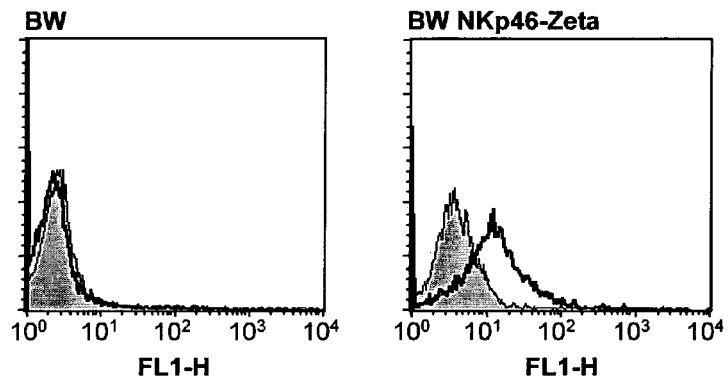
FIGS. 2A-2B show analysis using BW reporter assays.
Figure 2B:
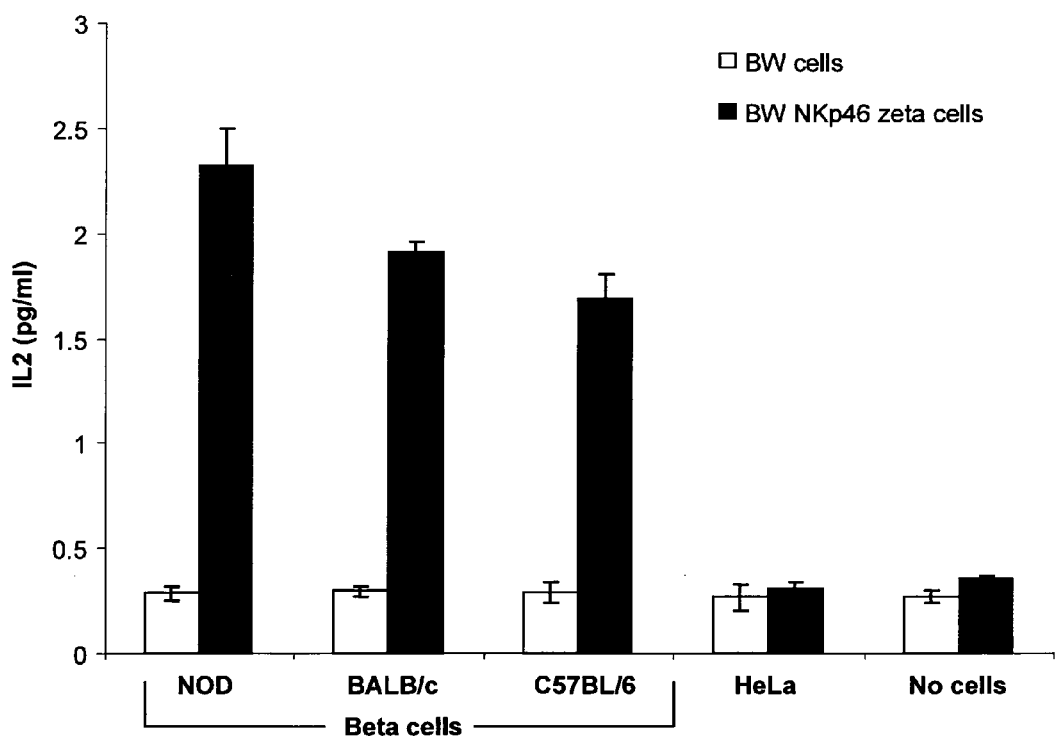

To further confirm that NKp46 recognizes specific beta cell ligands, we used a BW reporter assay previously generated (29). In this system the extracellular portion of NKp46 is fused to the transmembrane and tail domains of mouse CD3 ζ-chain (NK-p46-CD3ζ; FIG. 2A) and thus ligand recognition leads to secretion of mouse IL-2. Substantial secretion of IL-2 was observed in NK-p46-CD3ζ transfected BW cells incubated with beta cells derived from all mouse strains (FIG. 2B). Very low levels of IL-2 secretion were observed in parental BW cells incubated with beta cells, and in NK-p46-CD3ζ transfected BW cells incubated with the HeLa cells (FIG. 2B), pancreatic exocrine tissue derived cells or peripheral blood lymphocytes.

Figures 3A, 3B:
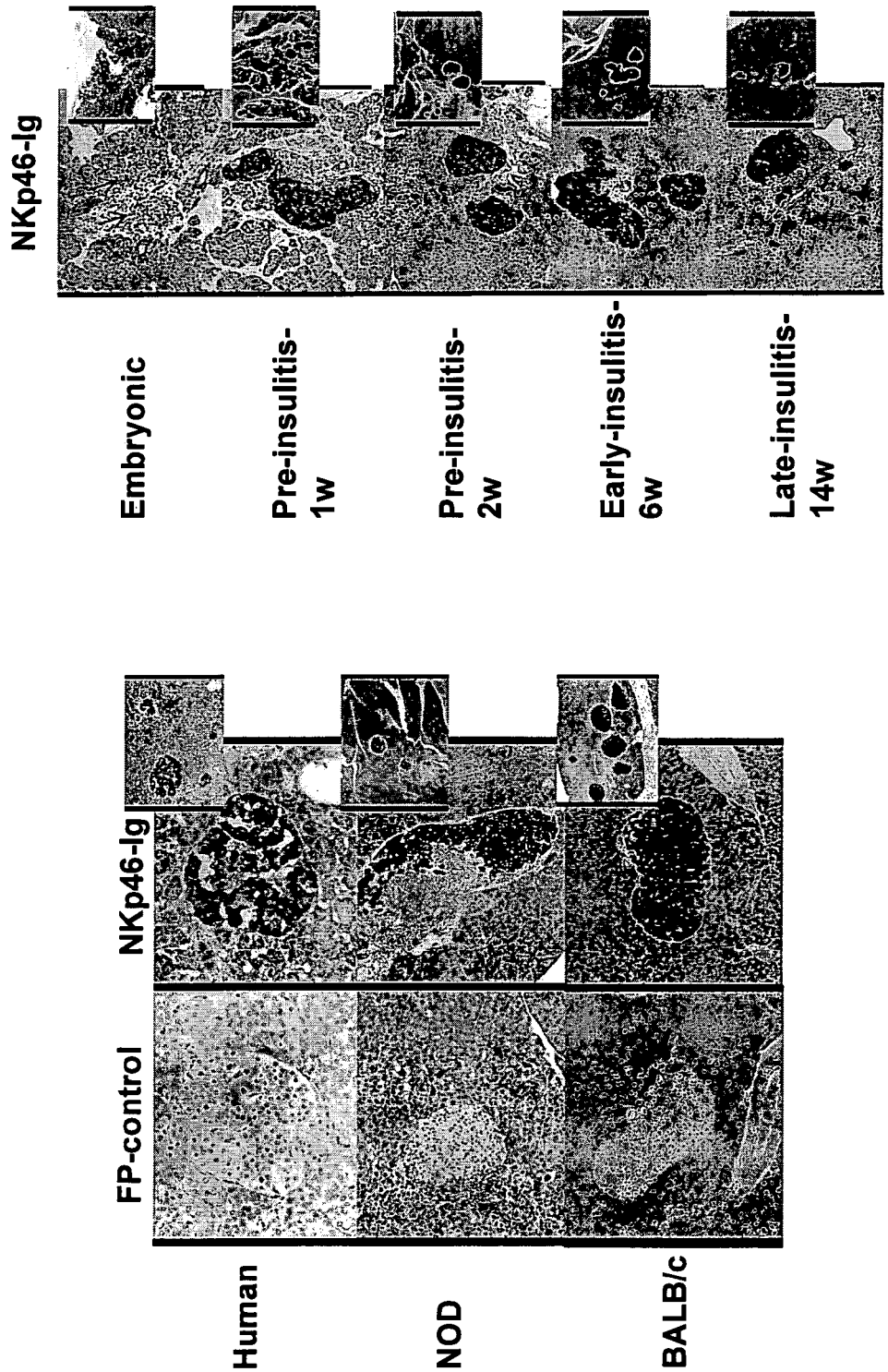
FIGS. 3A-3I show that NKp46-Ig recognizes mouse and human beta cells in situ.

To demonstrate that ligands for NKp46 also exist on human beta cells and that specific staining can be observed in the endocrine tissue of the whole pancreas, immunohistochemical staining was performed. Intense NKp46-Ig staining of beta cells was observed in islets of pancreatic tissues derived from human, female NOD mice, and BALB/c mice (FIG. 3A). In female NOD mice, the observed insulitis was manifested by mononuclear cell infiltration, and the residual pancreatic islets cells were stained by NKp46-Ig.

Figures 3C, 3D:
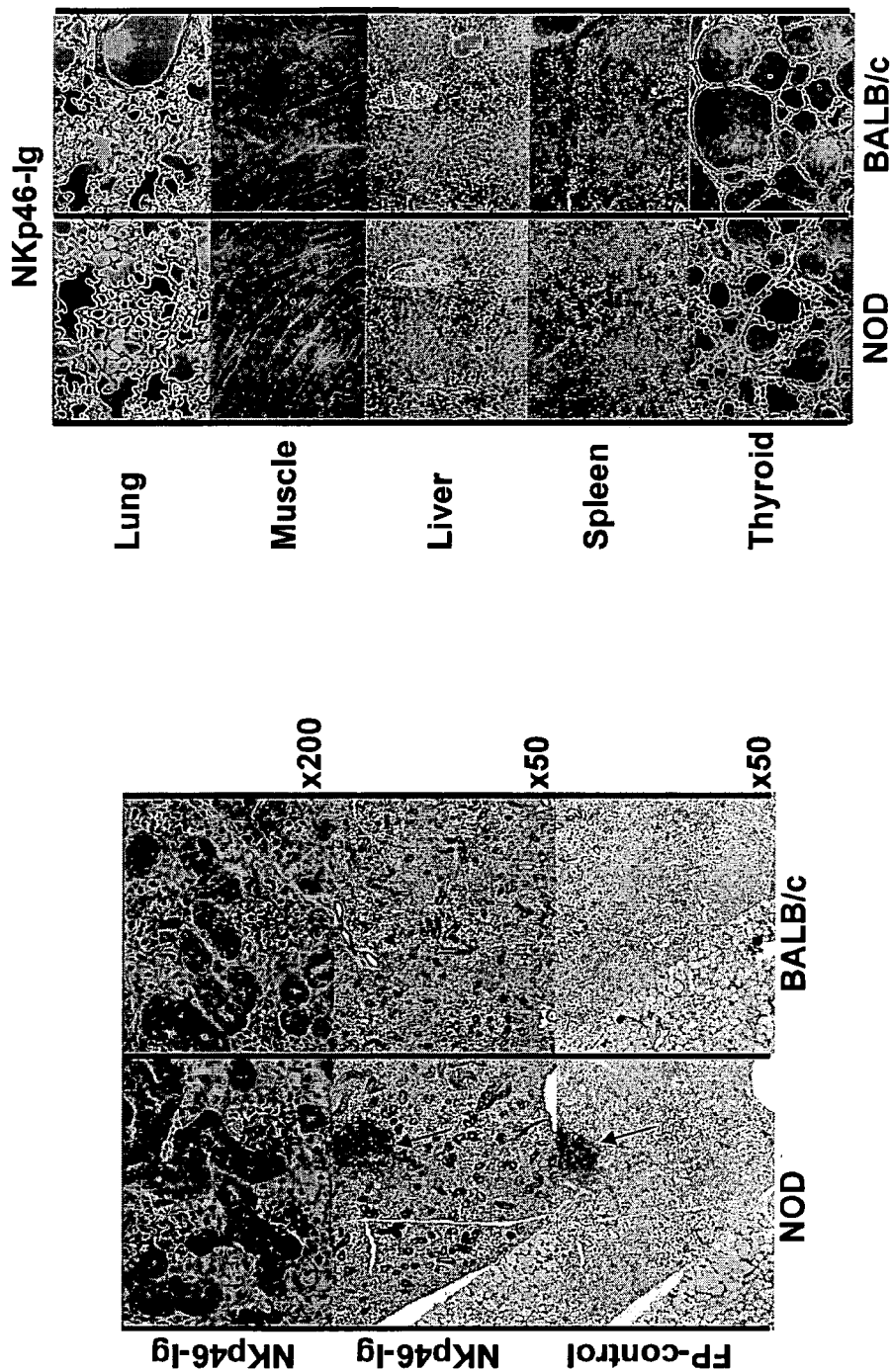

To investigate the importance of NKp46 ligand in pathogenesis of T1D, we performed immunohistochemical staining of NOD islets before and after development of insulitis, including the embryonic period. NKp46 ligands were not detected in the embryonic islets (E20, FIG. 3B). However, NKp46 ligands gradually appeared at the postnatal stage, and were present prior to insulitis development (week 2), and throughout the progression of insulitis (weeks 6 and 14; FIG. 3B). Insulitis in T1D of NOD mice is accompanied by autoimmune sialitis, and NKp46 ligands were expressed in salivary glands of female NOD and BALB/c mice (FIG. 3C). In the NOD mice, salivary gland mononuclear cell infiltration is seen (arrows, FIG. 3C). Other tissues examined in female NOD and BALB/c mice (lung, muscle, liver, spleen, thyroid) were not recognized by NKp46-Ig (FIG. 3D).

Figure 3E:
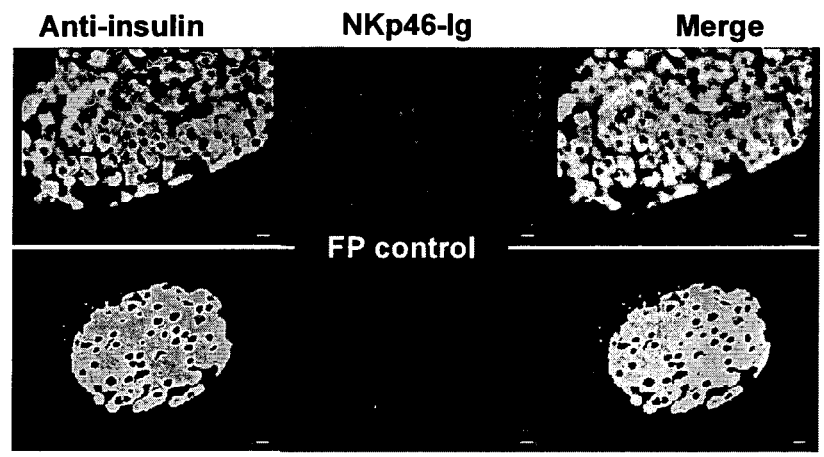
Figure 3F:
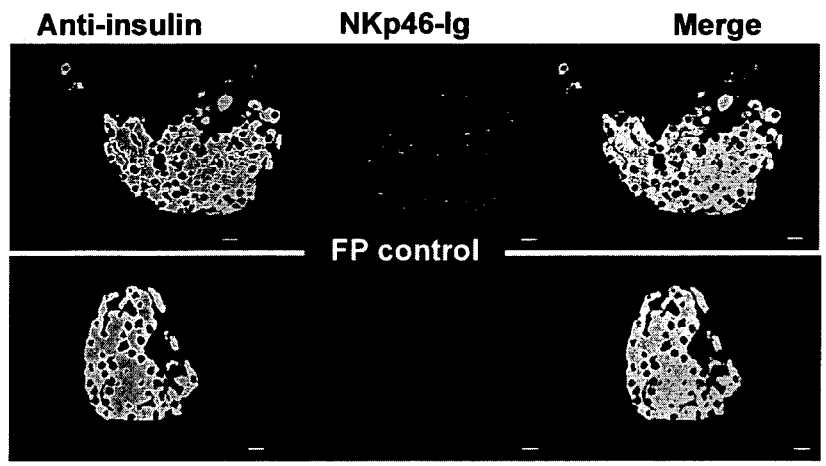
Figure 3G:
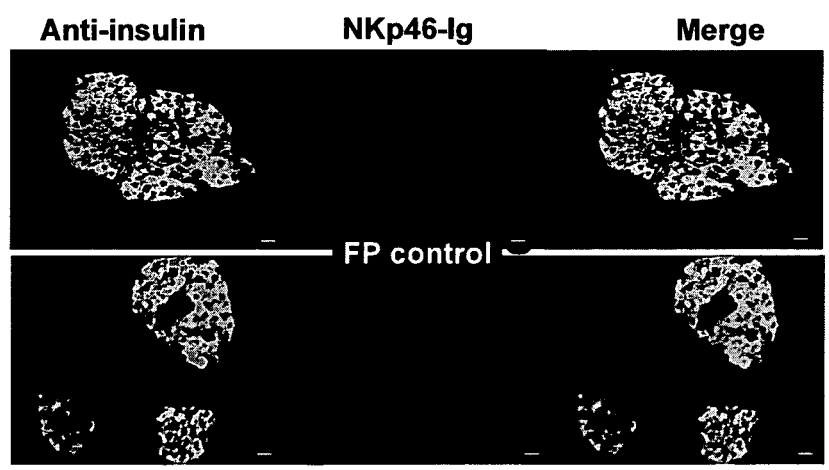
Figure 3H:
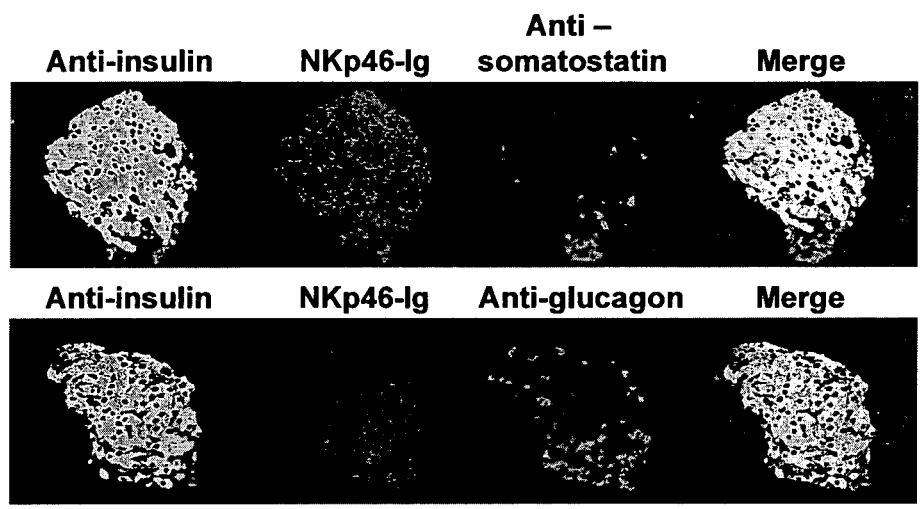
Figure 3I:
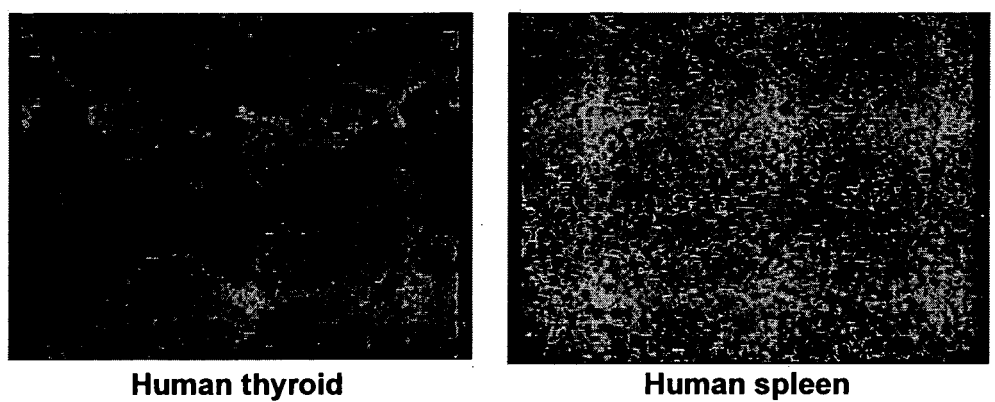

To support the observation that the ligand for NKp46 in pancreatic tissue is specifically expressed on insulin-producing beta cells and not on other islet cells (e.g. glucagon- or somatostatin-producing cells), we performed double and triple immunofluorescence staining of pancreatic tissue derived from BALB/c (FIG. 3E), NOD mice (FIG. 3F) and human (FIG. 3G). As shown in FIGS. 3E-G, there was substantial overlap of staining with NKp46-Ig and anti-insulin, indicating that NKp46 uniquely stains beta cells. The staining was specific, as no staining was observed with the control fusion protein NKp46D1-Ig (FIGS. 3E-G; FP control), or CEA-Ig, and there was no overlap for staining with anti-somatostatin or anti-glucagon and NKp46-Ig recognition (FIG. 3H). Other normal tissues examined, such as human thyroid and spleen were not recognized by NKp46-Ig (FIG. 3I). Taken together, the four different methods used indicate that a specific ligand for NKp46 is expressed on beta cells in human and mice.

Example 2

Beta Cells Induce Degranulation of NK Cells in an NKp46-Dependent Manner

The two main functions of NK cells are direct cytotoxicity and cytokine secretion, including interferon-γ (IFN-γ) and tumor necrosis factor (TNF). Our next aim was therefore to determine whether NKp46 could be activated by beta cells. To test the induction of cytokine secretion we used NK cells obtained from NCR-1$^{gfp/gfp}$ knockout mice and from heterozygous NCR-1$^{+/gfp}$ mice (23). In these knockout mice, a reporter gene encoding green fluorescent protein (GFP) is inserted into the NCR-1 locus and thus the NKp46 gene is knocked out, and all NK cells are labeled green. The heterozygous NCR-1$^{+/gfp}$ mice are normal and show function similar to that of wild type mice (23).

Figure 4A:
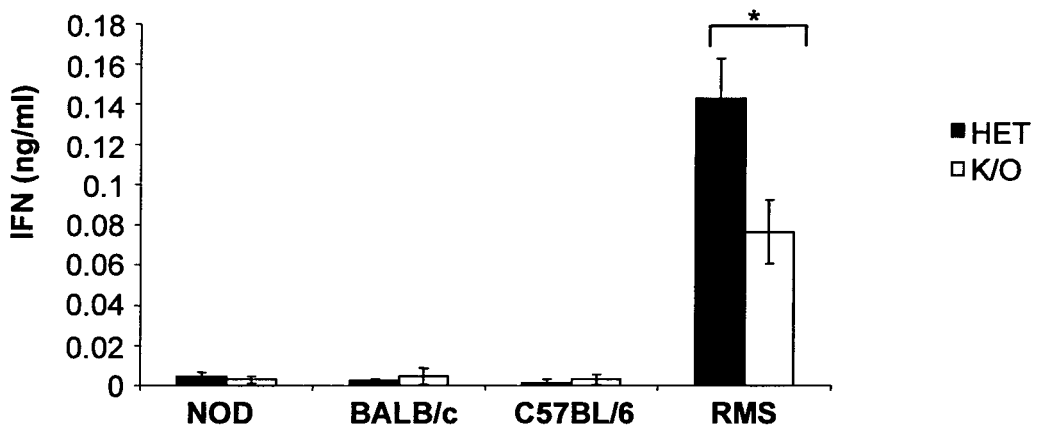
FIGS. 4A-4C show NKp46-mediated killing of beta cells.

To assay cytokine secretion from NK cells, we isolated GFP-expressing NK cells from the splenocytes of NCR-1$^{+/gfp}$ and NCR-1$^{gfp/gfp}$ mice and incubated them together with beta cells derived from NOD, BALB/c and C57BL/6 mice. Neither IFN-γ (FIG. 4A) nor TNF was secreted, irrespective of expression of NCR-1. However, NCR-1$^{gfp/gfp}$ NK cells secreted less IFN-γ than did NCR-1$^{+/gfp}$ NK cells when incubated together with a mouse rhabdomyosarcoma (RMS) cell line. Thus, it was concluded that the interaction of NKp46 with its ligand(s) on beta cells does not lead to cytokine secretion.

Figure 4B:
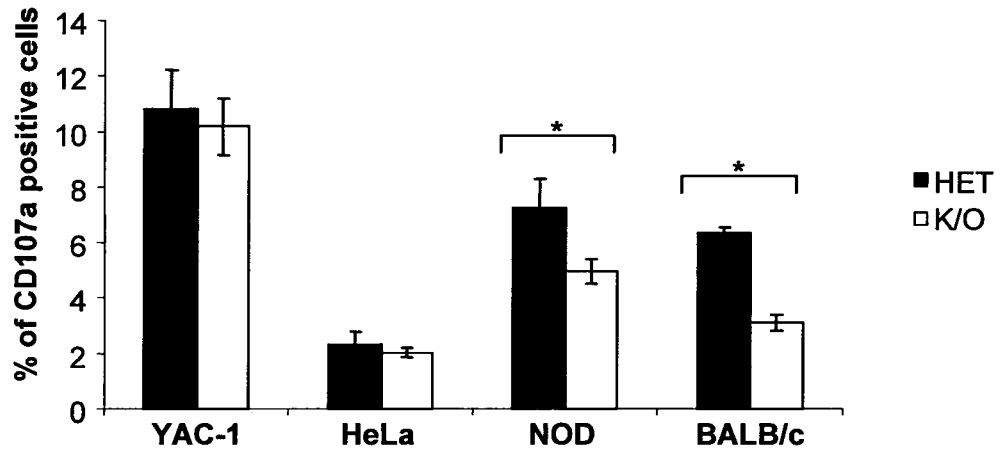

NK degranulation (indicating mobilization of CD107a to the cell surface; Refs. 30, 31) was then examined, rather than direct cytotoxicity, because mouse beta cells hardly proliferate and thus it is almost impossible to label them with radioactive isotopes. NK cells obtained from the spleens of NCR-1$^{+/gfp}$ and NCR-1$^{gfp/gfp}$ mice were incubated with beta cells derived from BALB/c and NOD mice. Significantly less degranulation was observed in the NCR-1$^{gfp/gfp}$ incubated with beta cells derived from each mouse strain (FIG. 4B). In contrast, NCR-1$^{+/gfp}$ and NCR-1$^{gfp/gfp}$ NK cells showed similar degranulation in response to YAC-1 cells, which are killed in an NCR1-independent manner (23), and minimal NK cell degranulation was observed with the negative control HeLa (FIG. 4B).

Figure 4C:
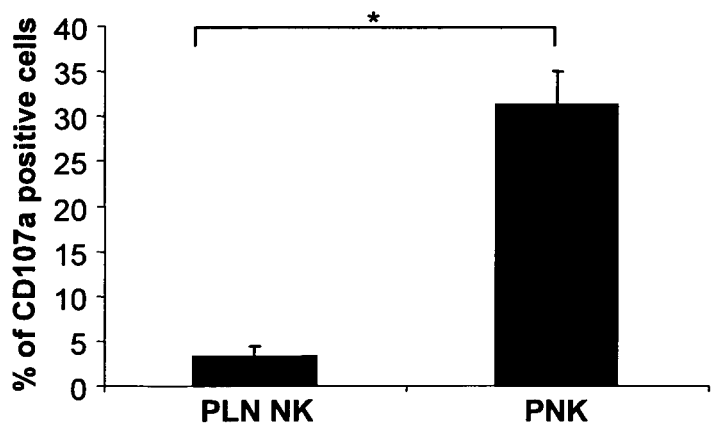

Finally, we examined the in vivo degranulation state of pathogenic pancreatic NK cells, which are present in the islets of NOD mice during diabetes development. We isolated NK cells from pancreatic lymph nodes and from beta cell islets of pre-diabetic female NOD mice (12 weeks old) and stained them for CD107a expression. Substantial degranulation of the pathogenic pancreatic islets NK cells was observed, while little or no degranulation was found in the pancreatic lymph node NK cells (FIG. 4C). In agreement with the above results, no IFN-γ secretion was observed from the pathogenic pancreatic NK cells. Thus, the pathogenic NK cells present in vivo in the pancreatic islets had degranulated.

Example 3

Impaired Diabetes Development in the Absence of NCR-1

Figure 5A:
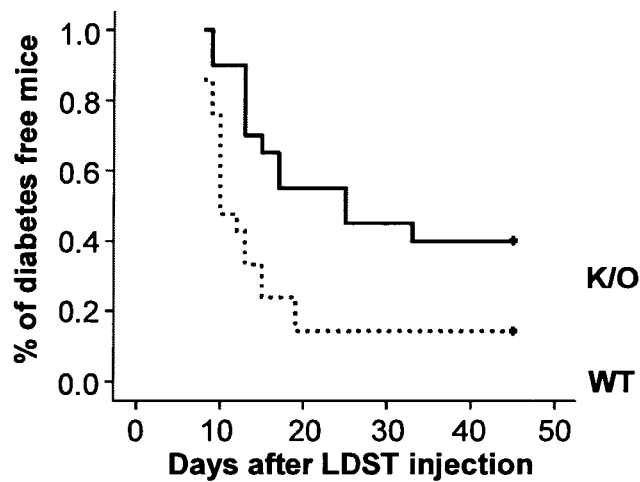
FIGS. 5A-5C show that diabetes development is impaired in the absence of NKp46.
Figure 5B:
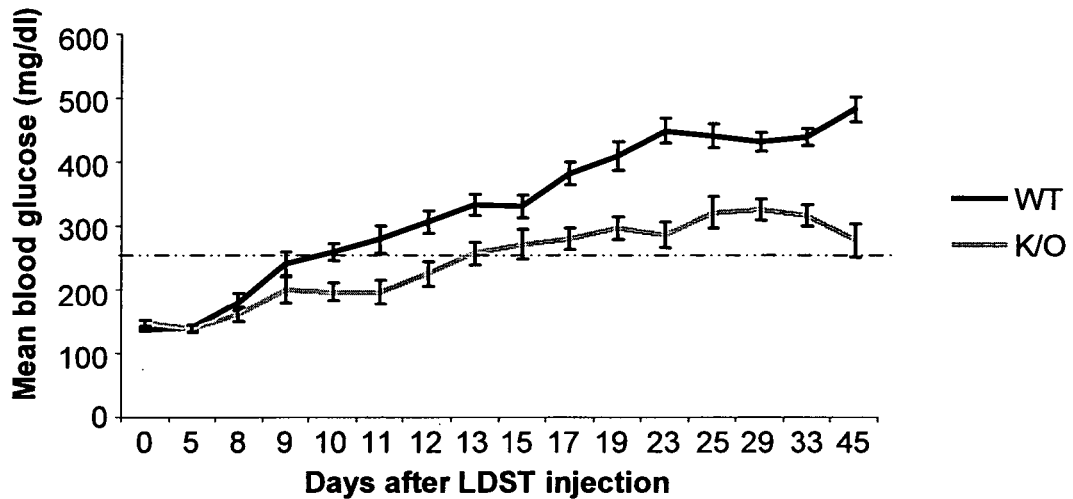

Our next goal was to test the function of NKp46 in diabetes development in vivo. Sex- and age-matched NCR-1$^{gfp/gfp}$ knockout mice and heterozygous NCR-1$^{+/gfp}$ mice were injected intraperitoneally for 5 consecutive days with streptozotocin, and blood glucose concentrations were measured from day 7 and up to 45 days post injection. In the absence of NCR-1, diabetes development was significantly impaired (p=0.008, Kaplan-Meier analysis with log-rank test; FIG. 5A). Furthermore, in order to assess the effect of the absence of NKp46 on the severity of diabetes, we examined the mean blood glucose levels in mice that had developed diabetes. Hyperglycemia, defined as a non-fasting blood glucose levels of ≥250 mg/dl in two sequential measurements, was less severe in NCR-1$^{gfp/gfp}$ diabetic mice (FIG. 5B; p<0.001, ANOVA model).

Figure 5C:
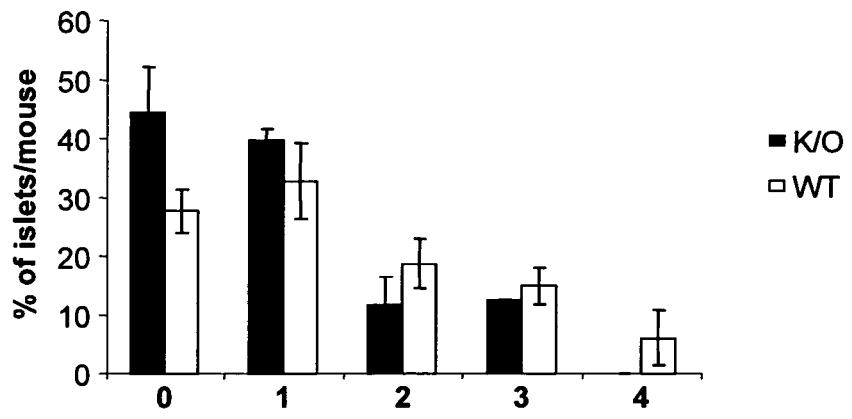

The 'protective' effect in the NCR-1 knockout mice was associated with decreased insulitis, as determined using a published pathological insulitis scale (32). According to this scale, insulitis is calculated as the percent of islets per mouse in each stage of insulitis (0-no infiltration; 1-minor infiltration; 2-minor peri-insulitis; 3-clear peri-insulitis; 4-insulitis with intra-islet invasion by mononuclear cells). In the wild type mice, all 4 stages were observed and around 6% of the islets demonstrated stage 4 insulitis, whereas in the knockout mice around 45% of the islets had no infiltration (compared to less than 30% in the wild type mice) and stage 4 insulitis was not observed (FIG. 5C). These results indicate that NKp46 is important for diabetes development and islet destruction in the LDST model.

Example 4

Appearance of NK Cells in the Pancreas During Diabetes Development

While NKp46 is expressed on normal beta cells, diabetes does not develop in every individual. One hypothesis to explain this fact is that NK and T cells that are normally not found in the pancreas appear in this organ upon diabetes development. To test this hypothesis the appearance of NK cells in the pancreatic tissues was monitored in two murine models of T1D.

Figure 6A:
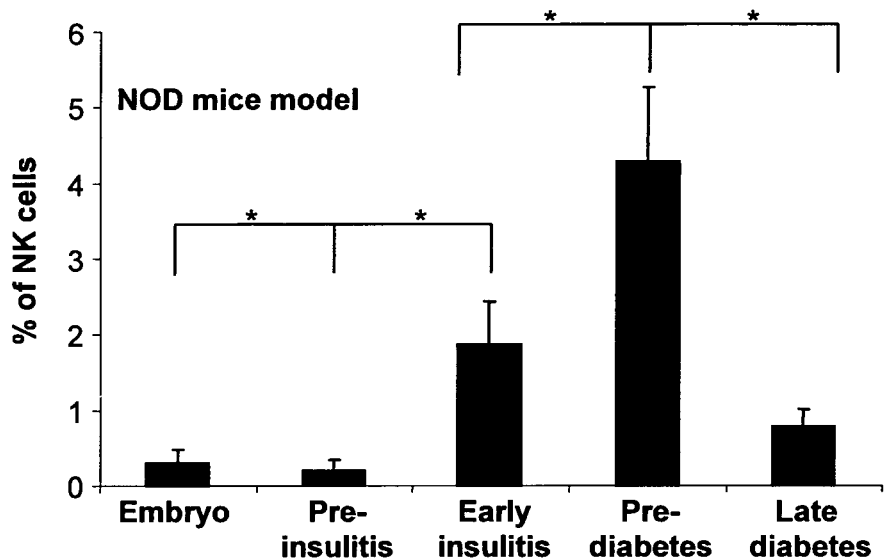
FIGS. 6A-6B show that NK cells accumulate in the pancreas during diabetes development.
Figure 6B:
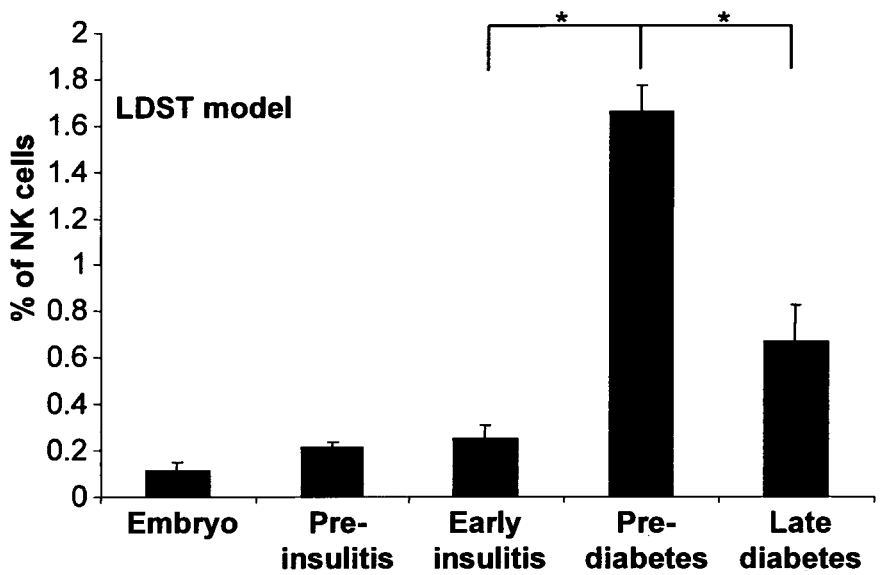

We followed NK cells during the embryonic period (E20), pre-insulitis (3-4 weeks), early insulitis (6-8 weeks), pre-diabetes (12-14 weeks, mice with normal fasting glucose level but pathological intraperitoneal glucose tolerance test), and late overt diabetes stage (2-3 weeks after diabetes diagnosis). The highest percentage (around 4%) of NK cells expressing NCR-1 in the pancreas was in the pre-diabetic stage (FIGS. 6A and 6B). In the late phase of diabetes development, the percentage of NK cells was significantly reduced (around 0.7%). We also monitored NK cell appearance (by GFP expression) in the pancreatic tissues of LDST-injected NCR-1$^{gfp/gfp}$ knockout mice, during the embryonic period (E20), pre-insulitis (day 0; day of LDST injection), early insulitis (day 7 after LDST injection), pre-diabetes (day 9 after LDST injection), and late overt diabetes (day 45 after LDST injection). The most NK cells were observed in the pancreas in the pre-diabetic stage, on day 9 after the injection, the same day at which the transition from insulitis to diabetes usually starts in this model (FIGS. 5B and 6A-B). The few NK cells observed in the embryonic period and in the pre-insulitis stage in both models were probably contaminating lymphocytes.

By monitoring cells positive for CD3 we could also follow the T cell appearance in the pancreas and found that similarly to NK cells, T cells are normally not found in the pancreas and that they appear in the pancreas concomitantly with the NK cells. Thus, under normal conditions, despite the fact that pancreatic beta cells of both human and mice express ligands for NKp46, diabetes does not develop probably because NK cells and T cells are absent from the pancreas.

Example 5

NKp46 Proteins Prevent Diabetes Development when Injected Early

Our next aim was to demonstrate that NKp46 is indeed involved in diabetes development in the NOD mouse model and in parallel, to develop a new therapeutic tool for the treatment of T1D. It was demonstrated that treatment of NOD mice with non-depleting anti-NKG2D monoclonal antibodies attenuated diabetes development by impairing the function of autoreactive CD8+ T cells (25). However, no blocking, non-depleting antibody directed against the murine NKp46 receptor is available. However, we succeeded in inducing specific anti-NKp46 antibodies in NOD mice by repeated injections of the NKp46-Ig fusion protein. We used NKp46-Ig and NCR1-Ig, and, to prevent non-specific binding we also used an additional version of the murine NCR-1 receptor that lacks the complement- and Fc-binding sites (NCR1-t).

Figure 7:
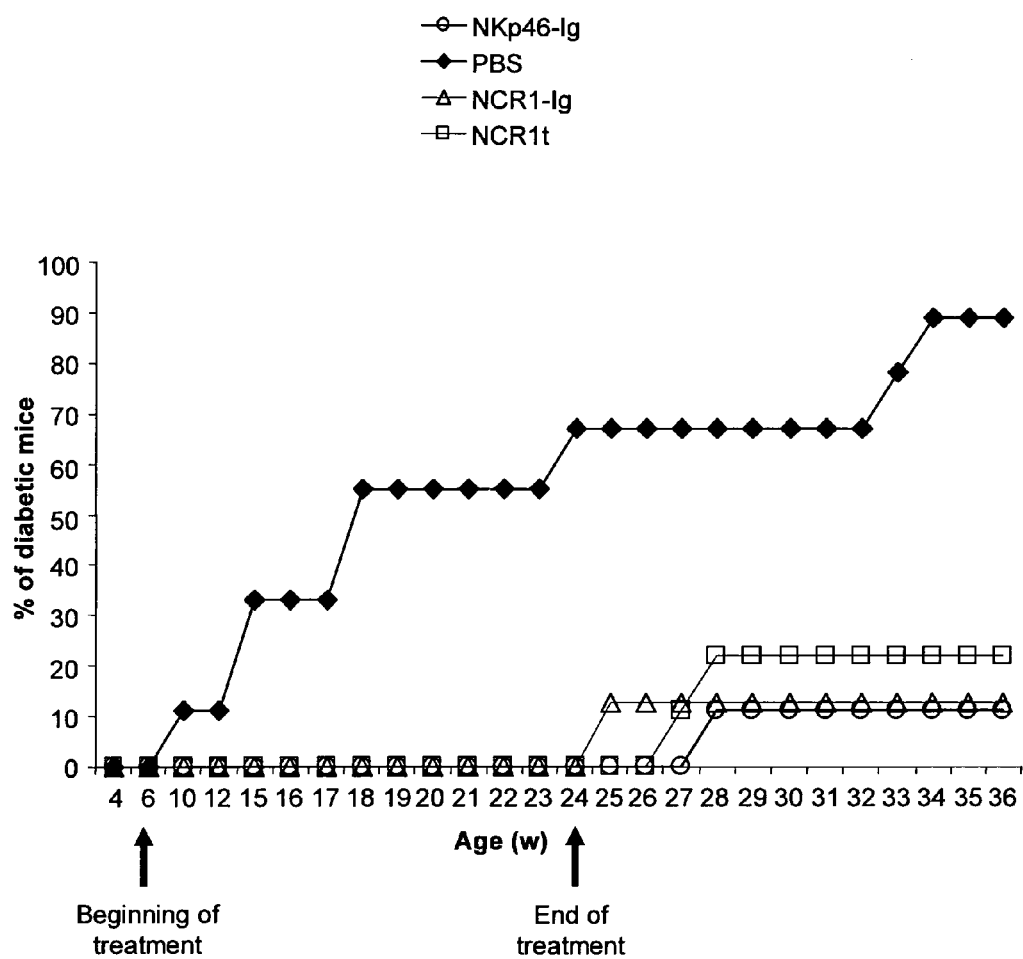
FIG. 7 shows that treatment with NKp46 fusion proteins prevents diabetes development in NOD mice. Development of diabetes (blood glucose level above 250 mg/dl in two consecutive measurements) in female NOD mice treated with NKp46-Ig (open circles), NCR1-Ig (open triangles) or NCR1-t (open squares), each injected at 0.005 g/kg body weight injected intraperitoneally twice weekly, or PBS (black filled diamonds) starting from 6 and up to 24 weeks (w) of age (treatment (Tx) upward arrows). $P<0.0002$, fusion protein versus PBS (Kaplan-Meyer analysis, log-rank test). Data are representative of two independent experiments with eight to nine mice per group.

Female NOD mice (n=8-9) were injected intraperitoneally with the various fusion proteins at a dose of 0.005 g per kg body weight, or PBS twice a week, starting from 6 weeks of age. Mice treated with PBS alone started developing diabetes at 10 weeks of age and 67% were diabetic by 24 weeks, at which point, treatment was stopped (FIG. 7). Remarkably, diabetes was not observed in any of the NKp46-treated NOD mice during the first 19 weeks of treatment. Moreover, most of the fusion protein treated NOD mice remained vital and disease-free up to 36 weeks of age. In contrast, 89% of the PBS-treated mice became diabetic and most of them died before 33 weeks of age (FIG. 7). This difference between the groups was statistically significant (p=0.000015, Kaplan-Meier analysis with the log-rank test).

Hematoxylin and eosin staining of pancreatic tissue derived from all fusion protein-treated mice showed many residual islets with usually only mild insulitis, a situation similar to that of pancreatic tissue derived from healthy 30 week old, untreated non-diabetic female NOD mice. In contrast, no pancreatic islets were detected in mice injected with PBS. No side effects were noted in the treated mice, either by gross examination or histological analysis.

To investigate the mechanism responsible for the protective effect mediated by the NKp46 fusion proteins, sera were collected from the various mouse groups during the course of the experiment. Injection of the various NKp46-Ig variants resulted in the generation of specific antibodies directed against NKp46 and NCR-1, but injection of PBS did not. The anti-NKp46 and anti NCR-1 antibodies were mostly of the IgM isotype, and were present in the serum starting at 2 and 4 weeks respectively following fusion protein injection, and remained in the serum for up to 36 weeks of age (the end of the experiment).

To gain insight into the mechanism by which the soluble NKp46 fusion proteins inhibited diabetes development, we first excluded the possibility that these fusion proteins acted by depleting NK cells or by suppressing appearance of NK cells in the pancreas, by noting that similar percentages of NK cells were found in the peripheral blood and in the pancreatic tissues of the PBS treated and the fusion protein treated mouse groups. The observation that the NK cell percentages in the pancreatic tissues of the healthy NKp46-Ig treated mice were not altered following the various treatments is in contrast to the reduction of CD8+ T cells percentage in the healthy pancreas of the mice treated with an anti-NKG2D antibody (25). Furthermore, the unknown NKp46 ligand was expressed at similar levels on beta cells derived from the fusion protein treated mice and the PBS group. Potential involvement of the Fc portion was also ruled out because the truncated version of the fusion protein, which lacks the complement- and Fc-binding domain, was almost as effective as the other fusion proteins in suppressing diabetes (FIG. 7).

Figure 8A:
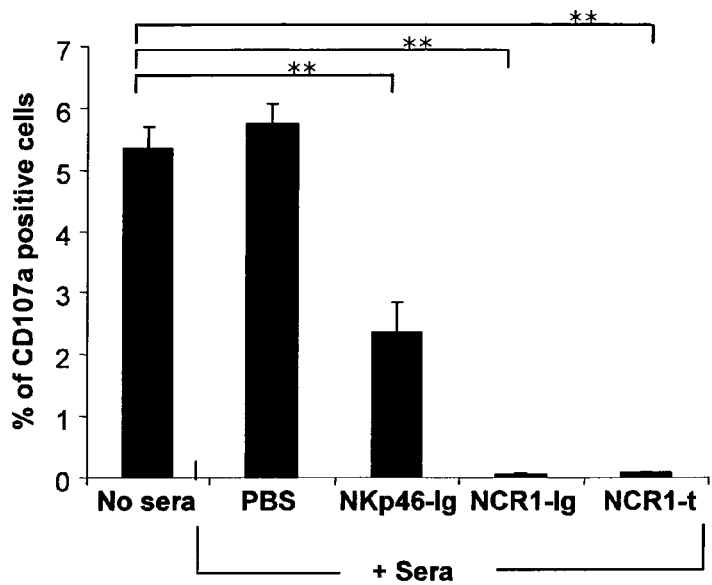
FIGS. 8A-8D show impaired NKp46 function.

To test whether the anti NKp46/NCR-1 antibodies generated during fusion protein injection could block the degranulation of NK cells, we cultured NK cells derived from the spleens of 8 week old non-diabetic female NOD mice with beta cells obtained from pre-diabetic female NOD mice and performed the CD107a mobilization assay. FIG. 8A shows that the degranulation of NK cells was significantly reduced (p<0.05) after pre-incubation with serum derived from mice treated with the NKp46 fusion proteins, while normal sera or serum derived from the PBS-treated mice did not alter the NK degranulation (p=0.3, FIG. 8A).

Figure 8B:
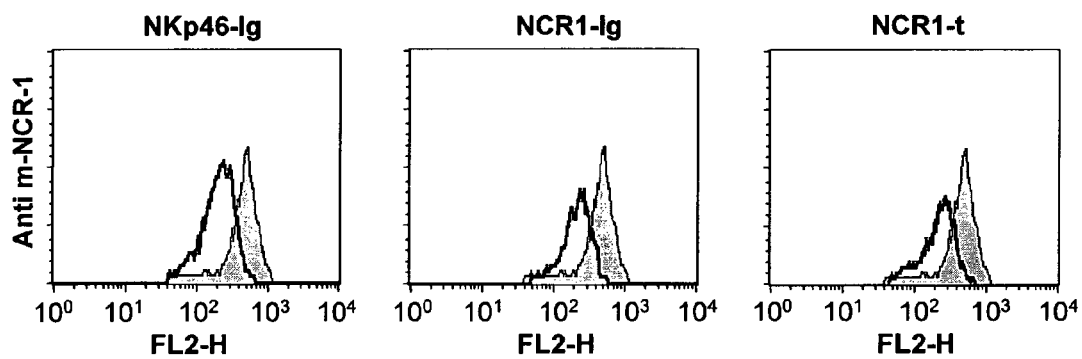

As injection of anti-NKG2D, or a soluble NKG2D ligand, induces internalization of the NKG2D receptor (22, 34), we determined whether the NCR-1 receptor was also down regulated due to the generation of NKp46 specific antibodies in the fusion protein treated mice. We observed significant reduction in the expression of the NCR-1 receptor on NK cells derived from mice treated with the fusion proteins compared to the PBS-treated mice (FIG. 8B). The NCR-1 reduction was systemic, as a similar reduction was observed in NK cells derived from blood or pancreas. Staining with anti-mouse IgG was similar on NK cells from PBS- and the fusion protein-treated groups, indicating that the NK cells were not simply coated with the mouse anti-NKp46 antibodies.

Figure 8C:
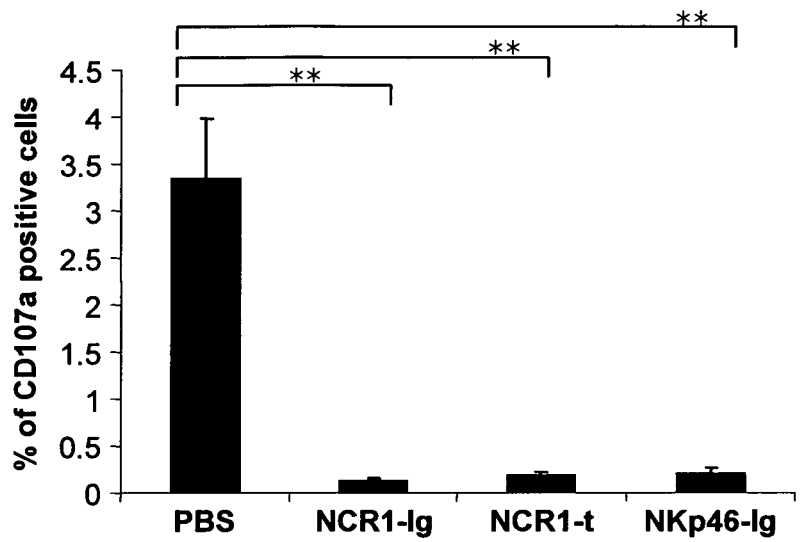

Our next aim was to determine whether the NKp46 down regulation would affect the degranulation of NK cells obtained from the treated mouse groups. For this purpose, we isolated NK cells from splenocytes of 36 week old mice and at this point, 12 weeks after the end of the therapy, the PBS treated mice were already diabetic. In the diabetic, PBS treated mice, a low but still significant degranulation of NK cells was observed, while NK cells derived from the various healthy NKp46 treated groups failed to degranulate upon interaction with beta cells (p<0.001, FIG. 8C). The relatively low function of NK cells derived from the PBS treated group compared to the healthy control 8 weeks old mice (FIG. 8A), could be due to the effect of hyperglycemia.

Figure 8D:
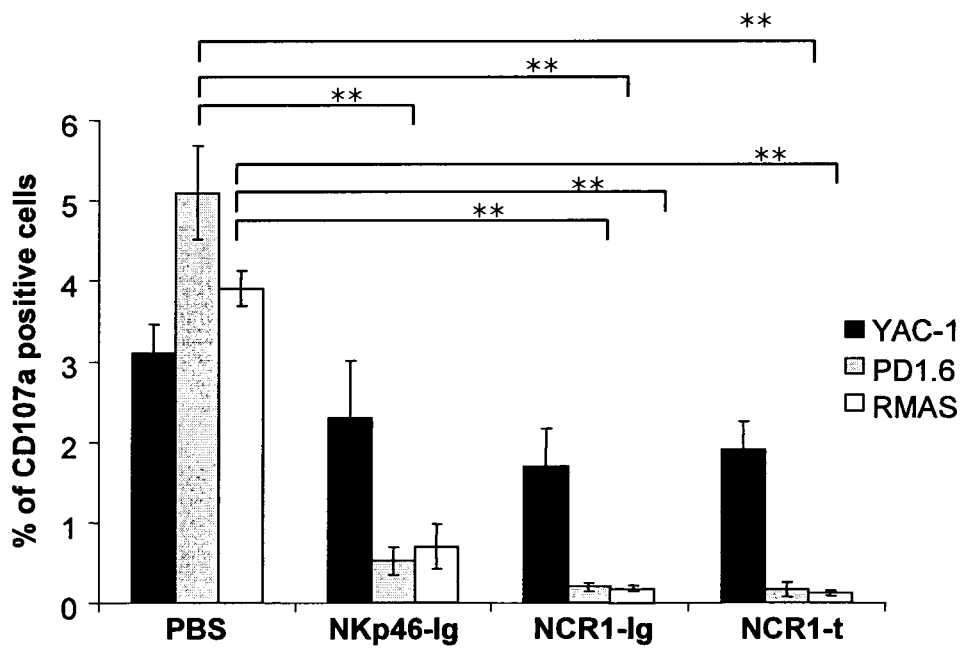

Finally, to demonstrate that the impairment in NK cell activity is specific to the NKp46 receptor, we investigated the degranulation capability of NK cells derived from PBS- or fusion protein-treated mice after incubation them with NKp46-dependent target cells (such as PD1.6 and RMAS; Refs. 23, 35), or NKp46-independent, NKG2D-dependent, target cells (such as YAC-1; Ref 23). All target cells whose killing is NKp46-dependent induced minimal CD107a expression on NK cells derived from the various NKp46 fusion proteins, while substantial CD107a expression was observed with NK cells derived from the PBS-treated mice. In contrast, NK cells derived from all groups expressed CD107a after incubation with YAC-1 cells (p=0.38, FIG. 8D). These results indicate that the lack of NK cell cytotoxicity is restricted mainly to the NKp46 receptor and that the major mechanism of NKp46 dysfunction is the down-regulation of the receptor. Thus, NKp46 is crucial for diabetes development and in the absence of NKp46 or when the function of NKp46 is impaired, diabetes, in most cases, is prevented.

Example 6

In Vivo Administration of NKp46 Fusion Proteins to Female NOD Mice in the Pre-Diabetic Stage Prevents Type 1 Diabetes Development To investigate whether our treatment modality can prevent or delay the onset of diabetes in the late pre-diabetic stage and to demonstrate that the injection of the Ig fusion protein did not result in a non-specific effect, we injected 11-12 week old non-diabetic female NOD mice with PBS, NKp46-Ig, NCR-1-Ig or the irrelevant fusion protein CEA-Ig. As expected, all mice developed specific antibodies directed against the injected fusion protein, including the control CEA-Ig. The anti-NCR-1 antibodies were detected in the serum around 4 weeks after the first injection (probably because tolerance had to be broken) and in the other groups fusion protein specific antibodies they were detected as early as 2 weeks following injection. Most of the antibodies generated in all of the injected mouse groups were of the IgM isotype.

Figure 9A:
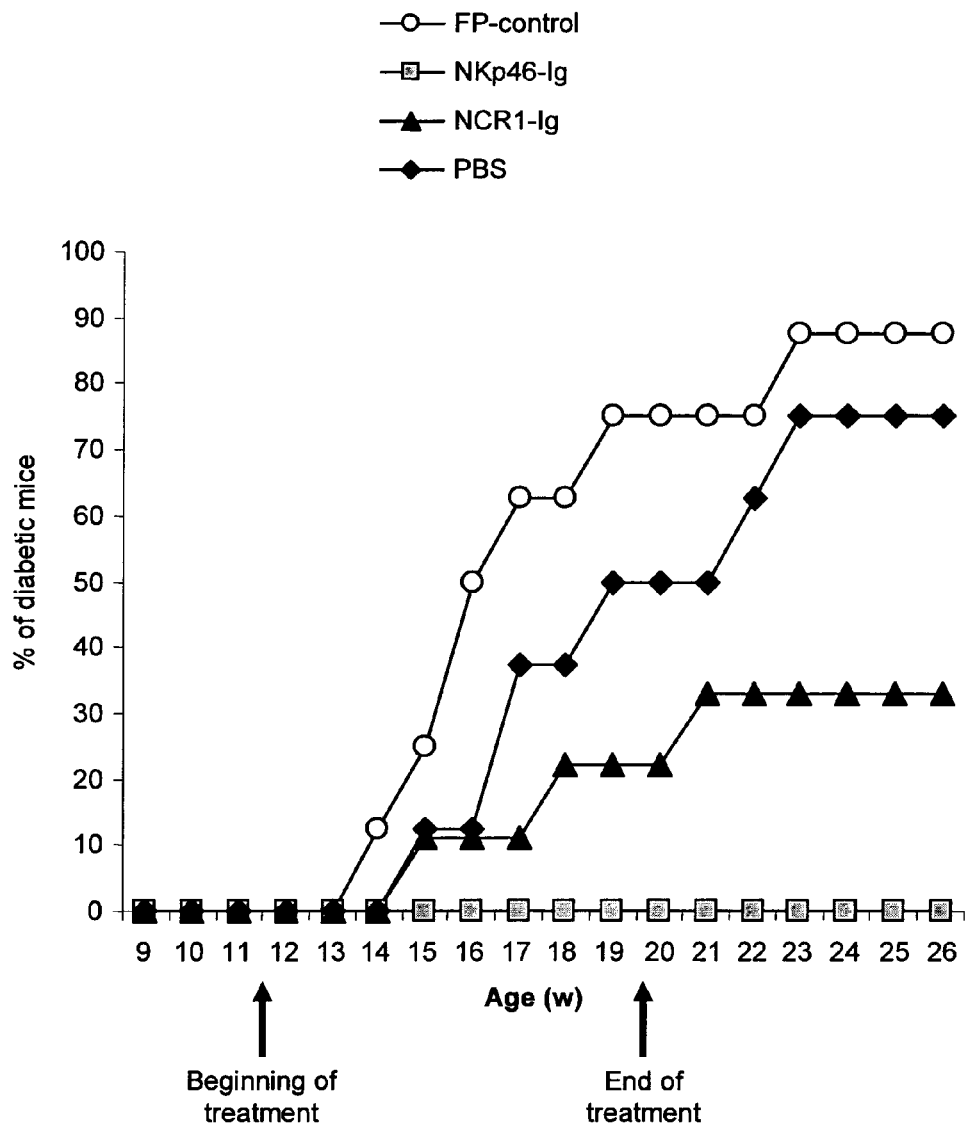
FIGS. 9A-9C show that NKp46 treatment at a late pre-diabetic stage prevents diabetes development.
Figure 9B:
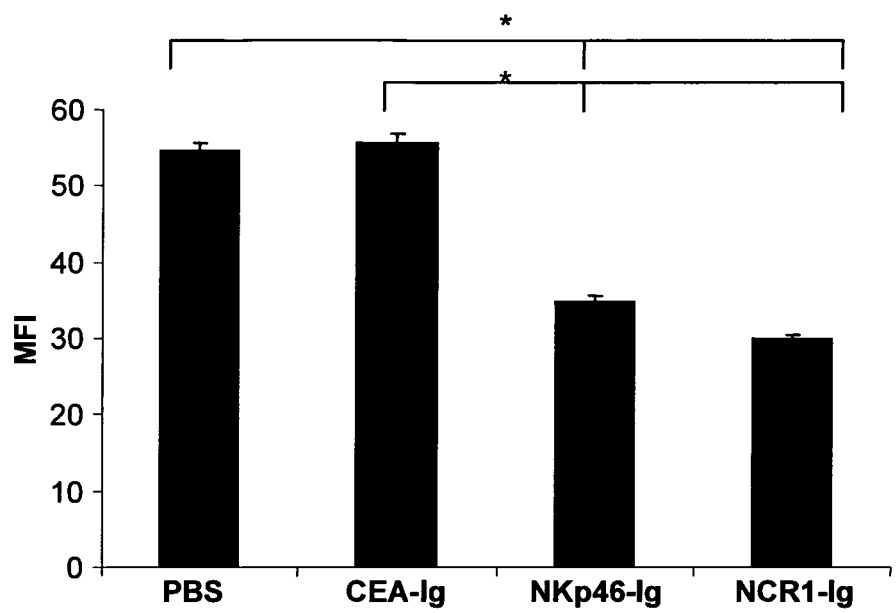
Figure 9C:
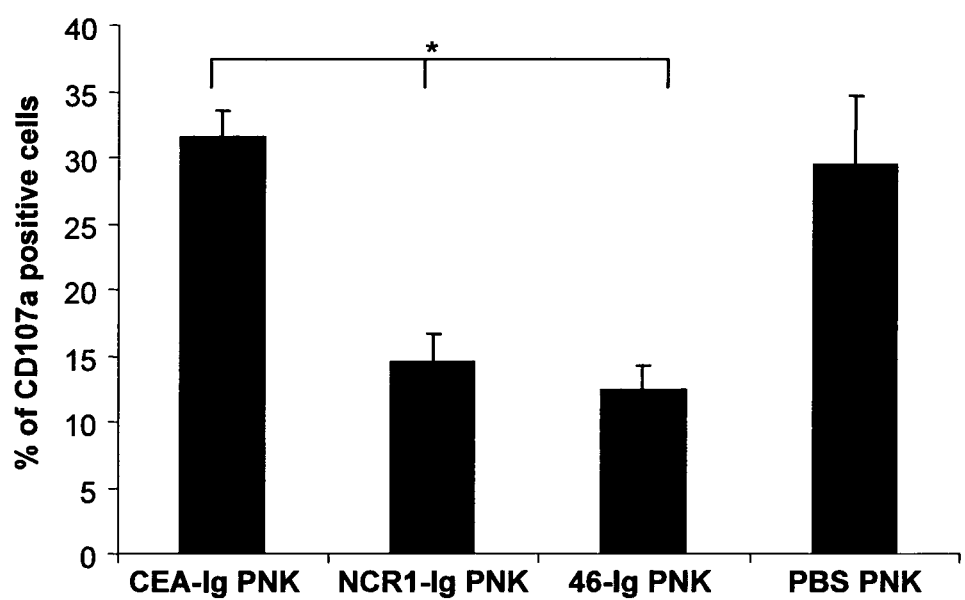

NOD mice were injected with the various fusion proteins or PBS, starting from 11-12 weeks of age until 20 weeks of age. Diabetes diagnosis, schedule and dose of fusion protein injection were the same as in the early injection experiment (FIG. 7). CEA-Ig did not prevent diabetes development and even caused a slight acceleration in the disease compared to the PBS treated group (FIG. 9A). However, 67% of the NCR-1-Ig treated mice, and all of the NKp46-Ig treated mice remained diabetes-free until 20 weeks of age and during the first 6 weeks after halting therapy (FIG. 9A). The difference between the groups was statistically significant (p=0.001, Kaplan-Meier analysis with the log-rank test). Antibody generation resulted in a specific down-regulation of NCR-1 (FIG. 9B) which was observed 2 and 4 weeks after NKp46-Ig and NCR-1-Ig injections, respectively. The NCR-1-Ig treatment was less efficient compared to the NKp46-Ig treatment probably because the anti-NCR-1 antibodies were observed only about 4 weeks after the initial injection. Finally, to test if the down-regulation of NCR-1 would translate into reduced NK cell degranulation in vivo, we obtained the pathogenic pancreatic NK cells derived from the islets of each of the treated mice groups and stained them for CD107a expression. As can be seen in FIG. 9C, while around 30% of the pathogenic pancreatic NK cells derived from the beta cells of the CEA-Ig, or PBS treated groups expressed CD107a, in the NKp46- and NCR-1 treated groups, less than 15% of the NK cells had substantial expression of CD107a.

Taken together, these findings indicate that NKp46 is critical for development of diabetes and that NKp46 therapy might be used to prevent diabetes development at the late pre-diabetic stage, when beta cells face immediate destruction by NK cells.

REFERENCES

1. Delovitch, T. L. & Singh, B. The nonobese diabetic mouse as a model of autoimmune diabetes: immune dysregulation gets the NOD. *Immunity* 7, 727-738 (1997).

2. Kikutani, H. & Makino, S. The murine autoimmune diabetes model: NOD and related strains. *Adv Immunol* 51, 285-322 (1992).
3. Like, A. A. & Rossini, A. A. Streptozotocin-induced pancreatic insulitis: new model of diabetes mellitus. *Science* 193, 415-417 (1976).
4. O'Brien, B. A., Harmon, B. V., Cameron, D. P. & Allan, D. J. Beta-cell apoptosis is responsible for the development of IDDM in the multiple low-dose streptozotocin model. *J Pathol* 178, 176-181 (1996).
5. Paik, S. G., Fleischer, N. & Shin, S. I. Insulin-dependent diabetes mellitus induced by subdiabetogenic doses of streptozotocin: obligatory role of cell-mediated autoimmune processes. *Proc Natl Acad Sci USA* 77, 6129-6133 (1980).
6. Hutchings, P. et al. Transfer of diabetes in mice prevented by blockade of adhesion-promoting receptor on macrophages. *Nature* 348, 639-642 (1990).
7. Miyazaki, A. et al. Predominance of T lymphocytes in pancreatic islets and spleen of pre-diabetic non-obese diabetic (NOD) mice: a longitudinal study. *Clin Exp Immunol* 60, 622-630 (1985).
8. Dotta, F. et al. Coxsackie B4 virus infection of beta cells and natural killer cell insulitis in recent-onset type 1 diabetic patients. *Proc Natl Acad Sci USA* 104, 5115-5120 (2007).
9. Rodacki, M. et al. Altered natural killer cells in type 1 diabetic patients. *Diabetes* 56, 177-185 (2007).
10. Poirot, L., Benoist, C. & Mathis, D. Natural killer cells distinguish innocuous and destructive forms of pancreatic islet autoimmunity. *Proc Natl Acad Sci USA* 101, 8102-8107 (2004).
11. Alba, A. et al. Natural killer cells are required for accelerated type 1 diabetes driven by interferon-beta. *Clin Exp Immunol* 151, 467-475 (2008).
12. Moretta, A., Bottino, C., Mingari, M. C., Biassoni, R. & Moretta, L. What is a natural killer cell? *Nat Immunol* 3, 6-8 (2002).
13. Hanna, J. et al. Novel APC-like properties of human NK cells directly regulate T cell activation. *J Clin Invest* 114, 1612-1623 (2004).
14. Long, E. O. Tumor cell recognition by natural killer cells. *Semin Cancer Biol* 12, 57-61 (2002).
15. Kane, K. NK cells, MHC class I molecules and the missing self. *Scand J Immunol* 55, 221-228 (2002).
16. Lanier, L. L. NK cell recognition. *Annu Rev Immunol* 23, 225-274 (2005).
17. Raulet, D. H. Roles of the NKG2D immunoreceptor and its ligands. *Nat Rev Immunol* 3, 781-790 (2003).
18. Flodstrom, M., Shi, F. D., Sarvetnick, N. & Ljunggren, H. G. The natural killer cell—friend or foe in autoimmune disease? *Scand J Immunol* 55, 432-441 (2002).
19. Hansson, M., Kiessling, R. & Andersson, B. Human fetal thymus and bone marrow contain target cells for natural killer cells. *Eur J Immunol* 11, 8-12 (1981).
20. Nakamura, N. et al. Intrinsic cytotoxicity of natural killer cells to pancreatic islets in vitro. *Diabetes* 39, 836-843 (1990).
21. Morse, R. H., Seguin, R., McCrea, E. L. & Antel, J. P. NK cell-mediated lysis of autologous human oligodendrocytes. *J Neuroimmunol* 116, 107-115 (2001).
22. Ogasawara, K. et al. Impairment of NK cell function by NKG2D modulation in NOD mice. *Immunity* 18, 41-51 (2003).
23. Gazit, R. et al. Lethal influenza infection in the absence of the natural killer cell receptor gene Ncr1. *Nat Immunol* 7, 517-523 (2006).
24. Moretta, L. Lymphocyte effector mechanisms in innate and adaptive immunity. *Curr Opin Immunol* 17, 303-305 (2005).
25. Ogasawara, K. et al. NKG2D blockade prevents autoimmune diabetes in NOD mice. *Immunity* 20, 757-767 (2004).
26. Maier, L. M. et al. NKG2D-RAE-1 receptor-ligand variation does not account for the NK cell defect in nonobese diabetic mice. *J Immunol* 181, 7073-7080 (2008).
27. Arnon, T. I. et al. Recognition of viral hemagglutinins by NKp44 but not by NKp30. *Eur J Immunol* 31, 2680-2689 (2001).
28. Arnon, T. I. et al. The mechanisms controlling the recognition of tumor- and virus-infected cells by NKp46. *Blood* 103, 664-672 (2004).
29. Mandelboim, O. et al. Recognition of haemagglutinins on virus-infected cells by NKp46 activates lysis by human NK cells. *Nature* 409, 1055-1060 (2001).
30. Aktas, E., Kucuksezer, U. C., Bilgic, S., Erten, G. & Deniz, G. Relationship between CD107a expression and cytotoxic activity. *Cell Immunol* 254, 149-154 (2009).
31. Alter, G., Malenfant, J. M. & Altfeld, M. CD107a as a functional marker for the identification of natural killer cell activity. *J Immunol Methods* 294, 15-22 (2004).
32. Flodstrom, M., Tyrberg, B., Eizirik, D. L. & Sandler, S. Reduced sensitivity of inducible nitric oxide synthase-deficient mice to multiple low-dose streptozotocin-induced diabetes. *Diabetes* 48, 706-713 (1999).
33. Biassoni, R. et al. The murine homologue of the human NKp46, a triggering receptor involved in the induction of natural cytotoxicity. *Eur J Immunol* 29, 1014-1020 (1999).
34. Lodoen, M. et al. NKG2D-mediated natural killer cell protection against cytomegalovirus is impaired by viral gp40 modulation of retinoic acid early inducible 1 gene molecules. *J Exp Med* 197, 1245-1253 (2003).
35. Halfteck, G. G. et al. Enhanced in vivo growth of lymphoma tumors in the absence of the NK-activating receptor NKp46/NCR1. *J Immunol* 182, 2221-2230 (2009).
36. Alba, A. et al. IFN beta accelerates autoimmune type 1 diabetes in nonobese diabetic mice and breaks the tolerance to beta cells in nondiabetes-prone mice. *J Immunol* 173, 6667-6675 (2004).
37. Kitagawa, Y. et al. Islet cells but not thyrocytes are susceptible to lysis by NK cells. *J Autoimmun* 4, 703-716 (1991).
38. MacKay, P., Jacobson, J. & Rabinovitch, A. Spontaneous diabetes mellitus in the Bio-Breeding/Worcester rat. Evidence in vitro for natural killer cell lysis of islet cells. *J Clin Invest* 77, 916-924 (1986).
39. Foulis, A. K., McGill, M., Farquharson, M. A. & Hilton, D. A. A search for evidence of viral infection in pancreases of newly diagnosed patients with IDDM. *Diabetologia* 40, 53-61 (1997).
40. Horwitz, M. S. et al. Diabetes induced by Coxsackie virus: initiation by bystander damage and not molecular mimicry. *Nat Med* 4, 781-785 (1998).
41. Lodde, B. M. et al. NOD mouse model for Sjogren's syndrome: lack of longitudinal stability. *Oral Dis* 12, 566-572 (2006).
42. Gurr, W., Shaw, M., Li, Y. & Sherwin, R. RegII is a beta-cell protein and autoantigen in diabetes of NOD mice. *Diabetes* 56, 34-40 (2007).
43. Matsumoto, S. et al. Isolation of tissue progenitor cells from duct-ligated salivary glands of swine. *Cloning Stem Cells* 9, 176-190 (2007).

44. Baert, F. et al. Influence of immunogenicity on the long-term efficacy of infliximab in Crohn's disease. *N Engl J Med* 348, 601-608 (2003).
45. Arnon T I, Lev M, Katz G, Chernobrov Y, Porgador A, Mandelboim O. Recognition of viral hemagglutinins by NKp44 but not by NKp30. Eur J. Immunol. 2001; 31:2680-2689
46. Arnon T I, Achdout H, Lieberman N, Gazit R, Gonen-Gross T, Katz G, Bar-Ilan A, Bloushtain N, Lev M, Joseph A, Kedar E, Porgador A, Mandelboim O. The mechanisms controlling the recognition of tumor and virus infected cells by NKp46. Blood. 2004; 103:664-672

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for treating type 1 diabetes, the method comprising administering to a subject in need thereof, a therapeutically effective amount of a composition comprising at least one protein and a pharmaceutically acceptable carrier, wherein the protein comprises a natural cytotoxicity receptor p46 (NKp46) or an isolated fragment of the extracellular region of NKp46, wherein the isolated fragment of the extracellular region of NKp46 comprises the D2 domain, thereby treating type 1 diabetes in the subject.

2. The method according to claim 1, wherein the type 1 diabetes is immune-mediated diabetes.

3. The method according to claim 1, wherein the NKp46 is human NKp46.

4. The method according to claim 1, wherein the isolated fragment of the extracellular region of NKp46 is devoid of the D1 domain.

5. The method according to claim 1, wherein the D2 domain is selected from the group consisting of SEQ ID NO:1; SEQ ID NO:2; SEQ ID NO:3; SEQ ID NO:4; SEQ ID NO:9 and SEQ ID NO:10.

6. The method according to claim 1, wherein the isolated fragment of the extracellular region of NKp46 comprises a D2 domain variant and wherein the variant comprises at least one amino acid substitution in the D2 domain.

7. The method according to claim 6, wherein the at least one amino acid substitution is at a residue selected from the group consisting of threonine 125, threonine 225, lysine 157, lysine 170, arginine 160, arginine 166, histidine 163, asparagine 216, and a combination thereof, where the numbers correspond to the residue positions of SEQ ID NO:29, or wherein the at least one amino acid substitution is selected from the group consisting of T125A; T225A; T225S; T225N; N216A; K157Q; R160Q; H163Q; R166Q; K170T and a combination thereof, where the numbers correspond to the residue positions of NKp46 of SEQ ID NO:29.

8. The method according to claim 6, wherein the D2 domain variant is selected from the group consisting of SEQ ID NOs:12-16.

9. The method according to claim 1, wherein the protein comprising the NKp46 or an isolated fragment of the extracellular region of NKp46 is present in a fusion protein or a protein conjugate.

10. The method according to claim 9, wherein the fusion protein comprises a first segment and a second segment, wherein the first segment comprises the D2 domain, and wherein the second segment comprises at least one heterologous protein selected from the group consisting of an immunoglobulin, a cytokine, an immunomodulatory protein or peptide, an NK receptor other than NKp46, a hormone, a growth factor and fragments thereof.

11. The method according to claim 10, wherein the heterologous protein is an immunoglobulin fragment or wherein the heterologous protein is the Fc region of IgG1.

12. The method according to claim 9, wherein the fusion protein comprises an amino acid sequence selected from the group consisting of SEQ ID NOs:17-22.

13. The method according to claim 9, wherein the fusion protein comprises a D2 domain variant as the first segment and the Fc region of IgG1 as the second segment, wherein the D2 domain variant comprises at least one amino acid substitution in the D2 domain at a residue selected from the group consisting of threonine 125, threonine 225, lysine 157, lysine 170, arginine 160, arginine 166, histidine 163, asparagine 216, and a combination thereof, where the numbers correspond to the residue positions of SEQ ID NO:29.

14. The method according to claim 13, wherein the first segment comprises an amino acid sequence selected from the group consisting of SEQ ID NOS:12-16.

15. The method according to claim 10, wherein the cytokine is selected from the group consisting of IL-2, IL-4 and IL-10; or wherein the immunomodulatory protein or peptide is selected from the group consisting of heat shock protein 60 (HSP60) or a fragment thereof, roquinimex, Q fever complement-fixing antigen (QFA), anti-CD3 antibody and a combination thereof; or wherein the NK receptor other than NKp46 is NKG2D; or wherein the hormone is selected from the group consisting of insulin, glucagon and a combination thereof.

16. The method according to claim 2, comprising administering the composition at a stage of type 1 diabetes selected from the group consisting of pre-insulitis, early insulitis, pre-diabetes, overt diabetes and a combination thereof.

17. The method according to claim 1, wherein the administering is carried out by a route selected from the group consisting of parenteral, oral, transdermal and topical.

18. The method according to claim 1, further comprising administering at least one immunostimulatory agent in conjunction with administering the composition.

* * * * *